(12) United States Patent
Sorge

(10) Patent No.: US 7,767,396 B2
(45) Date of Patent: Aug. 3, 2010

(54) COMPOSITIONS FOR DETECTION OF A TARGET NUCLEIC ACID SEQUENCE

(75) Inventor: Joseph A. Sorge, Del Mar, CA (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 11/442,065

(22) Filed: May 25, 2006

(65) Prior Publication Data

US 2007/0161011 A1    Jul. 12, 2007

Related U.S. Application Data

(60) Division of application No. 09/728,574, filed on Nov. 30, 2000, now Pat. No. 7,118,860, which is a continuation-in-part of application No. 09/650,888, filed on Aug. 30, 2000, now Pat. No. 6,548,250, which is a continuation-in-part of application No. 09/430,692, filed on Oct. 29, 1999, now Pat. No. 6,528,254.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search .................. 435/6; 536/23.1, 24.3
See application file for complete search history.

(56) References Cited

U.S. PATENT DOCUMENTS

| | | | | |
|---|---|---|---|---|
| 6,350,580 | B1 * | 2/2002 | Sorge ............................. | 435/6 |
| 6,432,642 | B1 * | 8/2002 | Livak et al. .................... | 435/6 |
| 6,528,254 | B1 * | 3/2003 | Sorge ............................. | 435/6 |
| 6,548,250 | B1 * | 4/2003 | Sorge ............................. | 435/6 |
| 6,589,743 | B2 * | 7/2003 | Sorge ............................. | 435/6 |
| 7,118,860 | B2 * | 10/2006 | Sorge et al. .................... | 435/6 |

OTHER PUBLICATIONS

Lundberg et al. High fidelity amplification using a thermostable DNA polymerase from Pyrococccus furiosus. Gene 108(1) : 1-6 (1991).*
The Stratagene Catalog p. 39 (1988).*
Gene Characterization Kits ; The Stratagene Catalog p. 39 (1988).*
Marras et al. Multiplex detection of single-nucleotide variations using molecular beacons. Genetic Analysis : Biomolecular Engineering 14 : 151-156 (1999).*

* cited by examiner

*Primary Examiner*—Ethan Whisenant
(74) *Attorney, Agent, or Firm*—Theodore Allen; Paul Muzzi

(57) ABSTRACT

The invention relates to compositions for generating a signal indicative of the presence of a target nucleic acid in a sample, where the compositions include a probe having a 5' region and a 3' flap and a *P. furiosus* polymerase having 3' exonuclease activity.

9 Claims, 20 Drawing Sheets

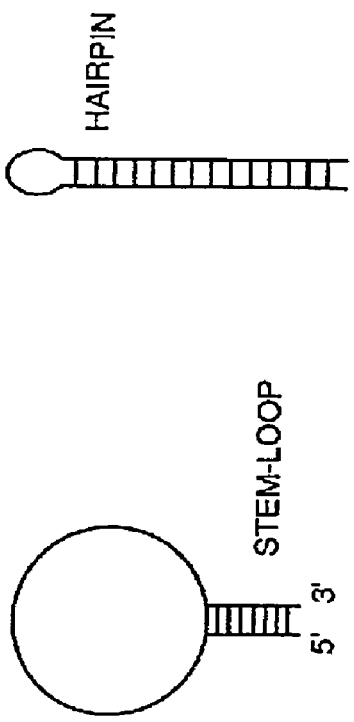
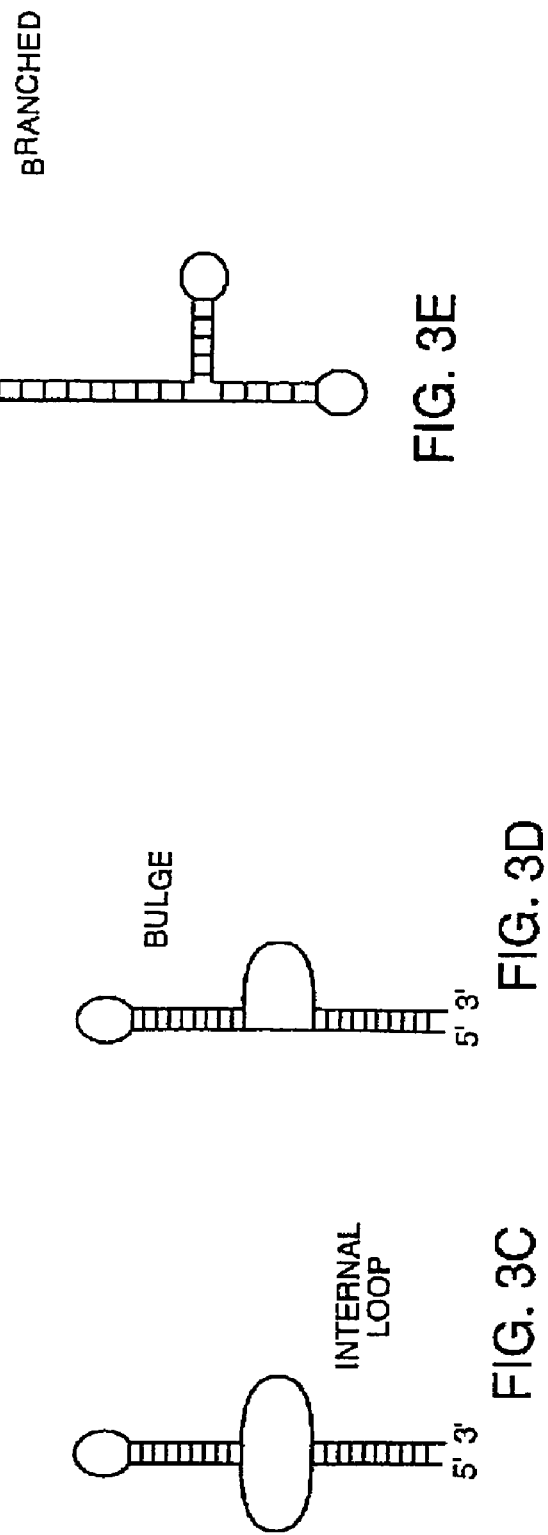
FIG. 3A STEM-LOOP
FIG. 3B HAIRPIN
FIG. 3C INTERNAL LOOP
FIG. 3D BULGE
FIG. 3E BRANCHED

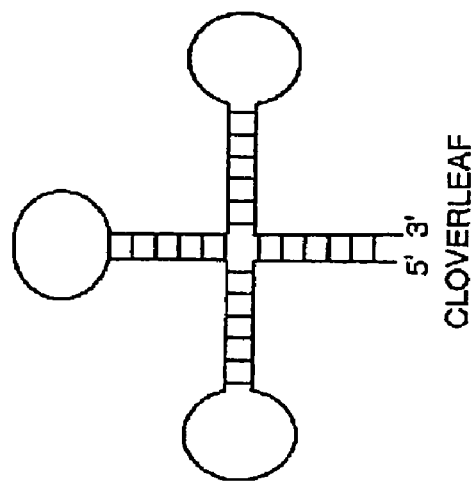
FIG. 3G CLOVERLEAF
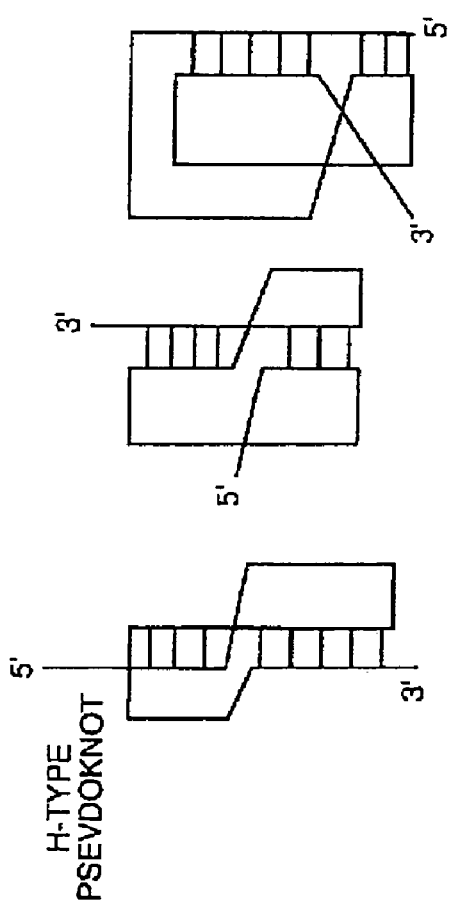
FIG. 3F H-TYPE PSEVDOKNOT
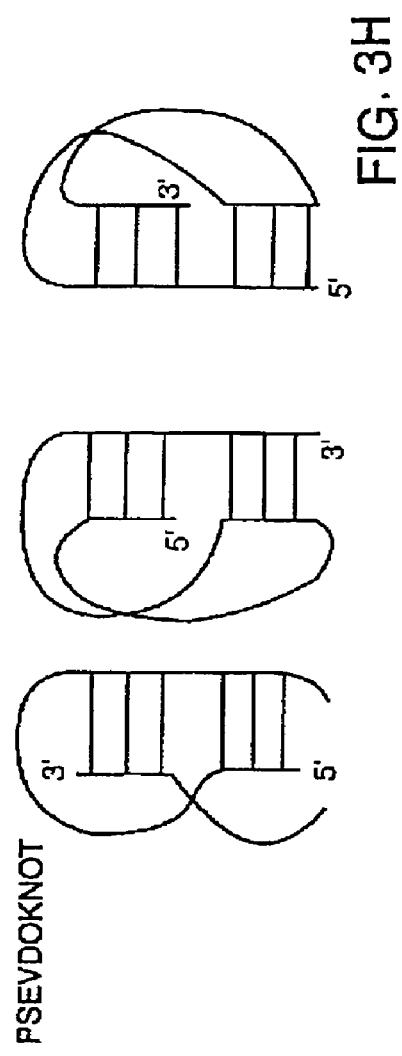
FIG. 3H PSEVDOKNOT

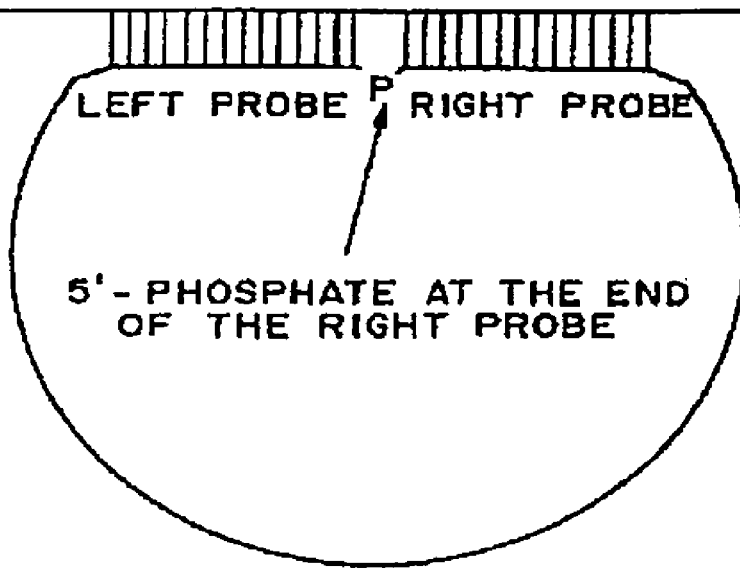
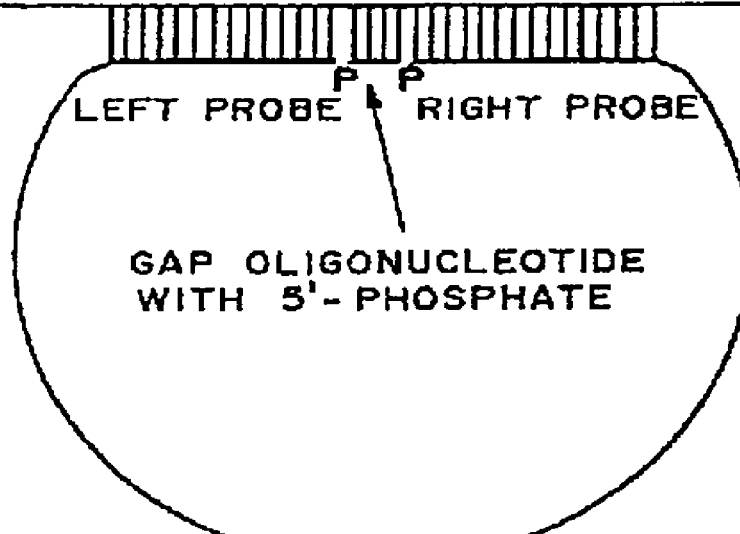
FIG. 8A

COMPOSITIONS FOR DETECTION OF A TARGET NUCLEIC ACID SEQUENCE

RELATED APPLICATIONS

This application is a divisional which claims priority under 35 U.S.C. §121 to U.S. patent application Ser. No. 09/728,574 filed Nov. 30, 2000, which is a continuation-in-part of U.S. patent application Ser. No. 09/650,888 filed Aug. 30, 2000 (now U.S. Pat. No. 6,548,250), which is a continuation-in-part of U.S. patent application Ser. No. 09/430,692 filed Oct. 29, 1999 (now U.S. Pat. No. 6,528,254), the entireties of which are incorporated herein by reference.

FIELD OF THE INVENTION

The invention relates in general to methods of detecting or measuring a target nucleic acid.

BACKGROUND OF THE INVENTION

The fidelity of DNA replication, recombination, and repair is essential for maintaining genome stability, and these processes depend on 5'→3' exonuclease enzymes which are present in all organisms. For DNA repair, these enzymes are required for damaged fragment excision and recombinational mismatch correction. For replication, these nucleases are critical for the efficient processing of Okazaki fragments during lagging strand DNA synthesis. In *Escherichia coli*, this latter activity is provided by DNA polymerase I (PolI); *E. coli* strains with inactivating mutations in the PolI 5'→3' exonuclease domain are not viable due to an inability to process Okazaki fragments. Eukaryotic DNA polymerases, however, lack an intrinsic 5'→3' exonuclease domain, and this critical activity is provided by the multifunctional, structure-specific metallonuclease FEN-1 (five' exonuclease-1 or flap endonuclease-1), which also acts as an endonuclease for 5' DNA flaps (Reviewed in Hosfield et al., 1998a, *Cell*, 95:135).

Methods of detecting and/or measuring a nucleic acid wherein an enzyme produces a labeled nucleic acid fragment are known in the art.

U.S. Pat. Nos. 5,843,669, 5,719,028, 5,837,450, 5,846,717 and 5,888,780 disclose a method of cleaving a target DNA molecule by incubating a 5' labeled target DNA with a DNA polymerase isolated from *Thermus aquaticus* (Taq polymerase) and a partially complementary oligonucleotide capable of hybridizing to sequences at the desired point of cleavage. The partially complementary oligonucleotide directs the Taq polymerase to the target DNA through formation of a substrate structure containing a duplex with a 3' extension opposite the desired site of cleavage wherein the non-complementary region of the oligonucleotide provides a 3' arm and the unannealed 5' region of the substrate molecule provides a 5' arm. The partially complementary oligonucleotide includes a 3' nucleotide extension capable of forming a short hairpin either when unhybridized or when hybridized to a target sequence at the desired point of cleavage. The release of labeled fragment is detected following cleavage by Taq polymerase.

U.S. Pat. Nos. 5,843,669, 5,719,028, 5,837,450, 5,846,717 and 5,888,780 disclose the generation of mutant, thermostable DNA polymerases that have very little or no detectable synthetic activity, and wild type thermostable nuclease activity. The mutant polymerases are said to be useful because they lack 5' to 3' synthetic activity; thus synthetic activity is an undesirable side reaction in combination with a DNA cleavage step in a detection assay.

U.S. Pat. Nos. 5,843,669, 5,719,028, 5,837,450, 5,846,717 and 5,888,780 disclose that wild type Taq polymerase or mutant Taq polymerases that lack synthetic activity can release a labeled fragment by cleaving a 5' end labeled hairpin structure formed by heat denaturation followed by cooling, in the presence of a primer that binds to the 3' arm of the hairpin structure. Further, U.S. Pat. Nos. 5,843,669, 5,719,028, 5,837,450, 5,846,717 and 5,888,780 teach that the mutant Taq polymerases lacking synthetic activity can also cleave this hairpin structure in the absence of a primer that binds to the 3' arm of the hairpin structure.

U.S. Pat. Nos. 5,843,669, 5,719,028, 5,837,450, 5,846,717 and 5,888,780 also disclose that cleavage of this hairpin structure in the presence of a primer that binds to the 3' arm of the hairpin structure by mutant Taq polymerases lacking synthetic activity yields a single species of labeled cleaved product, while wild type Taq polymerase produces multiple cleavage products and converts the hairpin structure to a double stranded form in the presence of dNTPs, due to the high level of synthetic activity of the wild type Taq enzyme.

U.S. Pat. Nos. 5,843,669, 5,719,028, 5,837,450, 5,846,717 and 5,888,780 also disclose that mutant Taq polymerases exhibiting reduced synthetic activity, but not wild type Taq polymerase, can release a single labeled fragment by cleaving a linear nucleic acid substrate comprising a 5' end labeled target nucleic acid and a complementary oligonucleotide wherein the complementary oligonucleotide hybridizes to a portion of the target nucleic acid such that 5' and 3' regions of the target nucleic acid are not annealed to the oligonucleotide and remain single stranded.

There is a need in the art for a method of generating a signal that can be easily distinguished from oligonucleotide fragments that may arise from nuclease contaminants, using a nucleic acid cleavage reaction.

There is a need in the art for a method of generating a signal that utilizes a probe comprising secondary structure wherein some or all of the self-complementary regions of the probe that anneal to form the secondary structure are melted when the probe hybridizes with a target nucleic acid, thereby reducing non-specific binding of the probe to the target, and increasing the specificity of the assay.

U.S. Pat. Nos. 5,843,669, 5,719,028, 5,837,450, 5,846,717 and 5,888,780 also disclose a method of cleaving a labeled nucleic acid substrate at naturally occurring areas of secondary structure. According to this method, biotin labeled DNA substrates are prepared by PCR, mixed with wild type Taq polymerase or CleavaseBN (a mutant Taq polymerase with reduced synthetic activity and wild type 5' to 3' nuclease activity), incubated at 95° C. for 5 seconds to denature the substrate and then quickly cooled to 65° C. to allow the DNA to assume its unique secondary structure by allowing the formation of intra-strand hydrogen bonds between the complementary bases. The reaction mixture is incubated at 65° C. to allow cleavage to occur and biotinylated cleavage products are detected.

There is a need in the art for a method of generating a signal using a nucleic acid cleavage reaction wherein the cleavage structure is not required to contain areas of secondary structure.

Methods of detecting and/or measuring a nucleic acid wherein a FEN-1 enzyme is used to generate a labeled nucleic acid fragment are known in the art.

U.S. Pat. No. 5,843,669 discloses a method of detecting polymorphisms by cleavage fragment length polymorphism analysis using a thermostable FEN-1 nuclease in the presence or absence of a mutant Taq polymerase exhibiting reduced synthetic activity. According to this method, double stranded Hepatitis C virus (HCV) DNA fragments are labeled by using 5' end labeled primers (labeled with TMR fluorescent dye) in a PCR reaction. The TMR labeled PCR products are denatured by heating to 95° C. and cooled to 55° C. to generate a cleavage structure. U.S. Pat. No. 5,843,669 discloses that a cleavage structure comprises a region of a single stranded nucleic acid substrate containing secondary structure. Cleavage is carried out in the presence of CleavaseBN nuclease, FEN-1 nuclease derived from the archaebacteria *Methanococcus jannaschii* or both enzymes. Labeled reaction products are visualized by gel electrophoresis followed by fluoroimaging. U.S. Pat. No. 5,843,669 discloses that CleavaseBN nuclease and *Methanococcus jannaschii* FEN-1 nuclease produce cleavage patterns that are easily distinguished from each other, and that the cleavage patterns from a reaction containing both enzymes include elements of the patterns produced by cleavage with each individual enzyme but are not merely a composite of the cleavage patterns produced by each individual enzyme. This indicates that some of the fragments that are not cleaved by one enzyme (and which appear as a band in that enzyme's pattern) can be cleaved by a second enzyme in the same reaction mixture.

Lyamichev et al. disclose a method for detecting DNAs wherein overlapping pairs of oligonucleotide probes that are partially complementary to a region of target DNA are mixed with the target DNA to form a 5' flap region, and wherein cleavage of the labeled downstream probe by a thermostable FEN-1 nuclease produces a labeled cleavage product. Lyamichev et al. also disclose reaction conditions wherein multiple copies of the downstream oligonucleotide probe can be cleaved for a single target sequence in the absence of temperature cycling, so as to amplify the cleavage signal and allow quantitative detection of target DNA at sub-attomole levels (Lyamichev et al., 1999, *Nat. Biotechnol.*, 17:292).

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science*, 230:1350.

While the PCR technique is an extremely powerful method for amplifying nucleic acid sequences, the detection of the amplified material requires additional manipulation and subsequent handling of the PCR products to determine whether the target DNA is present. It is desirable to decrease the number of subsequent handling steps currently required for the detection of amplified material. An assay system, wherein a signal is generated while the target sequence is amplified, requires fewer handling steps for the detection of amplified material, as compared to a PCR method that does not generate a signal during the amplification step.

U.S. Pat. Nos. 5,210,015 and 5,487,972 disclose a PCR based assay for releasing labeled probe comprising generating a signal during the amplification step of a PCR reaction in the presence of a nucleic acid to be amplified, Taq polymerase that has 5' to 3' exonuclease activity and a 5', 3' or 5' and 3' end-labeled probe comprising a region complementary to the amplified region and an additional non-complementary 5' tail region. U.S. Pat. Nos. 5,210,015 and 5,487,972 disclose further that this PCR based assay can liberate the 5' labeled end of a hybridized probe when the Taq polymerase is positioned near the labeled probe by an upstream probe in a polymerization independent manner, e.g. in the absence of dNTPs.

There is a need in the art for a method of detecting or measuring a target nucleic acid that does not require multiple steps.

There is also a need in the art for a PCR process for detecting or measuring a target nucleic acid that does not require multiple steps subsequent to the amplification process.

There is also a need in the art for a PCR process for detecting or measuring a target nucleic acid that allows for concurrent amplification and detection of a target nucleic acid in a sample.

SUMMARY OF THE INVENTION

The invention provides a method of generating a signal indicative of the presence of a target nucleic acid in a sample, which includes the steps of forming a cleavage structure by incubating a sample containing a target nucleic acid with a probe containing a binding moiety and having a secondary structure that changes upon binding of the probe to a target nucleic acid, and cleaving the cleavage structure with a nuclease to release a nucleic acid fragment and thus generate a signal. Nuclease cleavage of the cleavage structure occurs at a cleaving temperature, and the secondary structure of the probe when not bound to the target nucleic acid is stable at or below the cleaving temperature. Generation of the signal is indicative of the presence of a target nucleic acid in the sample, and the signal is detected or measured by detecting and/or measuring the amount of the fragment captured by binding of the binding moiety to a capture element on a solid support.

As used herein, a "probe" refers to a single stranded nucleic acid comprising a region or regions that are complementary to a target nucleic acid (e.g., target nucleic acid binding sequences) (for example C in FIG. 4). A "probe" according to the invention has a secondary structure that changes upon binding of the probe to the target nucleic acid and further comprises a binding moiety. A "probe" according to the invention binds to a target nucleic acid to form a cleavage structure that can be cleaved by a nuclease, wherein cleaving is performed at a cleaving temperature, and wherein the secondary structure of the probe when not bound to the target nucleic acid is, preferably, stable at or below the cleaving temperature. A probe according to the invention cannot be cleaved to generate a signal by a "nuclease", as defined herein, prior to binding to a target nucleic acid. In one embodiment of the invention, a probe may comprise a region that cannot bind or is not complementary to a target nucleic acid. In another embodiment of the invention, a probe does not have a secondary structure when bound to a target nucleic acid.

As used herein, "secondary structure" refers to a three-dimensional conformation (for example a hairpin, a stem-loop structure, an internal loop, a bulge loop, a branched structure or a pseudoknot, FIGS. 1 and 3; multiple stem loop structures, cloverleaf type structures or any three dimensional structure. As used herein, "secondary structure" includes tertiary, quaternary etc. . . . structure. A probe comprising such a three-dimensional structure binds to a target nucleic acid to form a cleavage structure that can be cleaved by a nuclease at a cleaving temperature. The three dimensional structure of the probe when not bound to the target nucleic acid is, preferably, stable at or below the cleaving temperature. "Secondary structure" as used herein, can mean a sequence comprising a first single-stranded sequence of bases (referred to herein as a "complementary nucleic acid sequence" (for example b in FIG. 4)) followed by a second complementary sequence either in the same molecule (for example b' in FIG. 4), or in a second molecule comprising the probe, folds back on itself to generate an antiparallel duplex structure, wherein the single-stranded sequence and the complementary sequence (that is, the complementary nucleic acid sequences) anneal by the formation of hydrogen bonds. Oligonucleotide probes, as used in the present invention include oligonucleotides comprising secondary structure, including, but not limited to molecular beacons, safety pins (FIG. 9), scorpions (FIG. 10), and sunrise/amplifluor probes (FIG. 11), the details and structures of which are described below and in the corresponding figures.

As used herein, first and second "complementary" nucleic acid sequences are complementary to each other and can anneal by the formation of hydrogen bonds between the complementary bases.

A secondary structure also refers to the conformation of a nucleic acid molecule comprising an affinity pair, defined herein, wherein the affinity pair reversibly associates as a result of attractive forces that exist between the pair of moieties comprising the affinity pair. As used herein, secondary structure prevents the binding moiety on the probe from binding to a capture element, and a change in secondary structure upon binding of the probe to the target nucleic acid and subsequent cleavage of the bound probe permits the binding moiety to be captured by the capture element.

A "probe" according to the invention can be unimolecular. As used herein, a "unimolecular" probe comprises a single molecule that binds to a target nucleic acid to form a cleavage structure that can be cleaved by a nuclease, wherein cleaving is performed at a cleaving temperature, and wherein the secondary structure of the "unimolecular" probe when not bound to the target nucleic acid is, preferably, stable at or below the cleaving temperature. Unimolecular probes useful according to the invention include but are not limited to beacon probes, probes comprising a hairpin, stem-loop, internal loop, bulge loop or pseudoknot structure, scorpion probes and sunrise/amplifluor probes.

A "probe" according to the invention can be more than one molecule (e.g., bi-molecular or multi-molecular). At least one of the molecules comprising a bi-molecular or multi-molecular probe binds to a target nucleic acid to form a cleavage structure that can be cleaved by a nuclease, wherein cleaving is performed at a cleaving temperature, and wherein the secondary structure of the molecule of the probe when not bound to the target nucleic acid is, preferably, stable at or below the cleaving temperature. The molecules comprising the multi-molecular probe associate with each other via intermolecular bonds (e.g., hydrogen bonds or covalent bonds). For example, a heterologous loop (see FIG. 1), or a cloverleaf structure wherein one or more loops of the cloverleaf structure comprises a distinct molecule, and wherein the molecules that associate to form the cloverleaf structure associate via intermolecular bonding (e.g., hydrogen bonding or covalent bonding), are examples of multimolecular probes useful according to the invention.

As used herein, a "molecule" refers to a polynucleotide, and includes a polynucleotide further comprising an attached member or members of an affinity pair.

A "probe" or a "molecule" comprising a probe is 5-10,000 nucleotides in length, ideally from 6-5000, 7-1000, 8-500, 9-250, 10-100 and 17-40 nucleotides in length, although probes or a molecule comprising a probe of different lengths are useful.

A "probe" according to the invention has a target nucleic acid binding sequence that is from 5 to 10,000 nucleotides, and preferably from 10 to about 140 nucleotides. A "probe" according to the invention comprises at least first and second complementary nucleic acid sequences or regions that are 3-250, preferably 4-150, and more preferably 5-110 and most preferably 6-50 nucleotides long. The first and second complementary nucleic acid sequences may have the same length or may be of different lengths. The invention provides for a probe wherein the first and second complementary nucleic acid sequences are both located upstream (5') of the target nucleic acid binding site. Alternatively, the first and second complementary nucleic acid sequences can both be located downstream (3') of the target nucleic acid binding site. In another embodiment, the invention provides for a probe wherein the first complementary nucleic acid sequence is upstream (5') of the target nucleic acid binding site and the second complementary nucleic acid sequence is downstream (3') of the target nucleic acid binding site. In another embodiment, the invention provides for a probe wherein the second complementary nucleic acid sequence is upstream (5') of the target nucleic acid binding site and the first complementary nucleic acid sequence is downstream (3') of the target nucleic acid binding site. The actual length will be chosen with reference to the target nucleic acid binding sequence such that the secondary structure of the probe is, preferably, stable when the probe is not bound to the target nucleic acid at the temperature at which cleavage of a cleavage structure comprising the probe bound to a target nucleic acid is performed. As the target nucleic acid binding sequence increases in size up to 500 nucleotides, the length of the complementary nucleic acid sequences may increase up to 15-125 nucleotides. For a target nucleic acid binding sequence greater than 100 nucleotides, the length of the complementary nucleic acid sequences need not be increased further. If the probe is also an allele-discriminating probe, the lengths of the complementary nucleic acid sequences are more restricted, as is discussed below.

As used herein, the "target nucleic acid binding sequence" refers to the region of the probe that binds specifically to the target nucleic acid.

A "hairpin structure" or a "stem" refers to a double-helical region formed by base pairing between adjacent, inverted, complementary sequences in a single strand of RNA or DNA.

A "stem-loop" structure refers to a hairpin structure, further comprising a loop of unpaired bases at one end.

As used herein, a probe with "stable" secondary structure when not bound to a target nucleic acid, refers to a secondary structure wherein 50% or more (e.g., 50%, 55%, 75% or 100%) of the base pairs that constitute the probe are not dissociated under conditions which permit hybridization of the probe to the target nucleic acid, but in the absence of the target nucleic acid.

"Stability" of a nucleic acid duplex is determined by the melting temperature, or "$T_m$". The $T_m$ of a particular nucleic acid duplex under specified conditions (e.g., salt concentration and/or the presence or absence of organic solvents) is the temperature at which half (50%) of the base pairs of the duplex molecule have disassociated (that is, are not hybridized to each other in a base-pair).

The "stability" of the secondary structure of a probe when not bound to the target nucleic acid is defined in a melting temperature assay, in a fluorescence resonance energy transfer (FRET) assay or in a fluorescence quenching assay, (the details or which are described in a section entitled, "Determining the Stability or the Secondary Structure of a Probe").

A probe useful in the invention preferably will have secondary structure that is "stable", when not bound to a target, at or below the temperature of the cleavage reaction. Thus, the temperature at which nuclease cleavage of a probe/target nucleic acid hybrid is performed according to the invention, must be lower than the Tm of the secondary structure. The secondary structure of the probe is "stable" in a melting temperature assay at a temperature that is at or below the temperature of the cleavage reaction (i.e., at which cleavage is performed) if the level of light absorbance at the temperature at or below the temperature of the cleavage reaction is less than (i.e., at least 5% less than, preferably 20% less than and most preferably 25% less than etc. . . .) than the level of light absorbance at a temperature that is equal to or greater than the Tm of the probe.

According to the method of the invention, the stability of a secondary structure can be measured by a FRET assay or a fluorescence quenching assay (described in the section entitled, "Determining the Stability of the Secondary Structure of a Probe"). As used herein, a fluorescence quenching assay can include a FRET assay. A probe according to the invention is labeled with an appropriate pair of interactive labels (e.g., a FRET pair (for example as described in the section entitled, "Determining the Stability of the Secondary Structure of the Probe", below) that can interact over a distance of, for example 2 nucleotides, or a non-FRET-pair, (e.g., tetramethylrhodamine and DABCYL) that can interact over a distance of, for example, 20 nucleotides. For example, a probe according to the invention may be labeled with a fluorophore and a quencher and fluorescence is then measured, in the absence of a target nucleic acid, at different temperatures. The Tm is the temperature at which the level of fluorescence is 50% of the maximal level of fluorescence observed for a particular probe, see FIG. 12e. The Tm for a particular probe wherein the nucleic acid sequence of the probe is known, can be predicted according to methods known in the art. Thus, fluorescence is measured over a range of temperatures, e.g., wherein the lower temperature limit of the range is at least 50° Celsius below, and the upper temperature limit of the range is at least 50° Celsius above the Tm or predicted Tm, for a probe according to the invention.

A secondary structure is herein defined as "stable" in a FRET assay at a temperature that is at or below the cleaving temperature if the level or wavelength of fluorescence is increased or decreased (e.g., at least 5% less than, preferably 20% less than and more preferably 25% less than, etc. . . .) as compared with the level or wavelength of FRET that is observed at the Tm of the probe (see FIGS. 12e and f). For example, an increase or a decrease in FRET can occur in a FRET assay according to the invention. In another embodiment, a shift in wavelength, which results in an increase in the new, shifted wavelength or, a decrease in the new shifted wavelength, can occur in a FRET assay according to the invention.

A "change" in a secondary structure, according to the invention can be measured in a fluorescence quenching assay wherein a probe according to the invention comprises a fluorophore and a quencher that are positioned such that in the absence of a target nucleic acid, and at temperatures below the Tm of the probe there is quenching of the fluorescence (as described above). As used herein, a "change" in secondary structure that occurs when a probe according to the invention binds to a target nucleic acid, refers to an increase in fluorescence in such an assay, such that the level of fluorescence after binding of the probe to the target nucleic acid at a temperature below the Tm of the probe, is greater than (e.g., at least 5%, preferably 5-20% and most preferably 25% or more) the level of fluorescence observed in the absence of a target nucleic acid (see FIG. 12g).

A secondary structure, according to the invention, can be detected by subjecting a probe comprising a fluorophore and a quencher to a fluorescence quenching assay (as described above). A probe that exhibits a change in fluorescence that correlates with a change in temperature, see FIG. 12e (e.g., fluorescence increases as the temperature of the FRET reaction is increased) may be capable of forming a secondary structure.

As used herein, a "cleaving temperature" that is useful according to the invention is a temperature that is less than (at least 1° C. and preferably 10° C.) the $T_m$ of a probe having a secondary structure. The "cleaving temperature" is initially selected to be possible and preferably optimal for the particular nuclease being employed in the cleavage reaction.

Preferably the 3' terminus of the probe will be "blocked" to prohibit incorporation of the probe into a primer extension product if an active polymerase is used in the reaction. "Blocking" can be achieved by using non-complementary bases or by adding a chemical moiety such as biotin or a phosphate group to the 3' hydroxl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as dideoxynucleotide.

The term probe encompasses an allele-discriminating probe. As used herein, an "allele-discriminating" probe preferentially hybridizes to perfectly complementary target nucleic acids and discriminates against sequences that vary by at least one nucleotide. A nucleic acid sequence which differs by at least one nucleotide, as compared to a target nucleic acid, hereafter referred to as a "target-like nucleic acid sequence", is thus not a target nucleic acid for an allele-discriminating probe according to the invention. Allele-discriminating probes do not hybridize sufficiently to a target-like nucleic acid sequence that contains one or more nucleotide mismatches as compared to the target nucleic acid complementary sequence, at a particular temperature or within a range of temperatures determined by experimental optimization to permit an allele discriminating probe to discriminate between a target and a target-like sequence with at least a single nucleotide difference, and thus do not undergo a change in secondary structure upon binding to a target-like nucleic acid sequence in the presence of only a target-like nucleic acid sequence, and under conditions that would support hybridization of the allele discriminating probe to a target nucleic acid.

In one embodiment, an "allele-discriminating probe" according to the invention refers to a probe that hybridizes to a target-like nucleic acid sequence that varies by at least one nucleotide from the target nucleic acid, wherein the variant nucleotide(s) is/are not located in the allele-discriminating site. According to this embodiment of the invention, "an allele-discriminating probe" cannot bind to a target-like nucleic acid sequence that also varies by at least one nucleotide in the allele-discriminating site, at a particular temperature or within a range of temperatures determined by experimental optimization to permit an allele discriminating probe to discriminate between a target and a target-like sequence with at least a single nucleotide difference. Single nucleotide differences only affect the percentage of a probe that is bound to a target or target-like nucleic acid sequence. For example, the invention provides for a perfectly matched probe, wherein as much as 100% of the target or is in a probe-target complex (e.g., is bound by probe), in the presence of excess probe. The invention also provides for probes comprising at least a single base mismatch wherein at least 1-5% and preferably 5-10% of the target-like sequence is bound by the probe under the same conditions used to form a complex comprising a target sequence and a perfectly matched probe.

As used herein, "allele-discriminating site" refers to a region of a target nucleic acid that is different (i.e., by at least one nucleotide) from the corresponding region in all possible alleles comprising the target nucleic acid.

Allele-discriminating probes useful according to the invention also include probes that bind less effectively to a target-like sequence, as compared to a target sequence. The effectiveness of binding of a probe to a target sequence or a target-like sequence can be measured in a FRET assay, performed at a temperature that is below (at least 1° C. and preferably 10° C. or more) the Tm of the secondary structure of the probe, in the presence of a target-like sequence or a target sequence. The change in the level of fluorescence in the presence or absence of a target sequence compared to the change in the level of fluorescence in the presence or absence of a target-like sequence, provides an effective measure of the effectiveness of binding of a probe to a target or target-like sequence.

In a method according to the invention, a probe that binds less effectively to a target-like sequence as compared to a target sequence would undergo a smaller (e.g., preferably 25-50%, more preferably 50-75% and most preferably 75-90% of the value of the change in fluorescence upon binding to a target nucleic acid) change in secondary structure, as determined by measuring fluorescence in a FRET or fluorescence quenching assay as described herein, upon hybridization to a target-like sequence as compared to a target nucleic acid. In a method according to the invention, a probe that binds less effectively to a target-like sequence as compared to a target sequence would generate a signal that is indicative of the presence of a target-like nucleic acid sequence in a sample. However, the intensity of the signal would be altered (e.g., preferably 25-50%, more preferably 50-75% and most preferably 75-90% less than or more than the value of the change in fluorescence upon binding to a target nucleic acid) the intensity of a signal generated in the presence of a target sequence, as described hereinabove for a smaller change.

A "signal that is indicative of the presence of a target nucleic acid" or a "target-like nucleic acid sequence" refers to a signal that is equal to a signal generated from 1 molecule to $10^{20}$ molecules, more preferably about 100 molecules to $10^{17}$ molecules and most preferably about 1000 molecules to $10^{14}$ molecules of a target nucleic acid or a target-like nucleic acid sequence.

As used herein, a "binding moiety" refers to a region of a probe (for example ab in FIG. 4) that is released upon cleavage of the probe by a nuclease and binds specifically to a capture element as a result of attractive forces that exist between the binding moiety and the capture element, and wherein specific binding between the binding moiety and the capture element only occurs when the secondary structure of the probe has "changed", as defined herein. "Binds specifically" means via hydrogen bonding with a complementary nucleic acid or via an interaction between for example, the binding moiety and a binding protein capable of binding specifically to the nucleic acid sequence of the binding moiety. A "binding moiety" does not interfere with the ability of a probe to bind to a target nucleic acid. A binding moiety is incapable of binding to a capture element when the probe is in its native secondary structural conformation and that, upon binding to a target or template nucleic acid, the secondary structure changes in a way that allows the binding moiety to bind to the capture element, preferably after cleavage by a cleavage agent.

In one embodiment, the region of a probe that is cleaved to form a binding moiety cannot hybridize to a target nucleic acid. The region of a "binding moiety" that is not a "complementary nucleic acid sequence", as defined herein, (e.g., a in FIG. 4), is from 1-60 nucleotides, preferably from 1-25 nucleotides and most preferably from 1-10 nucleotides in length. Methods of detecting specific binding between a binding moiety or a binding moiety, as defined herein, and a capture element, as defined herein, are well known in the art and are described hereinbelow.

In one embodiment of the invention, a probe further comprises a "reporter".

As used herein, a "reporter" refers to a "label", defined hereinbelow and/or a "tag" defined hereinbelow.

As used herein, "label" or "labeled moiety capable of providing a signal" refers to any atom or molecule which can be used to provide a detectable (preferably quantifiable) signal, and which can be operatively linked to a nucleic acid. Labels may provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. A labeled probe according to the methods of the invention is labeled at the 5' end, the 3' end or internally. The label can be "direct", i.e. a dye, or "indirect". i.e. biotin, digoxin, alkaline phosphatase (AP), horse radish peroxidase (HRP) etc. . . . For detection of "indirect labels" it is necessary to add additional components such as labeled antibodies, or enzyme substrates to visualize the, captured, released, labeled nucleic acid fragment. In one embodiment of the invention, a label cannot provide a detectable signal unless the secondary structure has "changed", as defined herein, (for example, such that the binding moiety is accessible).

A "binding moiety" also refers to a "tag". As used herein, a "tag" refers to a moiety that is operatively linked to the 5' end of a probe (for example R in FIG. 1) and specifically binds to a capture element as a result of attractive forces that exist between the tag and the capture element, and wherein specific binding between the tag and the capture element only occurs when the secondary structure of the probe has changed (for example, such that the tag is accessible to a capture element). "Specifically binds" as it refers to a "tag" and a capture element means via covalent or hydrogen bonding or electrostatic attraction or via an interaction between, for example a protein and a ligand, an antibody and an antigen, protein subunits, or a nucleic acid binding protein and a nucleic acid binding site. A tag does not interfere with the ability of a probe to anneal to a target nucleic acid. Tags include but are not limited to biotin, streptavidin, avidin, an antibody, an antigen, a hapten, a protein, or a chemically reactive moiety. A "tag" as defined herein can bind to a "capture element" as defined herein. According to the invention, a "tag" and a "capture element" function as a binding pair. For example, in one embodiment, if a tag is biotin, the corresponding capture element is avidin. Alternatively, in another embodiment, if a tag is an antibody, the corresponding capture element is an antigen.

The invention contemplates a "probe" comprising a binding moiety, a "probe" comprising a "tag", as defined herein, and a "probe" comprising both a binding moiety that is a region of a probe that is released upon cleavage of the probe by a nuclease (for example a nucleic acid sequence that binds to a capture element), and a "tag".

As used herein, a "capture element" refers to a substance that is attached to a solid substrate for example by chemical crosslinking or covalent binding, wherein the substance specifically binds to (e.g., via hydrogen bonding or via an interaction between, a nucleic acid binding protein and a nucleic acid binding site or between complementary nucleic acids) a binding moiety as a result of attractive forces that exist between the binding moiety and the capture element, and wherein specific binding between the binding moiety and the capture element only occurs when the secondary structure of the probe comprising the binding moiety has "changed", as defined herein. Capture elements include but are not limited to a nucleic acid binding protein or a nucleotide sequence.

As used herein, a "capture element" also refers to a substance that is attached to a solid substrate for example by chemical crosslinking or covalent binding, wherein the substance specifically binds to (e.g. via covalent or hydrogen bonding or electrostatic attraction via an interaction between, for example a protein and a ligand, an antibody and an antigen, protein subunits, a nucleic acid binding protein and a nucleic acid binding site or between complementary nucleic acids) a tag as a result of attractive forces that exist between the tag and the capture element, and wherein specific binding between the tag and the capture element only occurs when the secondary structure of the probe comprising the tag has "changed", as defined herein. Capture elements include but are not limited to biotin, avidin, streptavidin, an antibody, an antigen, a hapten, a protein, or a chemically reactive moiety. A "tag" as defined herein can bind to a "capture element" as defined herein. According to the invention, a "tag" and a "capture element" function as a binding pair. For example, in one embodiment, if a capture element is biotin, the corresponding tag is avidin. Alternatively, in another embodiment, if a capture element is an antibody, the corresponding tag is an antigen.

As used herein, "solid support" means a surface to which a molecule (e.g. a capture element) can be irreversibly bound, including but not limited to membranes, sepharose beads, magnetic beads, tissue culture plates, silica based matrices, membrane based matrices, beads comprising surfaces including but not limited to styrene, latex or silica based materials and other polymers for example cellulose acetate, teflon, polyvinylidene difluoride, nylon, nitrocellulose, polyester, carbonate, polysulphone, metals, zeolites, paper, alumina, glass, polypropyle, polyvinyl chloride, polyvinylidene chloride, polytetrafluorethylene, polyethylene, polyamides, plastic, filter paper, dextran, germanium, silicon, (poly)tetrafluorethylene, gallium arsenide, gallium phosphide, silicon oxide, silicon nitrate and combinations thereof. Methods of attaching a capture element as defined herein are well known in the art and are defined hereinbelow. Additional solid supports are also discussed hereinbelow.

As used herein, "affinity pair" refers to a pair of moieties (for example complementary nucleic acid sequences, protein-ligand, antibody-antigen, protein subunits, and nucleic acid binding proteins-binding sites) that can reversibly associate as a result of attractive forces that exist between the moieties. An "affinity pair" includes the combination of a binding moiety and the corresponding capture element and the combination of a tag and the corresponding capture element.

In embodiments wherein the affinity pair comprises complementary nucleic acid regions that reversibly interact with one another, the lengths of the target nucleic acid binding sequences, and the nucleic acid sequences comprising the affinity pair, are chosen for the proper thermodynamic functioning of the probe under the conditions of the projected hybridization assay. Persons skilled in hybridization assays will understand that pertinent conditions include probe, target and solute concentrations, detection temperature, the presence of denaturants and volume excluders, and other hybridization-influencing factors. The length of a target nucleic acid binding sequence can range from 7 to about 10,000 nucleotides, preferably from 8-5000, 9-500, 9-250 and most preferably, 10 to 140 nucleotides. If the probe is also an allele-discriminating probe, the length is more restricted, as is discussed below (this sentence has jumped in logic from a binding moiety:capture element concept to a probe:target concept).

In embodiments wherein the affinity pair comprises complementary nucleic acid regions that reversibly interact with one another, and cannot hybridize or are not complementary to a target nucleic acid, the complementary nucleic acid region sequences of the affinity pair should be of sufficient length that under the conditions of the assay and at the detection temperature, when the probe is not bound to a target, the structure of the probe is such that the binding moiety of the probe will not bind to the capture element, e.g., the complementary nucleic acid sequences are associated. Depending upon the assay conditions used, complementary nucleic acid sequences of 3-25 nucleotide lengths can perform this function. An intermediate range of 4-15, and more preferably 5-11, nucleotides is often appropriate. The actual length will be chosen with reference to the target nucleic acid binding sequence such that the secondary structure of the probe is stable when not bound to the target nucleic acid at the temperature at which cleavage of a cleavage structure comprising the probe bound to a target nucleic acid is performed. As the target nucleic acid binding sequence increases in size up to 100 nucleotides, the length of the complementary nucleic acid sequences may increase up to 15-25 nucleotides. For a target nucleic acid binding sequence greater than 100 nucleotides, the length of the complementary nucleic acid sequences need not be increased further. If the probe is also an allele-discriminating probe, the lengths of the complementary nucleic acid sequences are more restricted, as is discussed below.

Allele-discriminating probes that do not hybridize sufficiently to a target-like nucleic acid sequence that contains one or more nucleotide mismatches as compared to the target nucleic acid complementary sequence, must be designed such that, under the assay conditions used, reduction or elimination of secondary structure in the probe and hybridization with a target nucleic acid will occur efficiently only when the target nucleic acid complementary sequence finds a perfectly complementary target sequence under certain reaction conditions. Certain reaction conditions may include, for example, a particular temperature or a range of temperatures determined by experimental optimization to permit an allele discriminating probe to discriminate between a target and a target-like sequence with at least a single nucleotide difference.

In one embodiment, an "allele-discriminating probe" according to the invention refers to a probe that hybridizes to a target-like nucleic acid sequence that varies by at least one nucleotide from the target nucleic acid, wherein the variant nucleotide(s) is/are not located in the allele-discriminating site. According to this embodiment of the invention, "an allele-discriminating probe" cannot bind efficiently to a tar-get-like nucleic acid sequence that also varies by at least one nucleotide in the allele-discriminating site under certain reaction conditions. Certain reaction conditions may include, for example, a particular temperature or a range of temperatures determined by experimental optimization to permit an allele discriminating probe to discriminate between a target and a target-like sequence with at least a single nucleotide difference.

In one embodiment of the invention, an allele discriminating probe according to the invention preferably comprises a target nucleic acid binding sequence from 6 to 50 and preferably from 7 to 25 nucleotides, and complementary nucleic acid sequences from 3 to 8 nucleotides. The guanosine-cytidine content of the secondary structure and probe-target hybrids, salt, and assay temperature should all be considered, for example magnesium salts have a strong stabilizing effect that is particularly important to consider when designing short, allele-discriminating probes.

If an allele-discriminating probe is to have a target nucleic acid binding sequence of about 50 nucleotides long, the sequence should be designed such that a single nucleotide mismatch to be discriminated against occurs at or near the middle of the target nucleic acid complementary sequence. For example, probes comprising a sequence that is 21 nucleotides long should preferably be designed so that the mismatch occurs opposite one of the 14 most centrally located nucleotides of the target nucleic acid complementary sequence and most preferably opposite one of the 7 most centrally located nucleotides. Designing a probe so that the mismatch to be discriminated against occurs in or near the middle of the target nucleic acid binding sequence/target-like nucleic acid binding sequence is believed to improve the performance of an allele-discriminating probe.

As used herein a "nuclease" or a "cleavage agent" refers to an enzyme that is specific for, that is, cleaves a cleavage structure according to the invention and is not specific for, that is, does not substantially cleave either a probe or a primer that is not hybridized to a target nucleic acid, or a target nucleic acid that is not hybridized to a probe or a primer. The term "nuclease" includes an enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), and *Thermus flavus* (Tfl). The term nuclease also embodies FEN nucleases. The term "FEN nuclease" encompasses an enzyme that possesses 5' exonuclease and/or an endonuclease activity. The term "FEN nuclease" also embodies a 5' flap-specific nuclease. A nuclease or cleavage agent according to the invention includes but is not limited to a FEN nuclease enzyme derived from *Archaeglobus fulgidus*, *Methanococcus jannaschii*, *Pyrococcus furiosus*, human, mouse or *Xenopus laevis*. A nuclease according to the invention also includes *Saccharomyces cerevisiae* RAD27, and *Schizosaccharomyces pombe* RAD2, Pol I DNA polymerase associated 5' to 3' exonuclease domain, (e.g. *E. coli*, *Thermus aquaticus* (Taq), *Thermus flavus* (Tfl), *Bacillus caldotenax* (Bca), *Streptococcus pneumoniae*) and phage functional homologs of FEN including but not limited to T5 5' to 3' exonuclease, T7 gene 6 exonuclease and T3 gene 6 exonuclease. Preferably, only the 5' to 3' exonuclease domains of Taq, Tfl and Bca FEN nuclease are used. The term "nuclease" does not include RNAse H.

As used herein, "captured" as it refers to capture of a binding moiety by a capture element or capture of a tag by a capture element, means specifically bound by hydrogen bonding, covalent bonding, or via an interaction between, for example a protein and a ligand, an antibody and an antigen, protein subunits, a nucleic acid binding protein and a nucleic acid binding site, or between complementary nucleic acids, wherein one member of the interacting pair is attached to a solid support. Under conditions of stable capture, binding results in the formation of a heterodimer with a dissociation constant ($K_D$) of at least about $1\times10^3$ M$^{-1}$, usually at least $1\times10^4$ M$^{-1}$, typically at least $1\times10^5$ M$^{-1}$, preferably at least $1\times10^6$ M$^{-1}$ to $1\times10^7$ M$^{-1}$ or more, under suitable conditions. Methods of performing binding reactions between a capture element, as defined herein, and a binding moiety or tag, as defined herein, are well-known in the art and are described hereinbelow. Methods of attaching a capture element according to the invention to a solid support, as defined herein, are well known in the art and are defined hereinbelow.

As used herein, "wild type" refers to a gene or gene product which has the characteristics of (i.e., either has the sequence of or encodes, for the gene, or possesses the sequence or activity of, for an enzyme) that gene or gene product when isolated from a naturally occurring source.

A "5' flap-specific nuclease" (also referred to herein as a "flap-specific nuclease") according to the invention is an endonuclease which can remove a single stranded flap that protrudes as a 5' single strand. In one embodiment of the invention, a flap-specific nuclease according to the invention can also cleave a pseudo-Y structure. A substrate of a flap-specific nuclease according to the invention, comprises a target nucleic acid and an oligonucleotide probe, as defined herein, that comprises a region or regions that are complementary to the target nucleic acid. In another embodiment, a substrate of a flap-specific nuclease according to the invention comprises a target nucleic acid, an upstream oligonucleotide that is complementary to the target nucleic acid and a downstream probe, according to the invention, that comprises a region or regions that are complementary to the target nucleic acid. In one embodiment, the upstream oligonucleotide and the downstream probe hybridize to non-overlapping regions of the target nucleic acid. In another embodiment the upstream oligonucleotide and the downstream probe hybridize to adjacent regions of the target nucleic acid.

As used herein, "adjacent" refers to separated by less than 20 nucleotides, e.g., 15 nucleotides, 10 nucleotides, 5 nucleotides, or 0 nucleotides.

A substrate of a flap-specific nuclease according to the invention, also comprises a target nucleic acid, a second nucleic acid, a portion of which specifically hybridizes with a target nucleic acid, and a primer extension product from a third nucleic acid that specifically hybridizes with a target nucleic acid.

As used herein, a "cleavage structure" refers to a polynucleotide structure (for example as illustrated in FIG. 1) comprising at least a duplex nucleic acid having a single stranded region comprising a flap, a loop, a single-stranded bubble, a D-loop, a nick or a gap. A cleavage structure according to the invention thus includes a polynucleotide structure comprising a flap strand of a branched DNA wherein a 5' single-stranded polynucleotide flap extends from a position near its junction to the double stranded portion of the structure and preferably the flap is labeled with a detectable label. A flap of a cleavage structure according to the invention is preferably about 1-10,000 nucleotides, more preferably about 5-25 nucleotides and most preferably about 10-20 nucleotides and is preferably cleaved at a position located at the phosphate positioned at the "elbow" of the branched structure or at any of one to ten phosphates located proximal and/or distal from the elbow of the flap strand. As used herein, "elbow" refers to the phosphate bond between the first single stranded nucleotide of the 5' flap and the first double stranded (e.g., hybridized to the target nucleic acid) nucleotide. In one embodiment, a flap of a cleavage structure cannot hybridize to a target nucleic acid.

A cleavage structure according to one embodiment of the invention preferably comprises a target nucleic acid, and also may include an oligonucleotide probe according to the invention, that specifically hybridizes with the target nucleic acid via a region or regions that are complementary to the target nucleic acid, and a flap extending from the hybridizing oligonucleotide probe. In another embodiment of the invention, a cleavage structure comprises a target nucleic acid (for example B in FIG. 4), an upstream oligonucleotide that is complementary to the target sequence (for example A in FIG. 4), and a downstream oligonucleotide probe according to the invention and comprising a region or regions, that are complementary to the target sequence (for example C in FIG. 4). In one embodiment, the upstream oligonucleotide and the downstream probe hybridize to non-overlapping regions of the target nucleic acid. In another embodiment, the upstream oligonucleotide and the downstream probe hybridize to adjacent regions of the target nucleic acid.

A cleavage structure according to the invention may be a polynucleotide structure comprising a flap extending from the downstream oligonucleotide probe of the invention, wherein the flap is formed by extension of the upstream oligonucleotide by the synthetic activity of a nucleic acid polymerase, and subsequent, partial, displacement of the 5' end of the downstream oligonucleotide. In such a cleavage structure, the downstream oligonucleotide may be blocked at the 3' terminus to prevent extension of the 3' end of the downstream oligonucleotide.

A cleavage structure according to one embodiment of the invention may be formed by hybridizing a target nucleic acid with an oligonucleotide probe wherein the oligonucleotide probe has a secondary structure that changes upon binding of the probe to the target nucleic acid, and further comprises a binding moiety and a complementary region that anneals to the target nucleic acid, and a non-complementary region that does not anneal to the target nucleic acid and forms a 5' flap.

A cleavage structure also may be a pseudo-Y structure wherein a pseudoY-structure is formed if the strand upstream of a flap (referred to herein as a flap adjacent strand or primer strand) is not present, and double stranded DNA substrates containing a gap or nick. A "cleavage structure", as used herein, does not include a double stranded nucleic acid structure with only a 3' single-stranded flap. As used herein, a "cleavage structure" comprises ribonucleotides or deoxyribonucleotides and thus can be RNA or DNA.

A cleavage structure according to the invention may be an overlapping flap wherein the 3' end of an upstream oligonucleotide capable of hybridizing to a target nucleic acid (for example A in FIG. 4) is identical to 1 base pair of the downstream oligonucleotide probe of the invention (for example C in FIG. 4) that is annealed to a target nucleic acid and wherein the overlap is directly downstream of the point of extension of the single stranded flap.

A cleavage structure according to one embodiment of the invention is formed by the steps of 1. incubating a) an upstream 3' end, preferably an oligonucleotide primer, b) an oligonucleotide probe located not more than 10,000 nucleotides downstream of the upstream primer and having a secondary structure that changes upon binding of the probe to the target nucleic acid and further comprising a binding moiety c) an appropriate target nucleic acid wherein the target sequence is at least partially complementary to both the upstream primer and downstream probe and d) a suitable buffer, under conditions that allow the nucleic acid sequence to hybridize to the oligonucleotide primers, and, in one embodiment of the invention, 2. extending the 3' end of the upstream oligonucleotide primer by the synthetic activity of a polymerase such that the newly synthesized 3' end of the upstream oligonucleotide primer becomes adjacent to and/or displaces at least a portion of (i.e., at least 1-10 nucleotides of) the 5' end of the downstream oligonucleotide probe. According to the method of the invention, buffers and extension temperatures are favorable for strand displacement by a particular nucleic acid polymerase according to the invention. Preferably, the downstream oligonucleotide is blocked at the 3' terminus to prevent extension of the 3' end of the downstream oligonucleotide.

In another embodiment of the invention, a cleavage structure according to the invention can be prepared by incubating a target nucleic acid with an oligonucleotide probe having a secondary structure that changes upon binding of the probe to the target nucleic acid, and further comprising a binding moiety and a non-complementary 5' region that does not anneal to the target nucleic acid and forms a 5' flap, and a complementary 3' region that anneals to the target nucleic acid.

In another embodiment of the invention, a cleavage structure according to the invention can be prepared by incubating a target nucleic acid with a downstream oligonucleotide probe having a secondary structure that changes upon binding of the probe to the target nucleic acid, and further comprising a binding moiety and a non-complementary 5' region that does not anneal to the target nucleic acid and forms a 5' flap and a complementary 3' region that anneals to the target nucleic acid, and an upstream oligonucleotide primer. In one embodiment, the upstream oligonucleotide and the downstream probe hybridize to non-overlapping regions of the target nucleic acid. In another embodiment, the upstream oligonucleotide and the downstream probe hybridize to adjacent regions of the target nucleic acid.

In a preferred embodiment of the invention a cleavage structure is labeled. A labeled cleavage structure according to one embodiment of the invention is formed by the steps of 1. incubating a) an upstream extendable 3' end, for example, an oligonucleotide primer, b) a labeled probe having a secondary structure that changes upon binding of the probe to the target nucleic acid, and further comprising a binding moiety, preferably located not more than 10,000 and more preferably located not more than 500 nucleotides downstream of the upstream primer and c) an appropriate target nucleic acid wherein the target sequence is complementary to both the primer and the labeled probe and d) a suitable buffer, under conditions that allow the nucleic acid sequence to hybridize to the primers, and, in one embodiment of the invention, 2. extending the 3' end of the upstream primer by the synthetic activity of a polymerase such that the newly synthesized 3' end of the upstream primer partially displaces the 5' end of the downstream probe. According to the method of the invention, buffers and extension temperatures are favorable for strand displacement by a particular nucleic acid polymerase according to the invention. Preferably, the downstream oligonucleotide is blocked at the 3' terminus to prevent extension of the 3' end of the downstream oligonucleotide. In one embodiment, the upstream primer and the downstream probe hybridize to non-overlapping regions of the target nucleic acid.

In another embodiment, a cleavage structure according to the invention can be prepared by incubating a target nucleic acid with a probe having a secondary structure that changes upon binding of the probe to the target nucleic acid, and further comprising a binding moiety and a non-complementary, labeled, 5' region that does not anneal to the target nucleic acid and forms a 5' flap, and a complementary 3' region that anneals to the target nucleic acid. In another embodiment, a cleavage structure according to the invention can be prepared by incubating a target nucleic acid with a downstream probe having a secondary structure that changes upon binding of the probe to the target nucleic acid, and further comprising a binding moiety and a non-complementary, labeled, 5' region that does not anneal to the target nucleic acid and forms a 5' flap and a complementary 3'region that anneals to the target nucleic acid, and an upstream oligonucleotide primer. In one embodiment, the upstream oligonucleotide and the downstream probe hybridize to non-overlapping regions of the target nucleic acid. In another embodiment, the upstream oligonucleotide and the downstream probe hybridize to adjacent regions of the target nucleic acid.

As used herein, "generating a signal" refers to detecting and or measuring a released nucleic acid fragment that is released from the cleavage structure and is captured by binding of a binding moiety to a capture element on a solid support, as an indication of the presence of a target nucleic acid in a sample.

As used herein, "sample" refers to any substance containing or presumed to contain a nucleic acid of interest (a target nucleic acid) or which is itself a nucleic acid containing or presumed to contain a target nucleic acid of interest. The term "sample" thus includes a sample of nucleic acid (genomic DNA, cDNA, RNA), cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

As used herein, "target nucleic acid" or "template nucleic acid sequence" refers to a region of a nucleic acid that is to be either replicated, amplified, and/or detected. In one embodiment, the "target nucleic acid" or "template nucleic acid sequence" resides between two primer sequences used for amplification.

As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyzing intervening, annealed probe to release both labeled and unlabeled probe fragments, until synthesis terminates. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

As used herein, "5' to 3' exonuclease activity" or "5'→3' exonuclease activity" refers to that activity of a template-specific nucleic acid polymerase e.g. a 5'→3' exonuclease activity traditionally associated with some DNA polymerases whereby mononucleotides or oligonucleotides are removed from the 5' end of a polynucleotide in a sequential manner, (i.e., *E. coli* DNA polymerase I has this activity whereas the Klenow (Klenow et al., 1970, *Proc. Natl. Acad. Sci., USA*, 65:168) fragment does not, (Klenow et al., 1971, *Eur. J. Biochem.*, 22:371)), or polynucleotides are removed from the 5' end by an endonucleolytic activity that may be inherently present in a 5' to 3' exonuclease activity.

As used herein, the phrase "substantially lacks 5' to 3' exonuclease activity" or "substantially lacks 5'→3' exonuclease activity" means having less than 10%, 5%, 1%, 0.5%, or 0.1% of the activity of a wild type enzyme. The phrase "lacking 5' to 3' exonuclease activity" or "lacking 5'→3' exonuclease activity" means having undetectable 5' to 3' exonuclease activity or having less than about 1%, 0.5%, or 0.1% of the 5' to 3' exonuclease activity of a wild type enzyme.

To detect structure-specific endonucleolytic activity, a DNA template consisting of a flap structure, wherein the downstream flap oligonucleotide is radiolabeled at the 5' end is employed. The reaction is carried out with DNA polymerase in the presence of dNTPs (to extend the upstream primer). Radiolabeled cleavage products are visualized by gel electrophoresis (Lyamichev et al., 1993, Science 260: 778).

Alternatively, the 5'-3' exonuclease activity of a DNA polymerase is assayed using uniformly-labeled double-stranded DNA that is also nicked. The release of radioactivity (TCA soluble cpms) by a DNA polymerase in the absence and presence of dNTPs is measured. Non-proofreading DNA polymerases with 5'-3' exonuclease activity are stimulated 10-fold or more by concomitant polymerization that occurs in the presence of dNTPs (increase in cpms released in the presence of dNTPs). Proofreading DNA polymerases with 3'-5' exo activity are inhibited completely by concomitant polymerization that occurs in the presence of dNTPs (decrease in cpms released in the presence of dNTPs) (U.S. Pat. No. 5,352,778).

Nucleases useful according to the invention include any enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), and *Thermus flavus* (Tfl). Nucleases useful according to the invention also include DNA polymerases with 5'-3' exonuclease activity, including but not limited to eubacterial DNA polymerase I, including enzymes derived from *Thermus* species (Taq, Tfl, Tth, Tca (*caldophilus*) Tbr (*brockianus*)), enzymes derived from *Bacillus* species (Bst, Bca, Magenta (full length polymerases, NOT N-truncated versions)), enzymes derived from *Thermotoga* species (Tma (*maritima*, Tne (*neopolitana*)) and *E. coli* DNA polymerase I. The term nuclease also embodies FEN nucleases. Additional nucleic acid polymerases useful according to the invention are included below in the section entitled, "Nucleic Acid Polymerases"

As used herein, "cleaving" refers to enzymatically separating a cleavage structure into distinct (i.e. not physically linked to other fragments or nucleic acids by phosphodiester bonds) fragments or nucleotides and fragments that are released from the cleavage structure. For example, cleaving a labeled cleavage structure refers to separating a labeled cleavage structure according to the invention and defined below, into distinct fragments including fragments derived from an oligonucleotide that specifically hybridizes with a target nucleic acid or wherein one of the distinct fragments is a labeled nucleic acid fragment derived from a target nucleic acid and/or derived from an oligonucleotide that specifically hybridizes with a target nucleic acid that can be detected and/or measured by methods well known in the art and described herein that are suitable for detecting the labeled moiety that is present on a labeled fragment.

As used herein, "endonuclease" refers to an enzyme that cleaves bonds, preferably phosphodiester bonds, within a nucleic acid molecule. An endonuclease according to the invention can be specific for single-stranded or double-stranded DNA or RNA.

As used herein, "exonuclease" refers to an enzyme that cleaves bonds, preferably phosphodiester bonds, between nucleotides one at a time from the end of a polynucleotide. An exonuclease according to the invention can be specific for the 5' or 3' end of a DNA or RNA molecule, and is referred to herein as a 5' exonuclease or a 3' exonuclease.

As used herein a "flap" refers to a region of single stranded DNA that extends from a double stranded nucleic acid molecule. A flap according to the invention is preferably between about 1-10,000 nucleotides, more preferably between about 5-25 nucleotides and most preferably between about 10-20 nucleotides.

In a preferred embodiment, the binding moiety is a tag.

In another preferred embodiment, the binding moiety is a nucleic acid sequence that binds to a capture element.

The invention also provides a method of detecting or measuring a target nucleic acid comprising the steps of: forming a cleavage structure by incubating a sample containing a target nucleic acid with a probe having a secondary structure that changes upon binding of the probe to the target nucleic acid and, the probe further comprising a binding moiety, cleaving the cleavage structure with a nuclease to release a nucleic acid fragment wherein the cleavage is performed at a cleaving temperature, and the secondary structure of the probe when not bound to the target nucleic acid is stable at or below the cleaving temperature; and detecting and/or measuring the amount of the fragment captured by binding of the binding moiety to a capture element on a solid support as an indication of the presence of the target sequence in the sample.

As used herein, "detecting a target nucleic acid" or "measuring a target nucleic acid" refers to determining the presence of a particular target nucleic acid in a sample or determining the amount of a particular target nucleic acid in a sample as an indication of the presence of a target nucleic acid in a sample. The amount of a target nucleic acid that can be measured or detected is preferably about 1 molecule to $10^{20}$ molecules, more preferably about 100 molecules to $10^{17}$ molecules and most preferably about 1000 molecules to $10^{14}$ molecules. According to one embodiment of the invention, the detected nucleic acid is derived from the labeled 5' end of a downstream probe of a cleavage structure according to the invention (for example C in FIG. 4), that is displaced from the target nucleic acid by the 3' extension of an upstream probe of a cleavage structure according to the invention (for example A of FIG. 4). According to the present invention, a label is attached to the 5' end of the downstream probe (for example C in FIG. 4) comprising a cleavage structure according to the invention. Alternatively, a label is attached to the 3' end of the downstream probe and a quencher is attached to the 5' flap of the downstream probe. According to the invention, a label may be attached to the 3' end of the downstream probe (for example C in FIG. 4) comprising a cleavage structure according to the invention.

According to the invention, the downstream probe (for example C in FIG. 4) may be labeled internally. In a preferred embodiment, a cleavage structure according to the invention can be prepared by incubating a target nucleic acid with a probe having a secondary structure that changes upon binding of the probe to the target nucleic acid, and further comprising a non-complementary, labeled, 5' region that does not anneal to the target nucleic acid and forms a 5' flap, and a complementary 3' region that anneals to the target nucleic acid. According to this embodiment of the invention, the detected nucleic acid is derived from the labeled 5' flap region of the probe. Preferably there is a direct correlation between the amount of the target nucleic acid and the signal generated by the cleaved, detected nucleic acid.

In another embodiment, the probe is labeled with a pair of interactive labels (e.g., a FRET or non-FRET pair) positioned to permit the separation of the labels during oligonucleotide probe unfolding (e.g., for example due to a change in the secondary structure of the probe) or hydrolysis. As used herein, "detecting the amount of the fragment captured by a capture element on a solid support" or "measuring the amount of the fragment captured by a capture element on a solid support" or "detecting the amount of the fragment captured by a capture element on a solid support" or "measuring the amount of the fragment captured by a capture element on a solid support" refers to determining the presence of a labeled or unlabeled fragment in a sample or determining the amount of a labeled or unlabeled fragment in a sample. Methods well known in the art and described herein can be used to detect or measure release of labeled or unlabeled fragments bound to a capture element on a solid support, or following the release of the labeled or unlabeled fragment from a capture element on a solid support. The detection methods described herein are operative for detecting a fragment wherein any amount of a fragment is detected whether that be a small or large proportion of the fragments generated in the reaction. A method of detecting or measuring release of labeled fragments will be appropriate for measuring or detecting the labeled moiety that is present on the labeled fragments bound to a capture element on a solid support. Methods of detecting or measuring release of unlabeled fragments include, for example, gel electrophoresis or by hybridization, according to methods well known in the art. The detection methods described herein are operative when as little as 1 or 2 molecules (and up to 1 or 2 million, for example 10, 100, 1000, 10,000, 1 million) of released fragment are detected.

As used herein, "labeled fragments" refer to cleaved mononucleotides or small oligonucleotides or oligonucleotides derived from the labeled cleavage structure according to the invention wherein the cleaved oligonucleotides are preferably between about 1-1000 nucleotides, more preferably between about 5-50 nucleotides and most preferably between about 16-18 nucleotides, which are cleaved from a cleavage structure by a nuclease and can be detected by methods well known in the art and described herein.

In one embodiment, a probe is a bi-molecular or multimolecular probe wherein a first molecule comprising the probe is labeled with a fluorophore and a second molecule comprising the probe is labeled with a quencher. As used herein, a "subprobe" and "subquencher" refer to a first molecule of a bi- or multi-molecular probe according to the invention, that is labeled with a fluorophore and a second molecule of a bi- or multi-molecular probe according to the invention, that is labeled with a quencher, respectively. According to this embodiment, following binding of the bi- or multi-molecular probe to the target nucleic acid, and cleavage by a nuclease, the subprobe and subquencher dissociate from each other (that is, the distance between the subprobe and the subquencher increases) and a signal is generated as a result of this dissociation and subsequent separation of the subprobe and subquencher.

In a preferred embodiment, the binding moiety is a tag.

In another preferred embodiment, the binding moiety is a nucleic acid sequence that binds to a capture element.

In a preferred embodiment, the method further comprises a nucleic acid polymerase.

In another preferred embodiment, the cleavage structure further comprises a 5' flap.

In another preferred embodiment, the cleavage structure further comprises an oligonucleotide primer.

In another preferred embodiment, the secondary structure is selected from the group consisting a stem-loop structure, a hairpin structure, an internal loop, a bulge loop, a branched structure, a pseudoknot structure or a cloverleaf structure.

In another preferred embodiment, the nuclease is a FEN nuclease.

In another preferred embodiment the FEN nuclease is selected from the group consisting of FEN nuclease enzyme derived from *Archaeglobus fulgidus, Methanococcus jannaschii, Pyrococcus furiosus*, human, mouse or *Xenopus laevis*. A FEN nuclease according to the invention also includes *Saccharomyces cerevisiae* RAD27, and *Schizosaccharomyces pombe* RAD2, Pol I DNA polymerase associated 5' to 3' exonuclease domain, (e.g. *E. coli, Thermus aquaticus* (Taq), *Thermus flavus* (Tfl), *Bacillus caldotenax* (Bca), *Streptococcus pneumoniae*) and phage functional homologs of FEN including but not limited to T4, T5 5' to 3' exonuclease, T7 gene 6 exonuclease and T3 gene 6 exonuclease.

Preferably, only the 5' to 3' exonuclease domains of Taq, Tfl and Bca FEN nuclease are used.

In another preferred embodiment, the probe further comprises a reporter.

In another preferred embodiment, the reporter comprises a tag.

In another preferred embodiment, the fragment is captured by binding of the tag to a capture element.

In another preferred embodiment, the cleavage structure is formed comprising at least one labeled moiety capable of providing a signal.

In another preferred embodiment, the cleavage structure is formed comprising a pair of interactive signal generating labeled moieties effectively positioned on the probe to quench the generation of a detectable signal when the probe is not bound to the target nucleic acid.

In another preferred embodiment, the labeled moieties are separated by a site susceptible to nuclease cleavage, thereby allowing the nuclease activity of the nuclease to separate the first interactive signal generating labeled moiety from the second interactive signal generating labeled moiety by cleaving at the site susceptible to nuclease cleavage, thereby generating a detectable signal.

The presence of a pair of interactive signal generating labeled moieties, as described above, allows for discrimination between annealed, uncleaved probe that may bind to a capture element, and released labeled fragment that is bound to a capture element.

In another preferred embodiment, the pair of interactive signal generating moieties comprises a quencher moiety and a fluorescent moiety.

The invention also provides for a polymerase chain reaction process for detecting a target nucleic acid in a sample. This process comprises, providing a cleavage structure comprising a probe having a secondary structure that changes upon binding of the probe to the target nucleic acid and, the probe further comprising a binding moiety, a set of oligonucleotide primers wherein a first primer contains a sequence complementary to a region in one strand of the target nucleic acid and primes the synthesis of a complementary DNA strand, and a second primer contains a sequence complementary to a region in a second strand of the target nucleic acid and primes the synthesis of a complementary DNA strand. This process also comprises amplifying the target nucleic acid employing a nucleic acid polymerase as a template-dependent polymerizing agent under conditions which are permissive for PCR cycling steps of (i) annealing of primers required for amplification to a template nucleic acid sequence contained within the target nucleic acid, (ii) extending the primers providing that the nucleic acid polymerase synthesizes a primer extension product, and (iii) cleaving the cleavage structure employing a nuclease as a cleavage agent for release of labeled fragments from the cleavage structure thereby creating detectable labeled fragments. According to this process, the cleaving is performed at a cleaving temperature and the secondary structure of the second primer when not bound to the target nucleic acid is stable at or below the cleaving temperature. The amount of released, labeled fragment captured by binding of the binding moiety to a capture element on a solid support is detected and/or measured as an indicator of the presence of the target sequence in the sample.

As used herein, an "oligonucleotide primer" refers to a single stranded DNA or RNA molecule that is hybridizable to a nucleic acid template and primes enzymatic synthesis of a second nucleic acid strand. Oligonucleotide primers useful according to the invention are between about 6 to 100 nucleotides in length, preferably about 17-50 nucleotides in length and more preferably about 1745 nucleotides in length. Oligonucleotide probes useful for the formation of a cleavage structure according to the invention are between about 17-40 nucleotides in length, preferably about 17-30 nucleotides in length and more preferably about 17-25 nucleotides in length.

As used herein, "template dependent polymerizing agent" refers to an enzyme capable of extending an oligonucleotide primer in the presence of adequate amounts of the four deoxyribonucleoside triphosphates (dATP, dGTP, dCTP and dTTP) or analogs as described herein, in a reaction medium comprising appropriate salts, metal cations, appropriate stabilizers and a pH buffering system. Template dependent polymerizing agents are enzymes known to catalyze primer- and template-dependent DNA synthesis, and possess 5' to 3' nuclease activity. Preferably, a template dependent polymerizing agent according to the invention lacks 5' to 3' nuclease activity.

As used herein, "amplifying" refers to producing additional copies of a nucleic acid sequence, including the method of the polymerase chain reaction.

In a preferred embodiment, the nuclease is a FEN nuclease.

In a preferred embodiment, the binding moiety is a tag.

In another preferred embodiment, the binding moiety is a nucleic acid sequence that binds to a capture element.

In another preferred embodiment, the oligonucleotide primers of step b are oriented such that the forward primer is located upstream of the cleavage structure and the reverse primer is located downstream of the cleavage structure.

In another preferred embodiment, the nucleic acid polymerase has strand displacement activity.

Nucleic acid polymerases exhibiting strand displacement activity and useful according to the invention include but are not limited to archaeal DNA polymerases with "temperature activated" strand displacement activity (exo plus and exo minus versions of Vent, Deep Vent, Pfu, JDF-3, KOD (LTI's tradename Pfx), Pwo, 9 degrees North, *Thermococcus aggregans, Thermococcus gorgonarius*), and eubacterial DNA polymerases with strand displacement activity (exo minus Bst, exo minus Bca, Genta, Klenow fragment, exo minus Klenow fragment exo minus T7 DNA polymerase (Sequenase).

In another preferred embodiment, the nucleic acid polymerase is thermostable

In another preferred embodiment, the nuclease is thermostable.

As used herein, "thermostable" refers to an enzyme which is stable and active at temperatures as great as preferably between about 90-100° C. and more preferably between about 70-98° C. to heat as compared, for example, to a non-thermostable form of an enzyme with a similar activity. For example, a thermostable nucleic acid polymerase or FEN nuclease derived from thermophilic organisms such as *P. furiosus, M. jannaschii, A. fulgidus* or *P. horikoshii* are more stable and active at elevated temperatures as compared to a nucleic acid polymerase from *E. coli* or a mammalian FEN enzyme. A representative thermostable nucleic acid polymerase isolated from *Thermus aquaticus* (Taq) is described in U.S. Pat. No. 4,889,818 and a method for using it in conventional PCR is described in Saiki et al., 1988, *Science* 239:487. Another representative thermostable nucleic acid polymerase isolated from *P. furiosus* (Pfu) is described in Lundberg et al., 1991, *Gene*, 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis*, and *Methanothermus fervidus*.

Temperature stable polymerases and FEN nucleases are preferred in a thermocycling process wherein double stranded nucleic acids are denatured by exposure to a high temperature (about 95° C.) during the PCR cycle.

In another preferred embodiment, the nuclease is a flap-specific nuclease.

In another preferred embodiment, the probe further comprises a reporter.

In another preferred embodiment, the reporter comprises a tag.

In another preferred embodiment, the fragment is captured by binding of said tag to a capture element.

In another preferred embodiment, the cleavage structure is formed comprising at least one labeled moiety capable of providing a signal.

In another preferred embodiment, the cleavage structure is formed comprising a pair of interactive signal generating labeled moieties effectively positioned on the probe to quench the generation of a detectable signal when the probe is not bound to the target nucleic acid.

In another preferred embodiment, the labeled moieties are separated by a site susceptible to nuclease cleavage, thereby allowing the nuclease activity of the nuclease to separate the first interactive signal generating labeled moiety from the second interactive signal generating labeled moiety by cleaving at the site susceptible to nuclease cleavage, thereby generating a detectable signal.

In another preferred embodiment, the pair of interactive signal generating moieties comprises a quencher moiety and a fluorescent moiety.

In another preferred embodiment, the nucleic acid polymerase is selected from the group consisting of Taq polymerase and Pfu polymerase.

The invention provides for a polymerase chain reaction process wherein amplification and detection of a target nucleic acid occur concurrently (i.e., real time detection). The invention also provides for a polymerase chain reaction process wherein amplification of a target nucleic acid occurs prior to detection of the target nucleic acid (i.e., end point detection).

The invention also provides for a polymerase chain reaction process for simultaneously forming a cleavage structure, amplifying a target nucleic acid in a sample and cleaving the cleavage structure. This process comprises the step of: (a) providing an upstream oligonucleotide primer complementary to a first region in one strand of the target nucleic acid, a downstream labeled probe complementary to a second region in the same strand of the target nucleic acid, wherein the downstream labeled probe is capable of forming a secondary structure that changes upon binding of the probe to the target nucleic acid and, the probe further comprises a binding moiety, and a downstream oligonucleotide primer complementary to a region in a second strand of the target nucleic acid. According to this step of the process, the upstream primer primes the synthesis of a complementary DNA strand, and the downstream primer primes the synthesis of a complementary DNA strand. This process also comprises the step of (b) detecting a nucleic acid which is produced and captured by binding of the binding moiety to a capture element on a solid support. The nucleic acid that is detected is produced in a reaction comprising amplification and cleavage of the target nucleic acid wherein a nucleic acid polymerase is a template-dependent polymerizing agent under conditions which are permissive for PCR cycling steps of (i) annealing of primers to a target nucleic acid, (ii) extending the primers of step (a), providing that the nucleic acid polymerase synthesizes primer extension products, and the primer extension product of the upstream primer of step (a) partially displaces the downstream probe of step (a) to form a cleavage structure. The conditions are also permissive for (iii) cleaving the cleavage structure employing a nuclease as a cleavage agent for release of detectable labeled fragments from the cleavage structure. The cleaving is performed at a cleaving temperature and the secondary structure of the probe when not bound to the target nucleic acid is stable at or below the cleaving temperature.

In a preferred embodiment, the cleavage structure further comprises a 5' flap.

The invention also provides a method of forming a cleavage structure comprising the steps of: (a) providing a target nucleic acid, (b) providing an upstream primer complementary to the target nucleic acid, (c) providing a downstream probe having a secondary structure that changes upon binding of the probe to a target nucleic acid and, the probe further comprises a binding moiety; and (d) annealing the target nucleic acid, the upstream primer and the downstream probe. The cleavage structure can be cleaved with a nuclease at a cleaving temperature. The secondary structure of the probe when not bound to the target nucleic acid is stable at or below the cleaving temperature.

In a preferred embodiment, the cleavage structure comprises a 5' flap.

The invention also provides for a composition comprising a target nucleic acid, a probe having a secondary structure that changes upon binding of the probe to a target nucleic acid and, the probe further comprises a binding moiety, and a nuclease. The probe and the target nucleic acid of this composition can bind to form a cleavage structure that can be cleaved by the nuclease at a cleaving temperature. The secondary structure of the probe when not bound to the target nucleic acid is stable at or below the cleaving temperature.

In a preferred embodiment, the composition further comprises an oligonucleotide primer.

In another preferred embodiment, the probe and the oligonucleotide hybridize to non-overlapping regions of the target nucleic acid.

The invention also provides for a kit for generating a signal indicative of the presence of a target nucleic acid in a sample, comprising a probe having a secondary structure that changes upon binding of the probe to a target nucleic acid and, the probe further comprising a binding moiety, and a nuclease. The probe of this kit can bind to a target nucleic acid to form a cleavage structure that can be cleaved by the nuclease at a cleaving temperature. The secondary structure of the probe when not bound to the target nucleic acid is stable at or below the cleaving temperature.

In a preferred embodiment, the kit further comprises an oligonucleotide primer.

In another preferred embodiment, the nuclease is a FEN nuclease.

In another preferred embodiment, the probe comprises at least one labeled moiety.

In another preferred embodiment, the probe comprises a pair of interactive signal generating labeled moieties effectively positioned to quench the generation of a detectable signal when the probe is not bound to the target nucleic acid.

In another preferred embodiment, the labeled moieties are separated by a site susceptible to nuclease cleavage, thereby allowing the nuclease activity of the nuclease to separate the first interactive signal generating labeled moiety from the second interactive signal generating labeled moiety by cleaving at the site susceptible to nuclease cleavage, thereby generating a detectable signal.

In another preferred embodiment, the pair of interactive signal generating moieties comprises a quencher moiety and a fluorescent moiety.

Further features and advantages of the invention are as follows. The claimed invention provides a method of generating a signal to detect and/or measure a target nucleic acid wherein the generation of a signal is an indication of the presence of a target nucleic acid in a sample. The method of the claimed invention does not require multiple steps. The claimed invention also provides a PCR based method for detecting and/or measuring a target nucleic acid comprising generating a signal as an indication of the presence of a target nucleic acid. The claimed invention allows for simultaneous amplification and detection and/or measurement of a target nucleic acid. The claimed invention also provides a PCR based method for detecting and/or measuring a target nucleic acid comprising generating a signal in the absence of a nucleic acid polymerase that demonstrates 5' to 3' exonuclease activity.

Further features and advantages of the invention will become more fully apparent in the following description of the embodiments and drawings thereof, and from the claims.

BRIEF DESCRIPTION OF DRAWINGS

FIG. 3 demonstrates secondary structures.

DESCRIPTION

Figure 1:
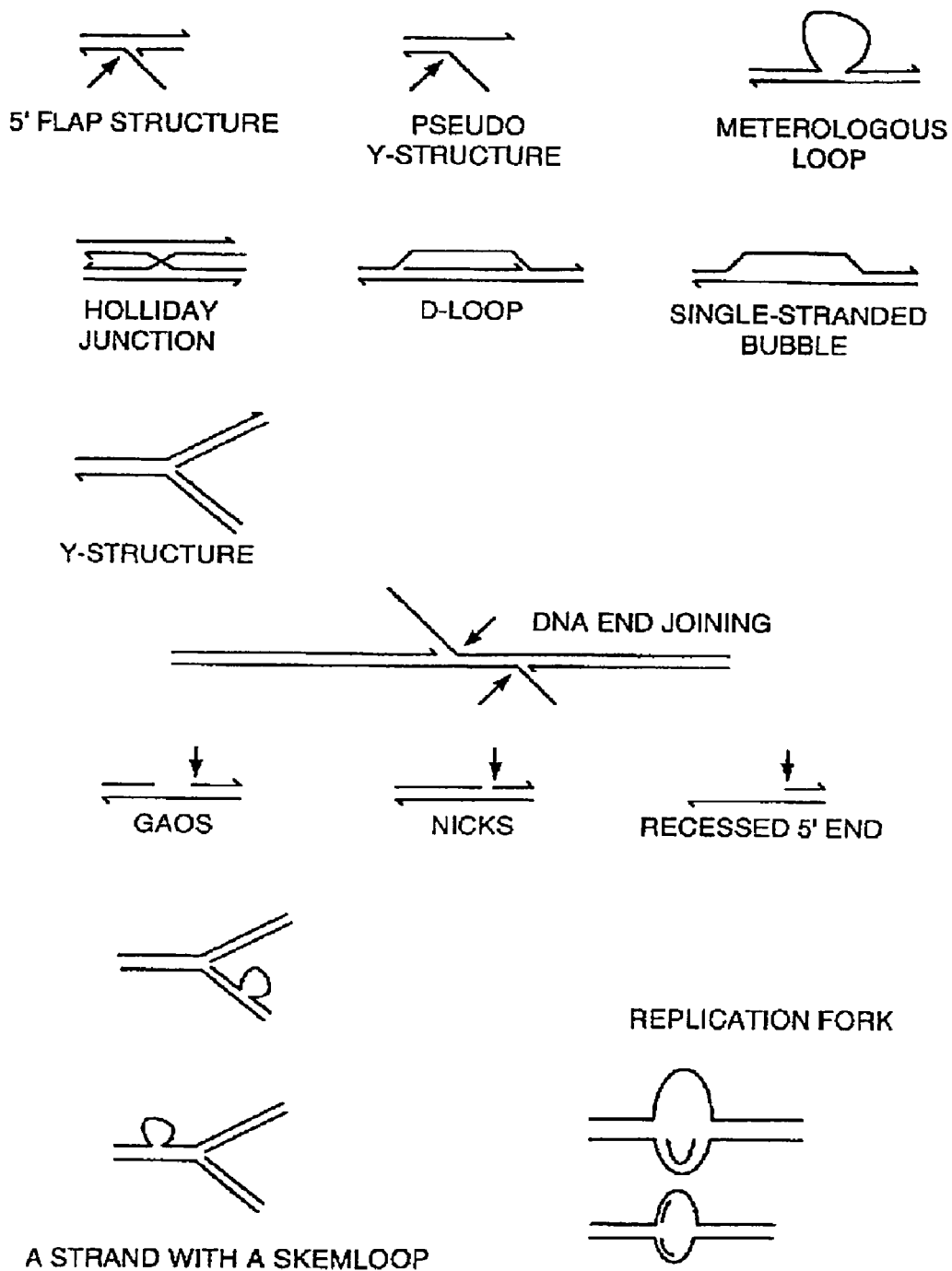
FIG. 1 demonstrates FEN nuclease cleavage structures.

The invention provides for a method of generating a signal to detect the presence of a target nucleic acid in a sample wherein a nucleic acid is treated with the combination of a probe having a secondary structure that changes upon binding of the probe to a target nucleic acid and comprising a binding moiety and a nuclease. The invention also provides for a process for detecting or measuring a nucleic acid that allows for concurrent amplification, cleavage and detection of a target nucleic acid in a sample.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference.

I. Nucleases

Nucleases useful according to the invention include any enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), and *Thermus flavus* (Tfl). Nucleases useful according to the invention also include DNA polymerases with 5'-3' exonuclease activity, including but not limited to eubacterial DNA polymerase I, including enzymes derived from *Thermus* species (Taq, Tfl, Tth, Tca (*caldophilus*) Tbr (*brockianus*)), enzymes derived from *Bacillus* species (Bst, Bca, Magenta (full length polymerases, NOT N-truncated versions)), enzymes derived from *Thermotoga* species (Tma (*maritima*, Tne (*neopolitana*)) and *E. coli* DNA polymerase I. The term nuclease also embodies FEN nucleases. A nuclease useful according to the invention can not cleave either a probe or primer that is not hybridized to a target nucleic acid or a target nucleic acid that is not hybridized to a probe or a primer.

FEN-1 is an ~40 kDa divalent metal ion-dependent exo- and endonuclease that specifically recognizes the backbone of a 5' single-stranded flap strand and tracks down this arm to the cleavage site, which is located at the junction wherein the two strands of duplex DNA adjoin the single-stranded arm. Both the endo- and exonucleolytic activities show little sensitivity to the base at the most 5' position at the flap or nick. Both FEN-1 endo- and exonucleolytic substrate binding and cutting are stimulated by an upstream oligonucleotide (flap adjacent strand or primer). This is also the case for *E. Coli* pol I. The endonuclease activity of the enzyme is independent of the 5' flap length, cleaving a 5' flap as small as one nucleotide. The endonuclease and exonuclease activities are insensitive to the chemical nature of the substrate, cleaving both DNA and RNA.

Both the endo- and exonucleolytic activities are inhibited by concentrations of salts in the physiological range. The exonuclease activity is inhibited 50-fold at 50 mM NaCl as compared to 0 mM NaCl. The endonuclease activity is inhibited only sevenfold at 50 mM NaCl (Reviewed in Lieber 1997, supra).

Although a 5'-OH terminus is a good substrate for FEN-1 loading onto a 5' flap substrate, it serves as a very poor substrate when part of a nick in an otherwise double stranded DNA structure. The electrostatic repulsion by the terminal phosphate is likely to favor breathing of the substrate into a pseudo-flap configuration, providing the active form of the substrate for FEN-1. Such an explanation would indicate a single active site and a single mechanism of loading of FEN-1 onto the 5' ssDNA terminus of the flap or pseudo-flap configuration of the nick. Consistent with this model are observations that optimal activity at a nick requires very low $Mg^{2-}$ and monovalent salt concentrations, which destabilize base-pairing and would favor breathing of a nick to a flap. Higher $Mg^{2+}$ and monovalent salt concentrations would disfavor breathing and inhibit cutting of nicked or gapped structures that do require breathing to convert to a flap. Cleavage of stable flap structures is optimal at moderate $Mg^{2+}$ levels and does not decrease with increasing $Mg^{2+}$ concentration. This is because a flap substrate does not have to melt out base pairs to achieve its structure; hence, it is entirely insensitive to $Mg^{2+}$. Though the endonucleolytic activity decreases with monovalent salt, the decline is not nearly as sharp as that seen for the exonucleolytic activity. Furthermore, it has previously been shown that one-nucleotide flaps are efficient substrates. All of these observations are consistent with the fact that when FEN-1 has been interpreted to be functioning as an exonuclease, the size of the degradation products vary from one to several nucleotides in length. Breathing of nicks into flaps of varying length would be expected to vary with local sequence, depending on the G/C content. In summary, a nick breathing to form a transient flap means that the exonucleolytic activity of FEN-1 is the same as the endonucleolytic activity (Reviewed in Lieber, 1997, supra).

The endonuclease and exonuclease activities of FEN-1 cleave both DNA and RNA without requiring accessory proteins. At the replication fork, however, FEN-1 does interact with other proteins, including a DNA helicase and the proliferating cell nuclear antigen (PCNA), the processivity factor for DNA polymerases δ and ε. PCNA significantly stimulates FEN-1 endo- and exonucleolytic activity.

The FEN-1 enzymes are functionally related to several smaller bacteriophage 5'→3' exonucleases such as T5 5' exonuclease and T4 RNase H as well as to the larger eukaryotic nucleotide excision repair enzymes such as XPG, which also acts in the transcription-coupled repair of oxidative base damage. In eubacteria such as *Escherichia coli* and *Thermus aquaticus*, Okazaki processing is provided by the PolI 5'→3' exonuclease domain. These bacterial and phage enzymes share two areas of limited sequence homology with FEN-1, which are termed the N(N-terminal) and I (intermediate) regions, with the residue similarities concentrated around seven conserved acidic residues. Based on crystal structures of T4 RNase H and T5 exonuclease as well as mutagenesis data, it has been proposed that these residues bind to two $Mg^{2+}$ ions that are required for affecting DNA hydrolysis; however, the role each metal plays in the catalytic cycle, which is subtly different for each enzyme, is not well understood (Reviewed in Hosfield et al., 1998b, supra).

fen-1 genes encoding FEN-1 enzymes useful in the invention include murine fen-1, human fen-1, rat fen-1, *Xenopus laevis* fen-1, and fen-1 genes derived from four archaebacteria *Archaeglobus fulgidus, Methanococcus jannaschii, Pyrococcus furiosus* and *Pyrococcus horikoshii*. cDNA clones encoding FEN-1 enzymes have been isolated from human (GenBank Accession Nos.: NM_004111 and L37374), mouse (GenBank Accession No.: L26320), rat (GenBank Accession No.: AA819793), *Xenopus laevis* (GenBank Accession Nos.: U68141 and U64563), and *P. furiosus* (GenBank Accession No.: AF013497). The complete nucleotide sequence for *P. horikoshii* flap endonuclease has also been determined (GenBank Accession No.: AB005215). The FEN-1 family also includes the *Saccharomyces cerevisiae* RAD27 gene (GenBank Accession No.: Z28113 Y13137) and the *Saccharomyces pombe* RAD2 gene (GenBank Accession No.: X77041). The archaeal genome of *Methanobacterium thermautotrophiculum* has also been sequenced. Although the sequence similarity between FEN-1 and prokaryotic and viral 5'→3' exonucleases is low, FEN-1s within the eukaryotic kingdom are highly conserved at the amino acid level, with the human and *S. cerevisiae* proteins being 60% identical and 78% similar. The three archaebacterial FEN-1 proteins are also, highly homologous to the eukaryotic FEN-1 enzymes (Reviewed in Matsui et al., 1999., *J. Biol. Chem.*, 274:18297, Hosfield et al., 1998b, *J. Biol. Chem.*, 273:27154 and Lieber, 1997, *BioEssays*, 19:233).

The sequence similarities in the two conserved nuclease domains (N-terminal or N and intermediate or I domains) between human and other FEN-1 family members are 92% (murine), 79% (*S. cerevisiae*), 77% (*S. pombe*), 72% (*A. fulgidus*), 76% (*M. jannaschii*), and 74% (*P. furiosus*).

FEN-1 specifically recognizes the backbone of a 5' single-stranded flap strand and migrates down this flap arm to the cleavage site located at the junction between the two strands of duplex DNA and the single-stranded arm. If the strand upstream of the flap (sometimes called the flap adjacent strand or primer strand) is removed, the resulting structure is termed a pseudo-Y (see FIG. 1). This structure is cleaved by FEN-1, but at 20- to 100-fold lower efficiency. FEN-1 does not cleave 3' single-stranded flaps. However, FEN-1 acting as an exonuclease will hydrolyze dsDNA substrates containing a gap or nick (Reviewed in Hosfield et al., 1998a, supra, Hosfield et al., 1999b, supra and Lieber 1997, supra). Exonucleolytically, FEN-1 acts at a nick and, with lower efficiency, at a gap or a recessed 5' end on dsDNA. At gapped structures, the efficiency of FEN-1 binding and cutting decreases with increasing gap size up to approximately five nucleotides and then stabilizes at a level of cleavage that is equivalent to activity on a recessed 5' end within dsDNA. Blunt dsDNA, recessed 3' ends and ssDNA are not cleaved (Reviewed in Lieber 1997, supra). The cleavage activity of FEN enzymes are described in Yoon et al., 1999, *Biochemistry*, 38: 4809; Rao, 1998, *J. Bacteriol.*, 180:5406 and Hosfield et al., 1998, *Cell*, 95:135-146, incorporated herein by reference.

FEN nucleases that are useful according to the invention have been isolated from a variety of organisms including human (GenBank Accession Nos.: NM_004111 and L37374), mouse (GenBank Accession No.: L26320), rat (GenBank Accession No.: AA819793), yeast (GenBank Accession No.: Z28113 Y13137 and GenBank Accession No.: X77041) and *xenopus laevis* (GenBank Accession Nos.: U68141 and U64563). Such enzymes can be cloned and overexpressed using conventional techniques well known in the art.

A FEN nuclease according to the invention is preferably thermostable. Thermostable FEN nucleases have been isolated and characterized from a variety of thermostable organisms including four archeaebacteria. The cDNA sequence (GenBank Accession No.: AF013497) and the amino acid sequence (Hosfield et al., 1998a, supra and Hosfield et al., 1998b) for *P. furiosus* flap endonuclease have been determined. The complete nucleotide sequence (GenBank Accession No.: AB005215) and the amino acid sequence (Matsui et al., supra) for *P. horikoshii* flap endonuclease have also been determined. The amino acid sequence for *M. jannaschii* (Hosfield et al., 1998b and Matsui et al., 1999 supra) and *A. fulgidus* (Hosfield et al., 1998b) flap endonuclease have also been determined.

Thermostable FEN1 enzymes can be cloned and overexpressed using techniques well known in the art and described in Hosfield et al., 1998a, supra, Hosfield et al., 1998b, Kaiser et al., 1999, J. Biol. Chem., 274: 21387 and Matusi et al., supra and herein in Example 2 entitled "Cloning Pfu FEN-1".

The endonuclease activity of a FEN enzyme can be measured by a variety of methods including the following.

A. Fen Endonuclease Activity Assay

Figure 2:
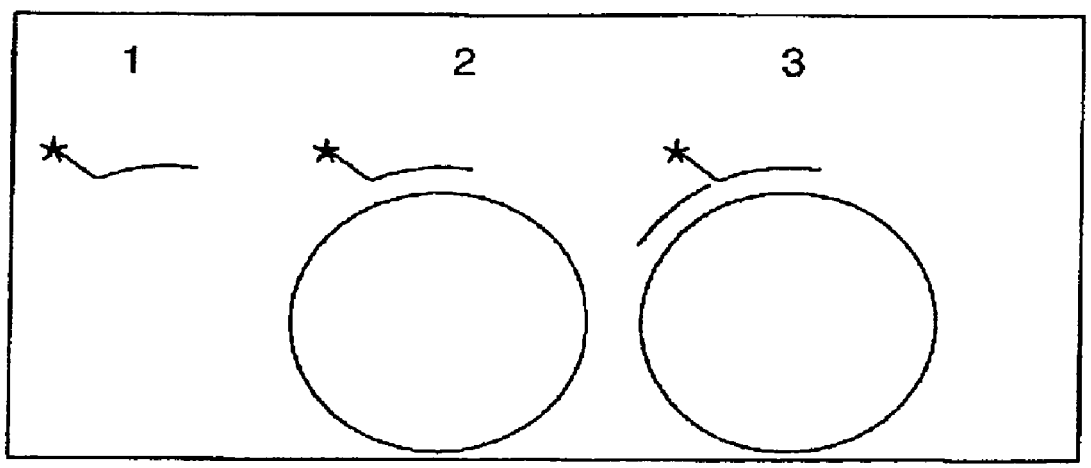
FIG. 2 demonstrates three templates (labeled 1, 2, and 3) that may be used to detect FEN nuclease activity.

1. Templates (for example as shown in FIG. 2) are used to evaluate the activity of a FEN nuclease according to the invention.

Template 1 is a 5' $^{33}$P labeled oligonucleotide (Heltest4) with the following sequence:

5'AAAATAAATAAAAAAAATACTGTTGGGAAGGGC-GATCGGTGCG 3'. The underlined section of Heltest4 represents the region complementary to M13mp18+. The cleavage product is an 18 nucleotide fragment with the sequence AAAATAAATAAAAAAAAT.

Heltest4 binds to M13 to produce a complementary double stranded domain as well as a non-complementary 5' overhang. This duplex forms template 2 (FIG. 2) which is also used for helicase assays. Template 3 (FIG. 2) has an additional primer (FENAS) bound to M13 and is directly adjacent to Heltest 4. The sequence of FENAS is: 5'CCATTCGCCAT-TCAGGCTGCGCA 3'. In the presence of template 3, FEN binds the free 5' terminus of Heltest4, migrates to the junction and cleaves Heltest4 to produce an 18 nucleotide fragment. Templates 1 and 2 serve as controls, although template 2 can also serve as a template.

Templates are prepared as described below:

|  | Template 1 | Template 2 | Template 3 |
|---|---|---|---|
| Heltest4 | 14 µl | 14 µl | 14 µl |
| M13 | ** | 14 µl | 14 µl |
| FENAS | ** | ** | 14 µl |
| H₂O | 28 µl | 14 µl | ** |
| 10x Pfu Buff. | 4.6 µl | 4.6 µl | 4.6 µl |

10×Pfu buffer is available from Stratagene (Catalog #200536). According to the method of the invention, 10×Pfu buffer is diluted such that a reaction is carried out in the presence of 1× buffer.

M13 is M13mp18+ strand and is at a concentration of 200 ng/µL, $^{33}$P labeled Heltest4 is at an approximate concentration of 0.7 ng/µl, and FENAS is at a concentration of 4.3 ng/µl. Based on these concentrations, the Heltest4 and M13 are at approximately equal molar amounts ($5\times10^{-14}$) and FENAS is present in an approximately 10× molar excess ($6\times10^{-13}$).

The template mixture is heated at 95° C. for five minutes, cooled to room temperature for 45 minutes and stored at 4° C. overnight.

2 µl of FEN-1 or, as a control, H₂O are mixed with the three templates as follows:

| 3 µl | template |
| 0.7 µl | 10x cloned Pfu buffer |
| 0.56 µl | 100 mM MgCl₂ |
| 2.00 µl | enzyme or H₂O |
| 0.74 µl | H₂0 |
| 7.00 µl | total volume |

The reactions are allowed to proceed for 30 minutes at 50° C. and stopped by the addition of 2 µl formamide "Sequencing Stop" solution to each sample. Samples are heated at 95° C. for five minutes and loaded on a 6% acrylamide, 7M urea CastAway (Stratagene) gel.

Alternatively, FEN activity can be analyzed in the following buffer wherein a one hour incubation time is utilized.

10×FEN Buffer 500 mM Tris-HCl pH 8.0

100 mM MgCl₂

The reaction mixture below is mixed with 2 µl of FEN or, as a control, 2 µl of H₂O.

| 3 µl | template |
| 0.7 µl | 10x FEN buffer |
| 2.00 µl | enzyme or H₂O |
| 1.3 µl | H₂O |
| 7.00 µl | total volume |

Samples are incubated for one hour at 50° C. in a Robocyler 96 hot top thermal cycler. Following the addition of 2 µl of Sequencing Stop dye solution, samples are heated at 99° C. for five minutes. Samples are loaded on an eleven-inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix (15% methanol, 5% acetic acid) and then for 10 minutes in water. The gel is placed on Whatmann 3 mm paper, covered with plastic wrap and dried for 2 hours in a heated vacuum gel dryer. The gel is exposed overnight to X-ray film.

2. FEN endonuclease activity can also be measured according to the method of Kaiser et al., supra). Briefly, reactions are carried out in a 10 µl volume containing 10 mM MOPS, pH 7.5, 0.05% Tween 20, 0.05% Nonidet P-40, 10 µg/ml tRNA, and 200 mM KCl for TaqPol and TthPol or 50 mM KCl for all other enzymes. Reaction conditions can be varied depending on the cleavage structure being analyzed. Substrates (2 µM) and varying amounts of enzyme are mixed with the indicated (above) reaction buffer and overlaid with Chill-out (MJ Research) liquid wax. Substrates are heat denatured at 90° C. for 20 s and cooled to 50° C., then reactions are started by addition of MgCl₂ or MnCl₂ and incubated at 50° C. for the specified length of time. Reactions are stopped by the addition of 10 µl of 95% formamide containing 10 mM EDTA and 0.02% methyl violet (Sigma). Samples are heated to 90° C. for 1 min immediately before electrophoresis on a 20% denaturing acrylamide gel (19:1 cross-linked), with 7M urea, and in a buffer of 45 mM Tris borate, pH 8.3, 1.4 mM EDTA. Unless otherwise indicated, 1 µl of each stopped reaction is loaded per lane. Gels are scanned on an FMBIO-100 fluorescent gel scanner (Hitachi) using a 505 nm filter. The fraction of cleaved product is determined from intensities of bands corresponding to uncut and cut substrate with FMBIO Analysis software (version 6.0, Hitachi). The fraction of cut product should not exceed 20% to ensure that measurements approximate initial cleavage rates. The cleavage rate is defined as the concentration of cut product divided by the enzyme concentration and the time of the reaction (in minutes). For each enzyme three data points are used to determine the rate and experimental error.

3. FEN endonuclease activity can also be measured according to the method of Hosfield et al., 1998a, supra. Briefly, in a final volume of 13 µl, varying amounts of FEN and 1.54 pmol of labeled cleavage substrate are incubated at different temperatures for 30 min before the reaction is quenched with an equal volume of stop solution (10 mM EDTA, 95% deionized formamide, and 0.008% bromophenol blue and xylene cyanol). Samples are electrophoresed through denaturing 15% polyacrylamide gels, and the relative amounts of starting material and product are quantitated using the IPLabGel system (Stratagene) running MacBAS image analysis software. Most reactions are performed in standard assay buffer (10 mM Tris-HCl (pH 8.0), 10 mM $MgCl_2$, and 50 µg/ml bovine serum albumin); however, in a series of experiments the effect of different divalent metals and pH levels are studied by varying the standard buffer. For divalent metals, $MgCl_2$ is omitted, and different metal ions are used at a final concentration of 10 mM. To study the influence of pH, buffers containing different amounts of Tris-HCl, glycine, and sodium acetate are used at a final concentration of 10 mM to obtain a wide range of pH levels at 25° C.

4. FEN endonuclease activity can also be measured according to the method of Matusi et al., 1999, supra. Briefly, the enzyme reactions are performed in a 15-µl reaction mixture containing 50 mM Tris-HCl (pH 7.4), 1.5 mM $MgCl_2$, 0.5 mM β-mercaptoethanol, 100 µg/ml bovine serum albumin, and 0.6 pmol of a labeled cleavage structure. After incubation for 30 min at 60° C., the reaction is terminated by adding 15 µl of 95% formamide containing 10 mM EDTA and 1 mg/ml bromophenol blue. The samples are heated at 95° C. for 10 min, loaded onto a 15% polyacrylamide gel (35 cm×42.5 cm) containing 7M urea and 10×TBE (89 mM Tris-HCl, 89 mM boric acid, 2 mM EDTA (pH 8.0)), and then electrophoresed for 2 h at 2000 V. Reaction products are visualized and quantified using a PhosphorImager (Bio-Rad). Size marker, oligonucleotides are 5' end-labeled with [γ-$^{32}$P]ATP and T4 polynucleotide kinase.

To determine the optimum pH, the reaction is performed in an assay mixture (15 µl) containing 1.5 mM $MgCl_2$, 0.5 mM β-mercaptoethanol, 100 µg/ml bovine serum albumin, and 0.6 pmol of 5' end-labeled cleavage structure in 50 mM of one of the following buffers at 60° C. for 30 min. Three different 50 mM buffers are used to obtain a wide pH range as follows: sodium acetate buffer (pH 4.0-5.5), phosphate buffer (pH 5.5-8.0), and borate buffer (pH 8.0-9.4).

B. FEN Exonuclease Activity Assay

The exonuclease activity of a FEN nuclease according to the invention can be measured by the method of measuring FEN-1 endonuclease activity described in Matsui et al., 1999, supra and summarized above.

Alternatively, the exonuclease activity of a FEN enzyme can be analyzed by the method described in Hosfield et al., 1998b, supra Briefly, exonuclease activities are assayed using a nicked substrate of FEN under conditions identical to those described for the endonuclease assays (described above).

The precise positions of DNA cleavage in both the exonuclease and endonuclease experiments can be obtained by partial digestion of a 5' $^{32}$P-labeled template strand using the 3'-5' exonuclease activity of Klenow fragment.

A cleavage structure according to one embodiment of the invention comprises a partially displaced 5' end of an oligonucleotide probe annealed to a target nucleic acid. Another cleavage structure according to the invention comprises a target nucleic acid (for example B in FIG. 4), an upstream oligonucleotide probe according to the invention, and comprising a region or regions that are complementary to the target sequence (for example A in FIG. 4), and a downstream oligonucleotide that is complementary to the target sequence (for example C in FIG. 4). A cleavage structure according to the invention can be formed by overlap between the upstream oligonucleotide and the downstream probe, or by extension of the upstream oligonucleotide by the synthetic activity of a nucleic acid polymerase, and subsequent partial displacement of the 5' end of the downstream oligonucleotide. A cleavage structure of this type is formed according to the method described in the section entitled "Cleavage Structure".

Alternatively, a cleavage structure according to the invention is formed by annealing a target nucleic acid to an oligonucleotide probe according to the invention wherein the oligonucleotide probe comprises a region or regions that are complementary to the target nucleic acid, and a non-complementary region that does not anneal to the target nucleic acid and forms a 5' flap. According to this embodiment, a cleavage structure comprises a 5' flap formed by a non-complementary region of the oligonucleotide.

A cleavage structure according to the invention also comprises an overlapping flap wherein the 3' end of an upstream oligonucleotide capable of annealing to a target nucleic acid (for example A in FIG. 4) is complementary to 1 (or more) base pair of the downstream oligonucleotide probe according to the invention (for example C in FIG. 4) that is annealed to a target nucleic acid and wherein the 1 (or more) base pair overlap is directly downstream of the point of extension of the single stranded flap and is formed according to method described in the section entitled "Cleavage Structure". In one embodiment, the upstream oligonucleotide and the downstream probe hybridize to non-overlapping regions of the target nucleic acid. In another embodiment, the upstream oligonucleotide and the downstream probe hybridize to adjacent regions of the target nucleic acid.

II. Nucleic Acid Polymerases

The invention provides for nucleic acid polymerases. Preferably, the nucleic acid polymerase according to the invention is thermostable.

Known DNA polymerases useful according to the invention include, for example, *E. coli* DNA polymerase I, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

Nucleic acid polymerases substantially lacking 5' to 3' exonuclease activity useful according to the invention include but are not limited to Klenow and Klenow exo-, and T7 DNA polymerase (Sequenase).

Thermostable nucleic acid polymerases substantially lacking 5' to 3' exonuclease activity useful according to the invention include but are not limited to Pfu, exo-Pfu (a mutant form of Pfu that lacks 3' to 5' exonuclease activity), the Stoffel fragment of Taq, N-truncated Bst, N-truncated Bca, Genta, JdF3 exo-, Vent, Vent exo- (a mutant form of Vent that lacks 3' to 5' exonuclease activity), Deep Vent, Deep Vent exo- (a mutant form of Deep Vent that lacks 3' to 5' exonuclease activity), U1Tma, and ThermoSequenase.

Nucleic acid polymerases useful according to the invention include both native polymerases as well as polymerase mutants, which lack 5' to 3' exonuclease activity. Nucleic acid polymerases useful according to the invention can possess different degrees of thermostability. Preferably, a nucleic acid polymerase according to the invention exhibits strand displacement activity at the temperature at which it can extend a nucleic acid primer. In a preferred embodiment of the invention, a nucleic acid polymerase lacks both 5' to 3' and 3' to 5' exonuclease activity.

Additional nucleic acid polymerases substantially lacking 5' to 3' exonuclease activity with different degrees of thermostability useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and φ29 DNA polymerase. The enzymes available commercially are: T4 (available from many sources e.g., Epicentre) and T7 (available from many sources, e.g. Epicentre for unmodified and USB for 3' to 5' exo⁻ T7 "Sequenase" DNA polymerase).

B. Archaeal DNA Polymerases:

There are 2 different classes of DNA polymerases which have been identified in archaea: 1. Family B/pol α type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol α or pol II) can be derived from archaea with optimal growth temperatures that are similar to the desired assay temperatures. Examples of suitable archaea include, but are not limited to:

1. Thermolabile (useful for 37° C. assays) —e.g., *Methanococcus voltae*

2. Thermostable (useful for non-PCR assays) —e.g., *Sulfolobus solfataricus, Sulfolobus acidocaldarium, Methanococcus jannaschii, Thermoplasma acidophilum*. It is estimated that suitable archaea exhibit maximal growth temperatures of ≦80-85° C. or optimal growth temperatures of ≦70-80° C.

3. Thermostable (useful for PCR assays) —e.g., *Pyrococcus* species (*furiosus*, species GB-D, species strain KOD1, *woesii, abysii, horikoshii*), *Thermococcus* species (*litoralis*, species 9° North-7, species JDF-3, *gorgonarius*), *Pyrodictium occultum*, and *Archaeoglobus fulgidus*. It is estimated that suitable archaea would exhibit maximal growth temperatures of ≧80-85° C. or optimal growth temperatures of ≧70-80° C. Appropriate PCR enzymes from the archaeal pol α DNA polymerase group are commercially available, including KOD (Toyobo), Pfx (Life Technologies, Inc.), Vent (New England BioLabs), Deep Vent (New England BioLabs), and Pwo (Boehringer-Mannheim).

Additional archaea related to those listed above are described in the following references: *Archaea: A Laboratory Manual* (Robb, F. T. and Place, A. R., eds.), Cold Spring Harbor Laboratory Press, Cold Spring Harbor, N.Y., 1995 and *Thermophilic Bacteria* (Kristjansson, J. K., ed.) CRC Press, Inc., Boca Raton, Fla., 1992.

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are no commercial sources of eubacterial pol II and pol III DNA polymerases. There are a variety of commercially available Pol I DNA polymerases, some of which have been modified to reduce or abolish 5' to 3' exonuclease activity. Methods used to eliminate 5' to 3' exonuclease activity of pol I DNA polymerases include:

mutagenesis (as described in Xu et al., 1997, *J. Mol. Biol.*, 268:284 and Kim et al., 1997, *Mol. Cells*, 7:468).

N-truncation by proteolytic digestion (as described in Klenow et al., 1971, *Eur. J. Biochem.*, 22: 371), or N-truncation by cloning and expressing as C-terminal fragments (as described in Lawyer et al., 1993, *PCR Methods Appl.*, 2:275).

As for archaeal sources, the assay-temperature requirements determine which eubacteria should be used as a source of a DNA polymerase useful according to the invention (e.g., mesophiles, thermophiles, hyperthermophiles).

1. Mesophilic/Thermolabile (Useful for 37° C. Assays)
   i. DNA polymerases naturally substantially lacking 5' to 3' exonuclease activity: pol II or the pol III catalytic subunit from mesophilic eubacteria, such as *Escherichia coli, Streptococcus pneumoniae, Haemophilus influenza, Mycobacterium* species (*tuberculosis, leprae*)
   ii. DNA polymerase mutants substantially lacking 5' to 3' exonuclease activity: Pol I DNA polymerases for N-truncation or mutagenesis can be isolated from the mesophilic eubacteria listed above (Ci). A commercially-available eubacterial DNA polymerase pol I fragment is the Klenow fragment (N-truncated *E. coli* pol I; Stratagene).

2. Thermostable (Useful for non PCR Assays)
   i. DNA polymerases naturally substantially lacking 5' to 3' exonuclease activity: Pol II or the pol III catalytic subunit from thermophilic eubacteria, such as *Bacillus* species (e.g., *stearothermophilus, caldotenax, caldovelox*)
   ii. DNA polymerase mutants substantially lacking 5' to 3' exonuclease activity: Suitable pol I DNA polymerases for N-truncation or mutagenesis can be isolated from thermophilic eubacteria such as the *Bacillus* species listed above. Thermostable N-truncated fragments of *B. stearothermophilus* DNA polymerase pol I are commercially available and sold under the trade names Bst DNA polymerase I large fragment (Bio-Rad and Isotherm DNA polymerase (Epicentre)). A C-terminal fragment of *Bacillus caldotenax* pol I is available from Panvera (sold under the tradename Ladderman).

3. Thermostable (Useful for PCR Assays)

i. DNA polymerases naturally substantially lacking 5' to 3' exonuclease activity: Pol II or polIII catalytic subunit from *Thermus* species (*aquaticus, thermophilus, flavus, ruber, caldophilus, filiformis, brokianus*) or from *Thermotoga maritima*. The catalytic pol III subunits from *Thermus thermophilus* and *Thermus aquaticus* are described in Yi-Ping et al., 1999, J. Mol. Evol., 48:756 and McHenry et al., 1997, J. Mol. Biol., 272:178.

ii. DNA polymerase mutants substantially lacking 5' to 3' exonuclease activity: Suitable pol I DNA polymerases for N-truncation or mutagenesis can be isolated from a variety of thermophilic eubacteria, including Thermus species and *Thermotoga maritima* (see above). Thermostable fragments of *Thermus aquaticus* DNA polymerase pol I (Taq) are commercially available and sold under the trade names KlenTaq1 (Ab Peptides), Stoffel fragment (Perkin-Elmer), and ThermoSequenase (Amersham). In addition to C-terminal fragments, 5' to 3' exonuclease⁻ Taq mutants are also commercially available, such as TaqFS (Hoffman-LaRoche). In addition to 5'-3' exonuclease versions of Taq, an N-truncated version of *Thermotoga maritima* DNA polymerase I is also commercially available (tradename UlTma, Perkin-Elmer).

Additional eubacteria related to those listed above are described in *Thermophilic Bacteria* (Kristjansson, J. K., ed.) CRC Press, Inc., Boca Raton, Fla., 1992.

D. Eukaryotic 5' to 3' Exonuclease DNA Polymerases (Useful for 37° C. Assays)

There are several DNA polymerases that have been identified in eukaryotes, including DNA pol α (replication/repair), δ (replication), ε (replication), β (repair) and γ (mitochondrial replication). Eukaryotic DNA polymerases are devoid of 5' to 3' exonuclease activity, as this activity is encoded by a separate polypeptide (e.g., mammalian FEN-1 or yeast RAD2). Suitable thermolabile DNA polymerases may be isolated from a variety of eukaryotes (including but not limited to yeast, mammalian cells, insect cells, *Drosophila*) and eukaryotic viruses (e.g., EBV, adenovirus).

It is possible that DNA polymerase mutants lacking 3'-5' exonuclease (proofreading) activity, in addition to lacking 5' to 3' exonuclease activity, could exhibit improved performance in FEN-based detection strategies. For example, reducing or abolishing inherent 3' to 5' exonuclease activity may lower background signals by diminishing non-specific exonucleolytic degradation of labeled probes. Three 3' to 5' exonuclease motifs have been identified, and mutations in these regions have been shown to abolish 3' to 5' exonuclease activity in Klenow, φ29, T4, T7, and Vent DNA polymerases, yeast Pol α, Pol β, and Pol γ, and *Bacillus subtilis* Pol III (reviewed in Derbeyshire et al., 1995, Methods. Enzymol. 262:363). Methods for preparing additional DNA polymerase mutants, with reduced or abolished 3' to 5' exonuclease activity, are well known in the art.

Commercially-available enzymes that lack both 5' to 3' and 3' to 5' exonuclease activities include Sequenase (exo⁻ T7; USB), Pfu exo⁻ (Stratagene), exo⁻ Vent (New England BioLabs), exo⁻ DeepVent (New England BioLabs), exo⁻ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche).

If polymerases other than Pfu are used, buffers and extension temperatures are selected to allow for optimal activity by the particular polymerase useful according to the invention. Buffers and extension temperatures useful for polymerases according to the invention are know in the art and can also be determined from the Vendor's specifications.

III. Nucleic Acids

A. Nucleic Acid Sequences Useful in the Invention

The invention provides for methods of detecting or measuring a target nucleic acid; and also utilizes oligonucleotides, primers and probes for forming a cleavage structure according to the invention and primers for amplifying a template nucleic acid sequence.

As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The complement of a nucleic acid sequence as used herein refers to an oligonucleotide which, when aligned with the nucleic acid sequence such that the 5' end of one sequence is paired with the 3' end of the other, is in "antiparallel association."

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature.

Because mononucleotides are reacted to make oligonucleotides in a manner such that the 5' phosphate of one mononucleotide pentose ring is attached to the 3' oxygen of its neighbor in one direction via a phosphodiester linkage, an end of oligonucleotide is referred to as the "5'end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the base pairs have disassociated.

B. Primers and Probes Useful According to the Invention

The invention provides for oligonucleotide primers and probes useful for detecting or measuring a nucleic acid, for amplifying a template nucleic acid sequence, and for forming a cleavage structure according to the invention.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

Oligonucleotide primers useful according to the invention are single-stranded DNA or RNA molecules that are hybridizable to a template nucleic acid sequence and prime enzymatic synthesis of a second nucleic acid strand. The primer is complementary to a portion of a target molecule present in a pool of nucleic acid molecules. It is contemplated that oligonucleotide primers according to the invention are prepared by synthetic methods, either chemical or enzymatic. Alternatively, such a molecule or a fragment thereof is naturally-occurring, and is isolated from its natural source or purchased from a commercial supplier. Oligonucleotide primers are 5 to 100 nucleotides in length, ideally from 17 to 40 nucleotides, although primers of different length are of use. Primers for amplification are preferably about 17-25 nucleotides. Primers for the production of a cleavage structure according to the invention are preferably about 17-45 nucleotides. Primers useful according to the invention are also designed to have a particular melting temperature (Tm) by the method of melting temperature estimation. Commercial programs, including Oligo™, Primer Design and programs available on the internet, including Primer3 and Oligo Calculator can be used to calculate a Tm of a nucleic acid sequence useful according to the invention. Preferably, the Tm of an amplification primer useful according to the invention, as calculated for example by Oligo Calculator, is preferably between about 45 and 65° C. and more preferably between about 50 and 60° C. Preferably, the Tm of a probe useful according to the invention is 7° C. higher than the Tm of the corresponding amplification primers.

Primers and probes according to the invention can be labeled and can be used to prepare a labeled cleavage structure. Pairs of single-stranded DNA primers, a DNA primer and a probe or a probe can be annealed to sequences within a target nucleic acid. In certain embodiments, a primer can be used to prime amplifying DNA synthesis of a target nucleic acid.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, Nucleic Acids Res. 12: 203, incorporated herein by reference. As a result, it is expected that a certain degree of mismatch at the priming site is tolerated. Such mismatch may be small, such as a mono-, di- or tri-nucleotide. Alternatively, a region of mismatch may encompass loops, which are defined as regions in which there exists a mismatch in an uninterrupted series of four or more nucleotides.

Numerous factors influence the efficiency and selectivity of hybridization of the primer to a second nucleic acid molecule. These factors, which include primer length, nucleotide sequence and/or composition, hybridization temperature, buffer composition and potential for steric hindrance in the region to which the primer is required to hybridize, will be considered when designing oligonucleotide primers according to the invention.

A positive correlation exists between primer length and both the efficiency and accuracy with which a primer will anneal to a target sequence. In particular, longer sequences have a higher melting temperature ($T_M$) than do shorter ones, and are less likely to be repeated within a given target sequence, thereby minimizing promiscuous hybridization. Primer sequences with a high G-C content or that comprise palindromic sequences tend to self-hybridize, as do their intended target sites, since unimolecular, rather than bimolecular, hybridization kinetics are generally favored in solution. However, it is also important to design a primer that contains sufficient numbers of G-C nucleotide pairings since each G-C pair is bound by three hydrogen bonds, rather than the two that are found when A and T bases pair to bind the target sequence, and therefore forms a tighter, stronger bond. Hybridization temperature varies inversely with primer annealing efficiency, as does the concentration of organic solvents, e.g. formamide, that might be included in a priming reaction or hybridization mixture, while increases in salt concentration facilitate binding. Under stringent annealing conditions, longer hybridization probes, or synthesis primers, hybridize more efficiently than do shorter ones, which are sufficient under more permissive conditions. Preferably, stringent hybridization is performed in a suitable buffer (for example, 1× Sentinel Molecular Beacon PCR core buffer, Stratagene Catalog #600500; 1×Pfu buffer, Stratagene Catalog #200536; or 1× cloned Pfu buffer, Stratagene Catalog #200532) under conditions that allow the nucleic acid sequence to hybridize to the oligonucleotide primers and/or probes (e.g., 95° C.). Stringent hybridization conditions can vary (for example from salt concentrations of less than about 1M, more usually less than about 500 mM and preferably less than about 200 mM) and hybridization temperatures can range (for example, from as low as 0° C. to greater than 22° C., greater than about 30° C., and (most often) in excess of about 37° C.) depending upon the lengths and/or the nucleic acid composition or the oligonucleotide primers and/or probes. Longer fragments may require higher hybridization temperatures for specific hybridization. As several factors affect the stringency of hybridization, the combination of parameters is more important than the absolute measure of a single factor.

Oligonucleotide primers can be designed with these considerations in mind and synthesized according to the following methods.

1. Oligonucleotide Primer Design Strategy

The design of a particular oligonucleotide primer for the purpose of sequencing or PCR, involves selecting a sequence that is capable of recognizing the target sequence, but has a minimal predicted secondary structure. The oligonucleotide sequence may or may not bind only to a single site in the target nucleic acid. Furthermore, the Tm of the oligonucleotide is optimized by analysis of the length and GC content of the oligonucleotide. Furthermore, when designing a PCR primer useful for the amplification of genomic DNA, the selected primer sequence does not demonstrate significant matches to sequences in the GeriBank database (or other available databases).

The design of a primer useful according to the invention, is facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and Amplify (described in Ausubel et al., 1995, Short Protocols in Molecular Biology, 3rd Edition, John Wiley & Sons). In one embodiment, primers are designed with sequences that serve as targets for other primers to produce a PCR product that has known sequences on the ends which serve as targets for further amplification (e.g. to sequence the PCR product). If many different target nucleic acids are amplified with specific primers that share a common 'tail' sequence', the PCR products from these distinct genes can subsequently be sequenced with a single set of primers. Alternatively, in order to facilitate subsequent cloning of amplified sequences, primers are designed with restriction enzyme site sequences appended to their 5' ends. Thus, all nucleotides of the primers are derived from a target nucleic acid or sequences adjacent to a target nucleic acid, except for the few nucleotides necessary to form a restriction enzyme site. Such enzymes and sites are well known in the art. If the genomic sequence of a target nucleic acid and the sequence of the open reading frame of a target nucleic acid are known, design of particular primers is well within the skill of the art.

It is well known by those with skill in the art that oligonucleotides can be synthesized with certain chemical and/or capture moieties, (including capture elements as defined herein) such that they can be coupled to solid supports and bind to a binding moiety or tag, as defined herein. Suitable capture elements include, but are not limited to a nucleic acid binding protein or a nucleotide sequence. Suitable capture elements include, but are not limited to, biotin, a hapten, a protein, or a chemically reactive moiety. Such oligonucleotides may either be used first in solution, and then captured onto a solid support, or first attached to a solid support and then used in a detection reaction. An example of the latter would be to couple a downstream probe molecule to a solid support, such that the 5' end of the downstream probe molecule comprised a fluorescent quencher. The same downstream probe molecule would also comprise a fluorophore in a location such that a FEN nuclease cleavage would physically separate the quencher from the fluorophore. For example, the target nucleic acid could hybridize with the solid-phase downstream probe oligonucleotide, and a liquid phase upstream primer could also hybridize with the target molecule, such that a FEN cleavage reaction occurs on the solid support and liberates the 5' quencher moiety from the complex. This would cause the solid support-bound fluorophore to be detectable, and thus reveal the presence of a cleavage event upon a suitably labeled or identified solid support. Different downstream probe molecules could be bound to different locations on an array. The location on the array would identify the probe molecule, and indicate the presence of the template to which the probe molecule can hybridize.

2. Synthesis

The primers themselves are synthesized using techniques that are also well known in the art. Methods for preparing oligonucleotides of specific sequence are known in the art, and include, for example, cloning and restriction digest analysis of appropriate sequences and direct chemical synthesis. Once designed, oligonucleotides are prepared by a suitable chemical synthesis method, including, for example, the phosphotriester method described by Narang et al., 1979, Methods in Enzymology, 68:90, the phosphodiester method disclosed by Brown et al., 1979, Methods in Enzymology, 68:109, the diethylphosphoramidate method disclosed in Beaucage et al., 1981, Tetrahedron Letters, 22:1859, and the solid support method disclosed in U.S. Pat. No. 4,458,066, or by other chemical methods using either a commercial automated oligonucleotide synthesizer (which is commercially available) or VLSIPS™ technology.

C. Probes

The invention provides for probes useful for forming a cleavage structure or a labeled cleavage structure as defined herein. Methods of preparing a labeled cleavage structure according to the invention are provided in the section entitled "Cleavage Structure" below.

As used herein, the term "probe" refers to a probe having a secondary structure that changes upon binding of the probe to a target nucleic acid and comprising a binding moiety, as defined herein, wherein the probe forms a duplex structure with a sequence in the target nucleic acid, due to complementarity of at least one sequence in the probe with a sequence in the target region. A probe according to the invention can also be labeled. The probe, preferably, does not contain a sequence complementary to sequence(s) used in the primer extension(s). Generally the 3' terminus of the probe will be "blocked" to prohibit incorporation of the probe into a primer extension product. Methods of labeling a probe according to the invention and suitable labels are described below in the section entitled "Cleavage Structure".

The general design of a probe according to the invention is described in the section entitled, "Primers and Probes Useful According to the Invention". Typically, a probe according to the invention comprises a target nucleic acid binding sequence that is from about 7-140 nucleotides, and preferably from about 10-140 nucleotides long (C, FIG. 4). A probe according to the invention also comprises two complementary nucleic acid sequence regions, as defined herein (b and b', FIG. 4) that are complementary and bind to each other to form a region of secondary structure in the absence of a target nucleic acid. Regions b and b' are 3-25 nucleotides, preferably 4-15 nucleotides and more preferably 5-11 nucleotides in length. The actual length will be chosen with reference to the target nucleic acid binding sequence such that the secondary structure of the probe is preferably stable when the probe is not bound to the target nucleic acid at the temperature at which cleavage of a cleavage structure comprising the probe bound to a target nucleic acid is performed.

A probe according to the invention is capable of forming a secondary structure as defined herein, (including a stem loop, a hairpin, an internal loop, a bulge loop, a branched structure and a pseudoknot) or multiple secondary structures, cloverleaf type structures or any three-dimensional structure as defined hereinabove.

For example, according to one embodiment of the present invention, a probe can be an oligonucleotide with secondary structure such as a hairpin or a stem-loop, and includes, but is not limited to molecular beacons, safety pins, scorpions, and sunrise/amplifluor probes.

Molecular beacon probes comprise a hairpin, or stem-loop structure which possesses a pair of interactive signal generating labeled moieties (e.g., a fluorophore and a quencher) effectively positioned to quench the generation of a detectable signal when the beacon probe is not hybridized to the target nucleic acid. The loop comprises a region that is complementary to a target nucleic acid. The loop is flanked by 5' and 3' regions ("arms") that reversibly interact with one another by means of complementary nucleic acid sequences when the region of the probe that is complementary to a nucleic acid target sequence is not bound to the target nucleic acid. Alternatively, the loop is flanked by 5' and 3' regions ("arms") that reversibly interact with one another by means of attached members of an affinity pair to form a secondary structure when the region of the probe that is complementary to a nucleic acid target sequence is not bound to the target nucleic acid. As used herein, "arms" refers to regions of a molecular beacon probe that a) reversibly interact with one another by means of complementary nucleic acid sequences when the region of the probe that is complementary to a nucleic acid target sequence is not bound to the target nucleic acid or b) regions of a probe that reversibly interact with one another by means of attached members of an affinity pair to form a secondary structure when the region of the probe that is complementary to a nucleic acid target sequence is not bound to the target nucleic acid. When a molecular beacon probe is not hybridized to target, the arms hybridize with one another to form a stem hybrid, which is sometimes referred to as the "stem duplex". This is the closed conformation. When a molecular beacon probe hybridizes to its target the "arms" of the probe are separated. This is the open conformation. In the open conformation an arm may also hybridize to the target. Such probes may be free in solution, or they may be tethered to a solid surface. When the arms are hybridized (e.g., form a stem) the quencher is very close to the fluorophore and effectively quenches or suppresses its fluorescence, rendering the probe dark. Such probes are described in U.S. Pat. No. 5,925,517 and U.S. Pat. No. 6,037,130.

As used herein, a molecular beacon probe can also be an "allele-discriminating" probe as described herein.

Molecular beacon probes have a fluorophore attached to one arm and a quencher attached to the other arm. The fluorophore and quencher, for example, tetramethylrhodamine and DABCYL, need not be a FRET pair.

For stem loop probes useful in this invention, the length of the probe sequence that is complementary to the target, the length of the regions of a probe (e.g., stem hybrid) that reversibly interact with one another by means of complementary nucleic acid sequences, when the region complementary to a nucleic acid target sequence is not bound to the target nucleic acid, and the relation of the two, is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region of the probe that is complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17-40 nucleotides, more preferably 17-30 nucleotides and most preferably 17-25 nucleotides long.

The oligonucleotide sequences of molecular beacon probes modified according to this invention may be DNA, RNA, cDNA or combinations thereof. Modified nucleotides may be included, for example nitropyrrole-based nucleotides or 2'-O-methylribonucleotides. Modified linkages also may be included, for example phosphorothioates. Modified nucleotides and modified linkages may also be incorporated in wavelength-shifting primers according to this invention.

Figure 9:
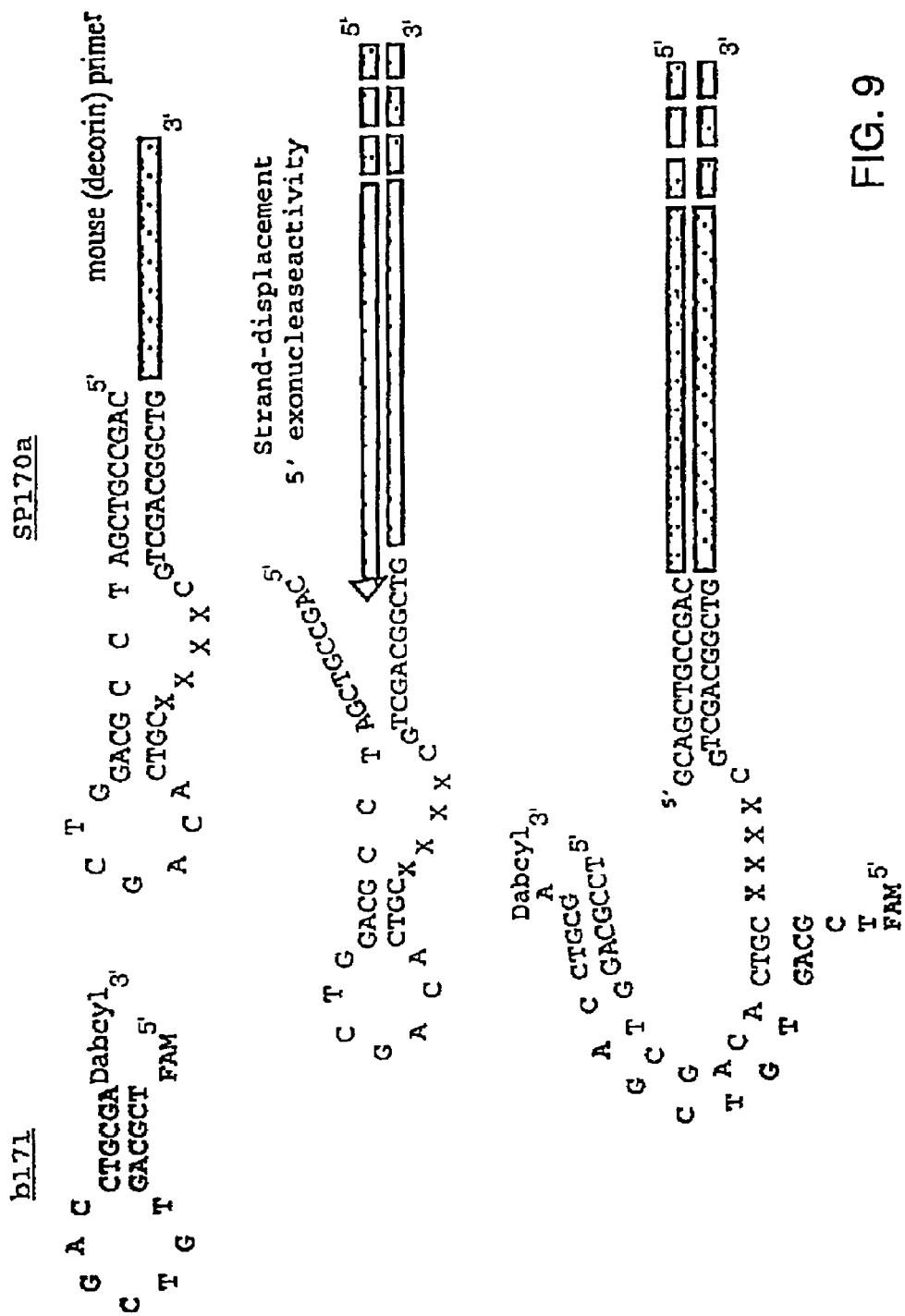
FIG. 9 is a representation of a safety pin probe.

A safety pin probe, as utilized in the present invention, requires a "universal" hairpin probe 1 (FIG. 9, b171), comprising a hairpin structure, with a fluorophore (FAM) on the 5' arm of the hairpin and a quencher (Dabcyl) on the 3' arm, and a probe 2 (FIG. 9, SP170a) comprising a stem-loop comprising two domains: the 5' two thirds of probe 2 have a (universal) sequence complementary to the hairpin probe 1, and nucleotides that will stop the DNA polymerase, and the 3' one third of probe 2, which serves as the target specific primer. As the polymerase, primed from the reverse primer (that is, the 3' one third of probe 2) synthesizes the top strand, the 5' end of probe 2 will be displaced and degraded by the 5' exonucleolytic activity until the "stop nucleotides" are reached. At this time the remainder of probe 2 opens up or unfolds and serves as a target for hairpin probe 1, thereby separating the fluorophore from the quencher (FIG. 9).

Figure 10:
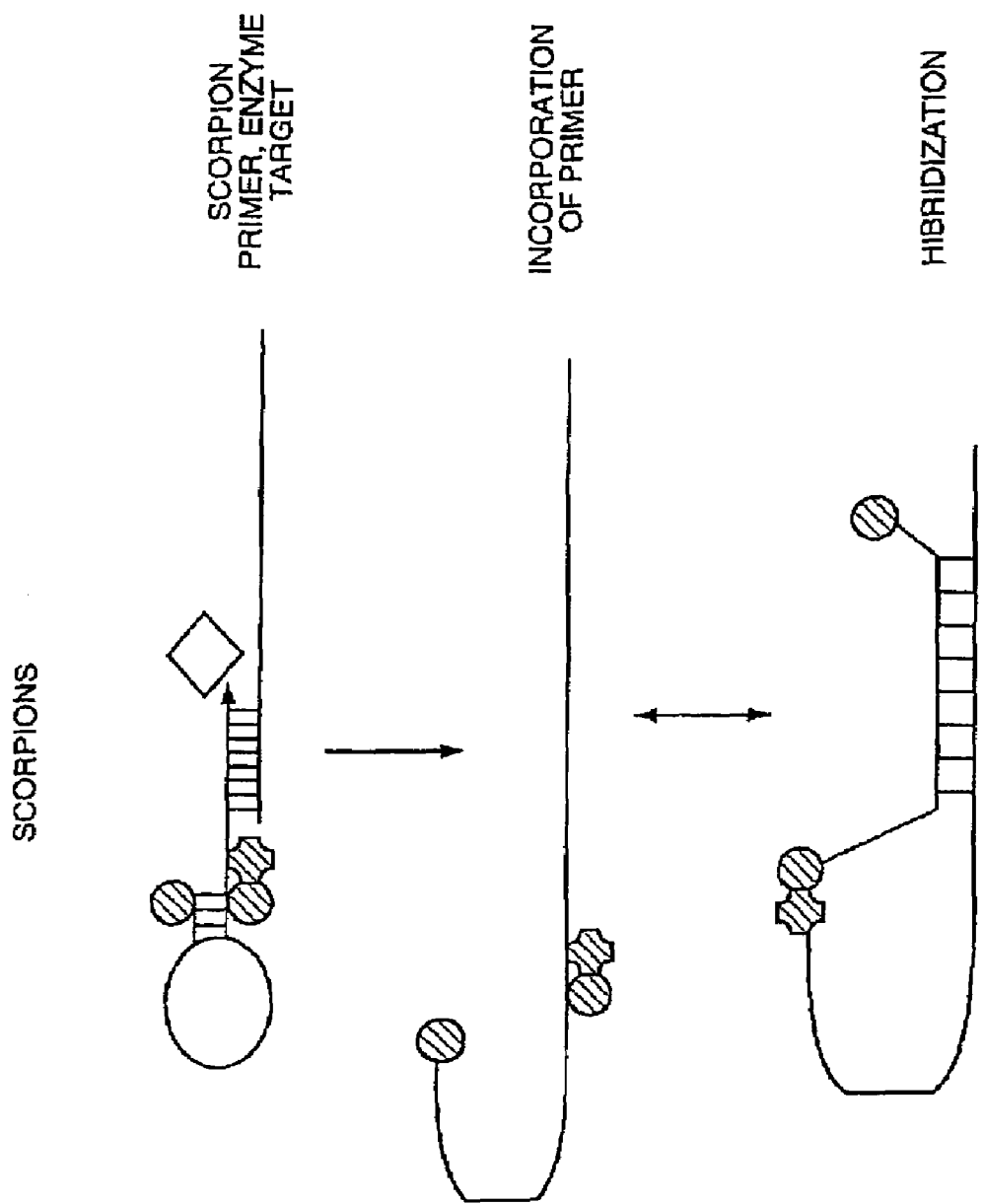
FIG. 10 is a representation of a scorpion probe.

Scorpion probes, as used in the present invention comprise a 3' primer with a 5' extended probe tail comprising a hairpin structure which possesses a fluorophore/quencher pair. The probe tail is "protected" from replication in the 5'→3' direction by the inclusion of hexethylene glycol (HEG) which blocks the polymerase from replicating the probe. During the first round of amplification the 3' target-specific primer anneals to the target and is extended such that the scorpion is now incorporated into the newly synthesized strand, which possesses a newly synthesized target region for the 5' probe. During the next round of denaturation and annealing, the probe region of the scorpion hairpin loop will hybridize to the target, thus separating the fluorophore and quencher and creating a measurable signal. Such probes are described in Whitcombe et al., *Nature Biotechhology* 17: 804-807 (1999), and in FIG. 10.

Figure 11:
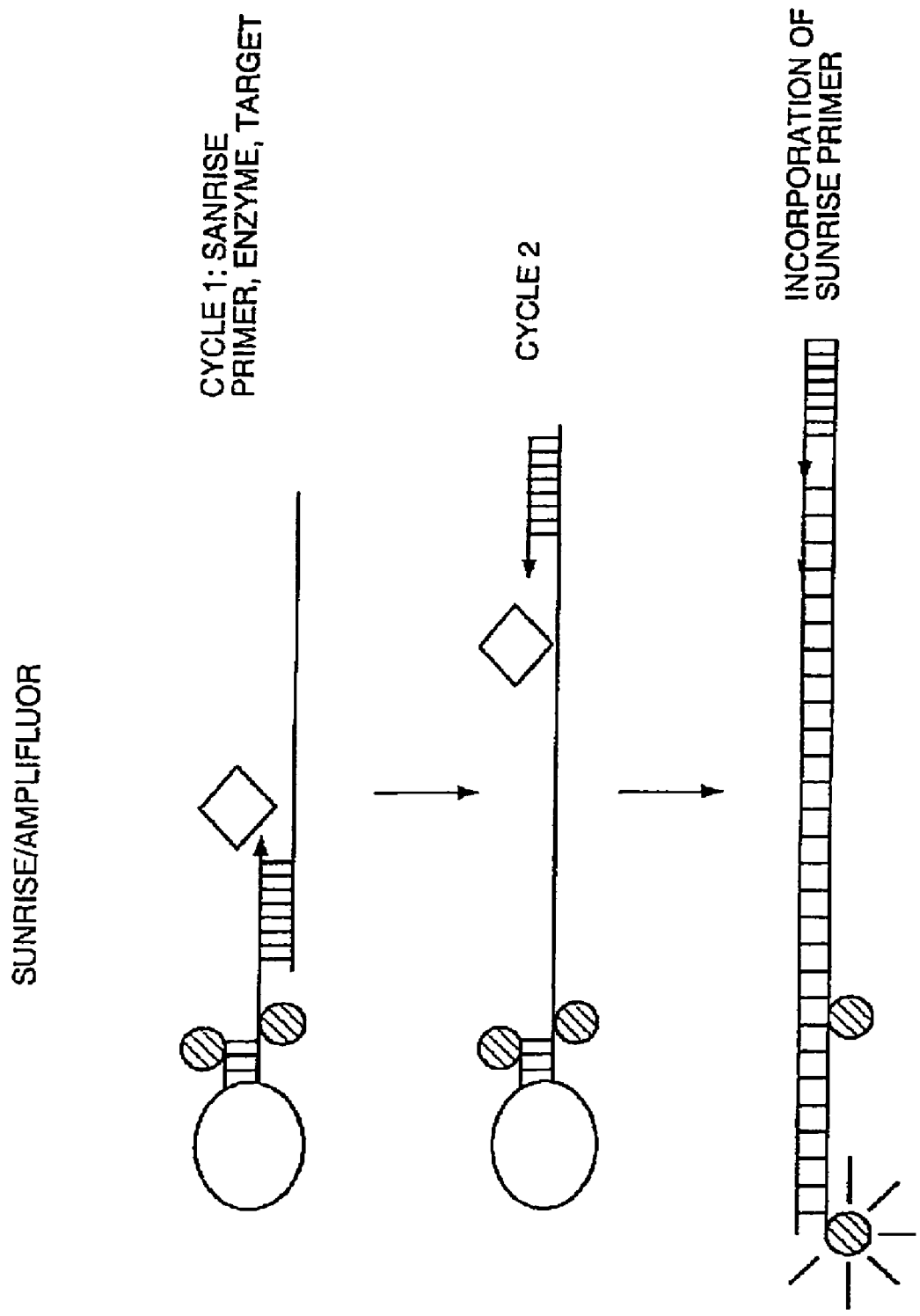
FIG. 11 is a representation of a sunrise/amplifluor probe

An additional oligonucleotide probe useful in the present invention is the sunrise/amplifluor probe. The sunrise/amplifluor probe is of similar construction as the scorpion probe with the exception that is lacks the HEG monomer to block the 5'→3' replication of the hairpin probe region. Thus, in the first round of amplification, the 3' target specific primer of the sunrise/amplifluor anneals to the target and is extended, thus incorporating the hairpin probe into the newly synthesized strand (sunrise strand). During the second round of amplification a second, non-labeled primer anneals to the 3' end of the sunrise strand (Cycle 2 in FIG. 11). However, as the polymerase reaches the 5' end of the hairpin, due to the lack of the HEG stop sequence, the polymerase will displace and replicate the hairpin, thus separating the fluorophore and quencher, and incorporating the linearized hairpin probe into the new strand. Probes of this type are described further in Nazarneko et al., *Nucleic Acid Res.* 25: 2516-2521 (1997), and in FIG. 11.

For safety pin, scorpion and sunrise/amplifluor probes useful in this invention, the length of the probe sequence that is complementary to the target, the length of the regions of a probe (e.g., stem hybrid) that reversibly interact with one another by means of complementary nucleic acid sequences when the region complementary to a nucleic acid target sequence is not bound to the target nucleic acid and the relation of the two is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17-40 nucleotides, more preferably 17-30 nucleotides and most preferably 17-25 nucleotides long. The stability of the interaction between the regions of a probe that reversibly interact with one another by means of complementary nucleic acid sequences is determined by routine experimentation to achieve proper functioning. In addition to length, the stability of the interaction between the regions of a probe that reversibly interact with one another by means of complementary nucleic acid sequences can be adjusted by altering the G-C content and inserting destabilizing mismatches. One of the regions of a probe that reversibly interact with one another by means of complementary nucleic acid sequences can be designed to be partially or completely complementary to the target. If the 3' arm is complementary to the target the probe can serve as a primer for a DNA polymerase. Also, wavelength-shifting molecular beacon probes can be immobilized to solid surfaces, as by tethering, or be free-floating.

A wide range of fluorophores may be used in probes and primers according to this invention. Available fluorophores include coumarin, fluorescein, tetrachlorofluorescein, hexachlorofluorescein, Lucifer yellow, rhodamine, BODIPY, tetramethylrhodamine, Cy3, Cy5, Cy7, eosine, Texas red and ROX. Combination fluorophores such as fluorescein-rhodamine dimers, described, for example, by Lee et al. (1997), Nucleic Acids Research 25:2816, are also suitable. Fluorophores may be chosen to absorb and emit in the visible spectrum or outside the visible spectrum, such as in the ultraviolet or infrared ranges.

Suitable quenchers described in the art include particularly DABCYL and variants thereof, such as DABSYL, DABMI and Methyl Red. Fluorophores can also be used as quenchers, because they tend to quench fluorescence when touching certain other fluorophores. Preferred quenchers are either chromophores such as DABCYL or malachite green, or fluorophores that do not fluoresce in the detection range when the probe is in the open conformation.

D. Production of a Nucleic Acid

The invention provides nucleic acids to be detected and or measured, for amplification of a target nucleic acid and for formation of a cleavage structure.

The present invention utilizes nucleic acids comprising RNA, cDNA, genomic DNA, synthetic forms, and mixed polymers. The invention includes both sense and antisense strands of a nucleic acid. According to the invention, the nucleic acid may be chemically or biochemically modified or may contain non-natural or derivatized nucleotide bases. Such modifications include, for example, labels, methylation, substitution of one or more of the naturally occurring nucleotides with an analog, internucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

1. Nucleic Acids Comprising DNA a. Cloning

Nucleic acids comprising DNA can be isolated from cDNA or genomic libraries by cloning methods well known to those skilled in the art (Ausubel et al., supra). Briefly, isolation of a DNA clone comprising a particular nucleic acid sequence involves screening a recombinant DNA or cDNA library and identifying the clone containing the desired sequence. Cloning will involve the following steps. The clones of a particular library are spread onto plates, transferred to an appropriate substrate for screening, denatured, and probed for the presence of a particular nucleic acid. A description of hybridization conditions, and methods for producing labeled probes is included below.

The desired clone is preferably identified by hybridization to a nucleic acid probe or by expression of a protein that can be detected by an antibody. Alternatively, the desired clone is identified by polymerase chain amplification of a sequence defined by a particular set of primers according to the methods described below.

The selection of an appropriate library involves identifying tissues or cell lines that are an abundant source of the desired sequence. Furthermore, if a nucleic acid of interest contains regulatory sequence or intronic sequence a genomic library is screened (Ausubel et al., supra).

b. Genomic DNA

Nucleic acid sequences of the invention are amplified from genomic DNA. Genomic DNA is isolated from tissues or cells according to the following method.

To facilitate detection of a variant form of a gene from a particular tissue, the tissue is isolated free from surrounding normal tissues. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added 1/2 volume of 7.5M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 µg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used for PCR analysis, according to the invention.

c. Restriction Digest (of cDNA or Genomic DNA)

Following the identification of a desired cDNA or genomic clone containing a particular target nucleic acid, nucleic acids of the invention may be isolated from these clones by digestion with restriction enzymes.

The technique of restriction enzyme digestion is well known to those skilled in the art (Ausubel et al., supra). Reagents useful for restriction enzyme digestion are readily available from commercial vendors including Stratagene, as well as other sources.

d. PCR

Nucleic acids of the invention may be amplified from genomic DNA or other natural sources by the polymerase chain reaction (PCR). PCR methods are well-known to those skilled in the art.

PCR provides a method for rapidly amplifying a particular DNA sequence by using multiple cycles of DNA replication catalyzed by a thermostable, DNA-dependent DNA polymerase to amplify the target sequence of interest. PCR requires the presence of a target nucleic acid to be amplified, two single stranded oligonucleotide primers flanking the sequence to be amplified, a DNA polymerase, deoxyribonucleoside triphosphates, a buffer and salts.

PCR, is performed as described in Mullis and Faloona, 1987, Methods Enzymol., 155: 335, herein incorporated by reference.

The polymerase chain reaction (PCR) technique, is disclosed in U.S. Pat. Nos. 4,683,202, 4,683,195 and 4,800,159.

In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science* 230:1350.

PCR is performed using template DNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of a suitable buffer, 0.4 µl of 1.25 µM dNTP, 2.5 units of Taq DNA polymerase (Stratagene) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Detection methods generally employed in standard PCR techniques use a labeled probe with the amplified DNA in a hybridization assay. Preferably, the probe is labeled, e.g., with $^{32}P$, biotin, horseradish peroxidase (HRP), etc., to allow for detection of hybridization.

Other means of detection include the use of fragment length polymorphism (PCR FLP), hybridization to allele-specific oligonucleotide (ASO) probes (Saiki et al., 1986, *Nature* 324:163), or direct sequencing via the dideoxy method (using amplified DNA rather than cloned DNA). The standard PCR technique operates (essentially) by replicating a DNA sequence positioned between two primers, providing as the major product of the reaction a DNA sequence of discrete length terminating with the primer at the 5' end of each strand. Thus, insertions and deletions between the primers result in product sequences of different lengths, which can be detected by sizing the product in PCR-FLP. In an example of ASO hybridization, the amplified DNA is fixed to a nylon filter (by, for example, UV irradiation) in a series of "dot blots", then allowed to hybridize with an oligonucleotide probe labeled with HRP under stringent conditions. After washing, terramethylbenzidine (TMB) and hydrogen peroxide are added: HRP oxidizes the hydrogen peroxide, which in turn oxidizes the TMB to a blue precipitate, indicating a hybridized probe.

A PCR assay for detecting or measuring a nucleic assay according to the invention is described in the section entitled "Methods of Use".

2. Nucleic Acids Comprising RNA

The present invention also provides a nucleic acid comprising RNA.

Nucleic acids comprising RNA can be purified according to methods well known in the art (Ausubel et al., supra). Total RNA can be isolated from cells and tissues according to methods well known in the art (Ausubel et al., supra) and described below.

RNA is purified from mammalian tissue according to the following method. Following removal of the tissue of interest, pieces of tissue of $\leq 2$ g are cut and quick frozen in liquid nitrogen, to prevent degradation of RNA. Upon the addition of a suitable volume of guanidinium solution (for example 20 ml guanidinium solution per 2 g of tissue), tissue samples are ground in a tissuemizer with two or three 10-second bursts. To prepare tissue guanidinium solution (1 L) 590.8 g guanidinium isothiocyanate is dissolved in approximately 400 ml DEPC-treated $H_2O$. 25 ml of 2 M Tris-HCl, pH 7.5 (0.05 M final) and 20 ml $Na_2EDTA$ (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18: 5294).

Alternatively, RNA is isolated from mammalian tissue according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5 ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4° C. after all components have been added. The sample is separated by centrifugation for 20 min at 10,000×g, 4° C., precipitated by the addition of 1 ml of 100% isopropanol, incubated for 30 minutes at −20° C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100-200 µl DEPC-treated water or DEPC-treated 0.5% SDS (Chomczynski and Sacchi, 1987, *Anal. Biochem.*, 162: 156).

Nucleic acids comprising RNA can be produced according to the method of in vitro transcription.

The technique of in vitro transcription is well known to those of skill in the art. Briefly, the gene of interest is inserted into a vector containing an SP6, T3 or T7 promoter. The vector is linearized with an appropriate restriction enzyme that digests the vector at a single site located downstream of the coding sequence. Following a phenol/chloroform extraction, the DNA is ethanol precipitated, washed in 70% ethanol, dried and resuspended in sterile water. The in vitro transcription reaction is performed by incubating the linearized DNA with transcription buffer (200 mM Tris-HCl, pH 8.0, 40 mM $MgCl_2$, 10 mM spermidine, 250 NaCl [T7 or T3] or 200 mM Tris-HCl, pH 7.5, 30 mM $MgCl_2$, 10 mM spermidine [SP6]), dithiothreitol, RNase inhibitors, each of the four ribonucleoside triphosphates, and either SP6, T7 or T3 RNA polymerase for 30 min at 37° C. To prepare a radiolabeled polynucleotide comprising RNA, unlabeled UTP will be omitted and $^{35}S$—UTP will be included in the reaction mixture. The DNA template is then removed by incubation with DNaseI. Following ethanol precipitation, an aliquot of the radiolabeled RNA is counted in a scintillation counter to determine the cpm/µl (Ausubel et al., supra).

Alternatively, nucleic acids comprising RNA are prepared by chemical synthesis techniques such as solid phase phosphoramidite (described above).

3. Nucleic Acids Comprising Oligonucleotides

A nucleic acid comprising oligonucleotides can be made by using oligonucleotide synthesizing machines which are commercially available (described above).

IV. Cleavage Structure

The invention provides for a cleavage structure that can be cleaved by a nuclease (e.g., a FEN nuclease), and therefore teaches methods of preparing a cleavage structure. The invention also provides a labeled cleavage structure and methods of preparing a labeled cleavage structure.

A probe having a secondary structure that changes upon binding of the probe to the target nucleic acid is used to prepare a cleavage structure according to the invention. A probe according to the invention has a secondary structure as defined herein, (including a stem loop, a hairpin, an internal loop, a bulge loop, a branched structure and a pseudoknot) or multiple secondary structures, cloverleaf type structures or any three-dimensional structure, as defined hereinabove. Probes useful for forming a cleavage structure according to the invention may also comprise covalently bound or non-covalently bound subunits (e.g., a bi-molecular or multi-molecular probe as defined herein).

A. Preparation of a Cleavage Structure

In one embodiment, a cleavage structure according to the invention is formed by incubating a) an upstream, preferably extendable 3' end, preferably an oligonucleotide primer, b) an oligonucleotide probe having a secondary structure, as defined herein, that changes upon binding to a target nucleic acid and comprising a binding moiety, located not more than 5000 nucleotides downstream of the upstream primer and c) an appropriate target nucleic acid wherein the target sequence is complementary to both primers and d) a suitable buffer (for example Sentinel Molecular Beacon PCR core buffer (Catalog #600500) or 10×Pfu buffer available from Stratagene (Catalog #200536), under conditions that allow the nucleic acid sequence to hybridize to the oligonucleotide primers (for example 95° C. for 2-5 minutes followed by cooling to between approximately 50-60° C.). The optimal temperature will vary depending on the specific probe(s), primers and polymerases. In preferred embodiments of the invention a cleavage structure comprises an overlapping flap wherein the 3' end of an upstream oligonucleotide capable of hybridizing to a target nucleic acid (for example A in FIG. 4) is complementary to 1 or more base pair(s) of the downstream oligonucleotide probe (for example C in FIG. 4) that is annealed to a target nucleic acid and wherein the 1 base pair overlap is directly downstream of the point of extension of the single stranded flap.

According to this embodiment of the 3' end of the upstream oligonucleotide primer is extended by the synthetic activity of a polymerase according to the invention such that the newly synthesized 3' end of the upstream oligonucleotide primer partially displaces the 5' end of the downstream oligonucleotide probe. Extension is preferably carried out in the presence of 1× Sentinel Molecular beacon core buffer or 1×Pfu buffer for 15 seconds at 72° C.

In another embodiment of the invention, a cleavage structure according to the invention can be prepared by incubating a target nucleic acid with a partially complementary oligonucleotide probe having a secondary structure, as defined herein, that changes upon binding to a target nucleic acid and comprising a binding moiety, to a target nucleic acid such that the 3' complementary region anneals to the target nucleic acid and the non-complementary 5' region that does not anneal to the target nucleic acid forms a 5' flap. Annealing is preferably carried out under conditions that allow the nucleic acid sequence to hybridize to the oligonucleotide primer (for example 95° C. for 2-5 minutes followed by cooling to between approximately 50-60° C.) in the presence a suitable buffer (for example 1× Sentinel Molecular beacon core buffer or 1×Pfu buffer.

In another embodiment of the invention, a cleavage structure according to the invention can be prepared by incubating a target nucleic acid with an upstream primer capable of hybridizing to the target nucleic acid and a partially complementary oligonucleotide probe having a secondary structure, as defined herein, that changes upon binding to a target nucleic acid and comprising a binding moiety, such that the 3' complementary region anneals to the target nucleic acid and the non-complementary 5' region that does not anneal to the target nucleic acid forms a 5' flap. Annealing is preferably carried out under conditions that allow the nucleic acid sequence to hybridize to the oligonucleotide primer (for example 95° C. for 2-5 minutes followed by cooling to between approximately 50-60° C.) in the presence a suitable buffer (for example 1× Sentinel Molecular beacon core buffer (Stratagene) or 1×Pfu buffer (Stratagene).

B. How to Prepare a Labeled Cleavage Structure

In the present invention, a label is attached to an oligonucleotide probe having a secondary structure, as defined herein, that changes upon binding to a target nucleic acid and comprising a binding moiety, that comprises a cleavage structure. Thus, the cleaved mononucleotides or small oligonucleotides which are cleaved by the endonuclease activity of the flap-specific nuclease can be detected.

In one embodiment, a labeled cleavage structure according to the invention is formed by incubating a) an upstream extendable 3' end, preferably an oligonucleotide primer, b) a labeled probe having a secondary structure, as defined herein, that changes upon binding to a target nucleic acid and comprising a binding moiety, located not more than 5000 nucleotides downstream of the upstream primer and c) an appropriate target nucleic acid wherein the target sequence is complementary to the oligonucleotides and d) a suitable buffer (for example 1× Sentinel Molecular beacon core buffer or 1×Pfu buffer), under conditions that allow the nucleic acid sequence to hybridize to the oligonucleotide primers (for example 95° C. for 2-5 minutes followed by cooling to between approximately 50-60° C.). A cleavage structure according to the invention also comprises an overlapping flap wherein the 3' end of an upstream oligonucleotide capable of hybridizing to a target nucleic acid (for example A in FIG. 4) is complementary to 1 base pair of the downstream oligonucleotide probe having a secondary structure, as defined herein, that changes upon binding to a target nucleic acid comprising a binding moiety (for example C in FIG. 4) that is annealed to a target nucleic acid and wherein the 1 base pair overlap is directly downstream of the point of extension of the single stranded flap. The 3' end of the upstream primer is extended by the synthetic activity of a polymerase such that the newly synthesized 3' end of the upstream primer partially displaces the labeled 5' end of the downstream probe. Extension is preferably carried out in the presence of 1× Sentinel Molecular beacon core buffer or 1×Pfu buffer for 15 seconds at 72° C.

In another embodiment, a cleavage structure according to the invention can be prepared by incubating a target nucleic acid with a probe having a secondary structure, as defined herein, that changes upon binding to a target nucleic acid and comprising a binding moiety, and further comprising a non-complementary, labeled, 5' region that does not anneal to the target nucleic acid and forms a 5' flap, and a complementary 3' region that anneals to the target nucleic acid. Annealing is preferably carried out under conditions that allow the nucleic acid sequence to hybridize to the oligonucleotide primer (for example 95° C. for 2-5 minutes followed by cooling to between approximately 50-60° C.) in the presence a suitable buffer (for example 1× Sentinel Molecular beacon core buffer or 1×Pfu buffer).

In another embodiment, a cleavage structure according to the invention can be prepared by incubating a target nucleic acid with an upstream primer that is capable of hybridizing to the target nucleic acid and a probe having a secondary structure, as defined herein, that changes upon binding to a target nucleic acid and comprising a binding moiety, and further comprising a non-complementary, labeled, 5' region that does not anneal to the target nucleic acid and forms a 5' flap, and a complementary 3' region that anneals to the target nucleic acid. Annealing is preferably carried out under conditions that allow the nucleic acid sequence to hybridize to the oligonucleotide primer (for example 95° C. for 2-5 minutes followed by cooling to between approximately 50-60° C.) in the presence a suitable buffer (for example 1× Sentinel Molecular beacon core buffer or 1×Pfu buffer).

Subsequently, any of several strategies may be employed to distinguish the uncleaved labeled nucleic acid from the cleaved fragments thereof. The invention provides for methods for detecting the amount of cleaved, released, nucleic acid fragment that is captured by binding of a binding moiety or a tag to a capture element, on a solid support. In this manner, the present invention permits identification of those samples that contain a target nucleic acid.

The oligonucleotide probe is labeled, as described below, by incorporating moieties detectable by spectroscopic, photochemical, biochemical, immunochemical, enzymatic or chemical means. The method of linking or conjugating the label to the oligonucleotide probe depends, of course, on the type of label(s) used and the position of the label on the probe. A probe that is useful according to the invention can be labeled at the 5' end, the 3' end or labeled throughout the length of the probe.

A variety of labels that would be appropriate for use in the invention, as well as methods for their inclusion in the probe, are known in the art and include, but are not limited to, enzymes (e.g., alkaline phosphatase and horseradish peroxidase) and enzyme substrates, radioactive atoms, fluorescent dyes, chromophores, chemiluminescent labels, electro-chemiluminescent labels, such as Origen™ (Igen), that may interact with each other to enhance, alter, or diminish a signal. Of course, if a labeled molecule is used in a PCR based assay carried out using a thermal cycler instrument, the label must be able to survive the temperature cycling required in this automated process.

Among radioactive atoms, $^{33}$P or, $^{32}$P is preferred. Methods for introducing $^{33}$P or, $^{32}$P into nucleic acids are known in the art, and include, for example, 5' labeling with a kinase, or random insertion by nick translation. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. The above description is not meant to categorize the various labels into distinct classes, as the same label may serve in several different modes. For example, $^{125}$I may serve as a radioactive label or as an electron-dense reagent. HRP may serve as an enzyme or as antigen for a monoclonal antibody. Further, one may combine various labels for desired effect. For example, one might label a probe with biotin, and detect the presence of the probe with avidin labeled with $^{125}$I, or with an anti-biotin monoclonal antibody labeled with HRP. Other permutations and possibilities will be readily apparent to those of ordinary skill in the art and are considered as equivalents within the scope of the instant invention.

Fluorophores for use as labels in constructing labeled probes of the invention include rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), mono-bromobimane, pyrene trisulfonates, such as Cascade Blue, and monobromorimethyl-ammoniobimane. In general, fluorophores with wide Stokes shifts are preferred, to allow using fluorimeters with filters rather than a monochromometer and to increase the efficiency of detection.

Probes labeled with fluorophores can readily be used in nuclease (e.g. FEN-nuclease) mediated cleavage of a cleavage structure comprising a labeled probe according to the invention. If the label is on the 5'-end of the probe, the nuclease (e.g. FEN-nuclease) generated labeled fragment is separated from the intact, hybridized probe by procedures well known in the art.

In another embodiment of the invention, detection of the hydrolyzed, labeled probe can be accomplished using, for example, fluorescence polarization, a technique to differentiate between large and small molecules based on molecular tumbling. Large molecules (i.e., intact labeled probe) tumble in solution much more slowly than small molecules. Upon linkage of a fluorescent moiety to an appropriate site on the molecule of interest, this fluorescent moiety can be measured (and differentiated) based on molecular tumbling, thus differentiating between intact and digested probe.

In some situations, one can use two interactive labels (e.g., FRET or non-FRET pairs) on a single oligonucleotide probe with due consideration given for maintaining an appropriate spacing of the labels on the oligonucleotide to permit the separation of the labels during oligonucleotide probe unfolding (e.g., for example due to a change in the secondary structure of the probe) or hydrolysis. Preferred interactive labels useful according to the invention include, but are not limited to rhodamine and derivatives, fluorescein and derivatives, Texas Red, coumarin and derivatives, crystal violet and include, but are not limited to DABCYL, TAMRA and NTB (nitrothiazole blue) in addition to any of the FRET or non-FRET labels described herein.

The fluorescence of the released label is then compared to the label remaining bound to the target. It is not necessary to separate the nuclease (e.g. FEN-nuclease) generated fragment and the probe that remains bound to the target after cleavage in the presence of nuclease (e.g. FEN-nuclease) if the probe is synthesized with a fluorophore and a quencher that are separated by about 20 nucleotides. Alternatively, the quencher is positioned such that the probe will not fluoresce when not hybridized to the target nucleic acid. Such a dual labeled probe will not fluoresce when intact or when not hybridized to the target nucleic acid (or in the case of bi- or multimolecular probes, when the probe is not dissociated) because the light emitted from the dye is quenched by the quencher. Thus, any fluorescence emitted by an intact probe is considered to be background fluorescence. In one embodiment, when a labeled probe is cleaved by a FEN nuclease, dye and quencher are separated and the released fragment will fluoresce. Alternatively, when a labeled probe is hybridized to a target nucleic acid, the distance between the dye and the quencher is increased and the level of fluorescence increases. In an embodiment wherein the probe is a bi- or multi-molecular probe, dissociation of the molecules comprising the probe results in an increase in fluorescence. The amount of fluorescence is proportional to the amount of nucleic acid target sequence present in a sample.

In yet another embodiment, two labeled nucleic acids are used, each complementary to separate regions of separate strands of a double-stranded target sequence, but not to each other, so that a labeled nucleic acid anneals downstream of each primer. For example, the presence of two probes can potentially double the intensity of the signal generated from a single label and may further serve to reduce product strand reannealing, as often occurs during PCR amplification. The probes are selected so that the probes bind at positions adjacent (downstream) to the positions at which primers bind:

One can also use multiple probes in the present invention to achieve other benefits. For instance, one could test for any number of pathogens in a sample simply by putting as many probes as desired into the reaction mixture; the probes could each comprise a different label to facilitate detection.

One can also achieve allele-specific or species-specific discrimination using multiple probes in the present invention, for instance, by using probes that have different $T_m$s and conducting the annealing/cleavage reaction at a temperature specific for only one probe/allele duplex. One can also achieve allele specific discrimination by using only a single probe and examining the types of cleavage products generated. In one embodiment of the invention, the probe is designed to be exactly complementary, at least in the 5' terminal region, to one allele but not to the other allele(s). With respect to the other allele(s), the probe will be mismatched in the 5' terminal region of the probe so that a different cleavage product will be generated as compared to the cleavage product generated when the probe is hybridized to the exactly complementary allele.

Although probe sequence can be selected to achieve important benefits, one can also realize important advantages by selection of probe labels(s) and/or tag as defined herein. The labels may be attached to the oligonucleotide directly or indirectly by a variety of techniques. Depending on the precise type of label or tag used, the label can be located at the 5' or 3' end of the probe, located internally in the probe, or attached to spacer arms of various sizes and compositions to facilitate signal interactions. Using commercially available phosphoramidite reagents, one can produce oligomers containing functional groups (e.g., thiols or primary amines) at either the 5- or the 3-terminus via an appropriately protected phosphoramidite, and can label them using protocols described in, for example, PCR Protocols: A Guide to Methods and Applications, Innis et al., eds. Academic Press, Ind., 1990.

Methods for introducing oligonucleotide functionalizing reagents to introduce one or more sulfhydryl, amino or hydroxyl moieties into the oligonucleotide probe sequence, typically at the 5' terminus, are described in U.S. Pat. No. 4,914,210. A 5' phosphate group can be introduced as a radio-isotope by using polynucleotide kinase and gamma-$^{32}$P ATP or gamma-$^{33}$P-ATP to provide a reporter group. Biotin can be added to the 5' end by reacting an aminothymidine residue, or a 6-amino hexyl residue, introduced during synthesis, with an N-hydroxysuccinimide ester of biotin. Labels at the 3' terminus may employ polynucleotide terminal transferase to add the desired moiety, such as for example, cordycepin $^{35}$S-dATP, and biotinylated dUTP.

Oligonucleotide derivatives are also available labels. For example, etheno-dA and etheno-A are known fluorescent adenine nucleotides that can be incorporated into a nucleic acid probe. Similarly, etheno-dC or 2-amino purine deoxyriboside is another analog that could be used in probe synthesis. The probes containing such nucleotide derivatives may be hydrolyzed to release much more strongly fluorescent mononucleotides by flap-specific nuclease activity.

C. Cleaving a Cleavage Structure and Generating a Signal

A cleavage structure according to the invention can be cleaved by the methods described in the section above, entitled "Nucleases".

D. Detection of Released Labeled Fragments

Detection or verification of the labeled fragments may be accomplished by a variety of methods well known in the art and may be dependent on the characteristics of the labeled moiety or moieties comprising a labeled cleavage structure. Preferably, the released labeled fragments are captured by binding of a binding moiety to a capture element attached to a solid support.

1. Capture Element

A capture element, according to the invention can be any moiety that specifically binds (e.g. via hydrogen bonding or via an interaction between, for example a nucleic acid binding protein and a nucleic acid binding site or between complementary nucleic acids) a binding moiety, as a result of attractive forces that exist between the binding moiety and the capture element.

According to the invention, a binding moiety includes a region of a probe that binds to a capture element. A capture element according to the invention can be a nucleic acid sequence that is complementary to and binds to, for example, via hydrogen bonding, a binding moiety comprising a region of a probe that binds to a capture element. For example, a binding moiety is a region of a probe comprising the nucleic acid sequence 5'AGCTACTGATGCAGTCACGT3' and the corresponding capture element comprises the nucleic acid sequence 5'TCGATGACTACGTCAGTGCA3'.

The invention also provides for binding moiety-capture element or tag-capture element pairs wherein the binding moiety or tag is a DNA binding protein and the corresponding capture element is the DNA sequence recognized and bound by the DNA binding protein. The invention also provides for binding moiety-capture element or tag-capture element pairs wherein the capture element is a DNA binding protein and the corresponding binding moiety or tag is the DNA sequence recognized and bound by the DNA binding protein.

DNA sequence/DNA binding protein interactions useful according to the invention include but are not limited to c-myb, AAF, abd-A, Abd-B, ABF-2, ABF-1, ACE2, ACF, ADA2, ADA3, Adf-1, Adf-2a, ADR1, AEF-1, AF-2, AFP1, AGIE-BP1, AhR, AIC3, AIC4, AID2, AIIN3, ALF1B, alpha-1, alpha-CP1, alpha-CP2a, alpha-CP2b, alpha-factor, alpha-PAL, alpha2 uNF1, alpha2 uNF3, alphaA-CRYBP1, alphaH2-alphaH3, alphaMHCBF1, aMEF-2, AML1, AnCF, ANF, ANF-2, Antp, AP-1, AP-2, AP-3, AP-5, APETALA1, APETALA3, AR, ARG RI, ARG RII, Arnt, AS-C T3, AS321, ASF-1, ASH-1, ASH-3b, ASP, AT-13P2, ATBF1-A, ATF, ATF-1, ATF-3, ATF-3deltaZIP, ATF-adelta, ATF-like, Athb-1, Athb-2, Axial, abaA, ABF-1, Ac, ADA-NF1, ADD1, Adf-2b, AF-1, AG, AIC2, AIC5, ALF1A, alpha-CBF, alpha-CP2a, alpha-CP2b, alpha-IRP, alpha2 uNF2, alphaH0, AmdR, AMT1, ANF-1, Ap, AP-3, AP-4, APETALA2, aRA, ARG RIII, ARP-1, Ase, ASH-3a, AT-BP1, ATBF1-B, ATF-2, ATF-a, ATF/CREB, Ato, B factor, B', B-Myc, B-TFIID, band I factor, BAP, Bcd, BCFI, Bcl-3, beta-1, BETA1, BETA2, BF-1, BGP1, BmFTZ-F1, BP1, BR-C Z1, BR-C Z2, BR-C Z4, Brachyury, BRF1, Br1A, Brn-3a, Brn-4, Brn-5, BUF1, BUF2, B-Myb, BAF1, BAS1, BCFII, beta-factor, BETA3, BLyF, BP2, BR-C Z3, brahma, byr3, c-abl, c-Ets-1, c-Ets-2, c-Fos, c-Jun, c-Maf, c-myb, c-Myc, c-Qin, c-Rel, C/EBP, C/EBPalpha, C/EBPbeta, C/EBPdelta, C/EBPepsilon, C/EBPgamma, C1, CAC-binding protein, CACCC-binding factor, Cactus, Cad, CAD1, CAP, CArG box-binding protein, CAUP, CBF, CBP, CBTF, CCAAT-binding factor, CCBF, CCF, CCK-1a, CCK-1b, CD28RC, CDC10, Cdc68, CDF, cdk2, CDP, Cdx-1, Cdx-2, Cdx-3, CEBF, CEH-18, CeMyoD, CF1, Cf1a, CF2-I, CF2-II, CF2-III, CFF, CG-1, CHOP-10, Chox-2.7, CIIIB1, Clox, Cnc, CoMP1, core-binding factor, CoS, COUP, COUP-TF, CP1, CP1A, CP1B, CP2, CPBP, CPC1, CPE binding protein CPRF-1, CPRF-2, CPRF-3, CRE-BP1, CRE-BP2, CRE-BP3, CRE-BPa, CreA, CREB, CREB-2, CREBomega, CREMalpha, CREMbeta, CREMdelta, CREMepsilon, CREMgamma, CREMtaualpha, CRF, CSBP-1, CTCF, CTF, CUP2, Cut, Cux, Cx, cyclinA, CYS3, D-MEF2, Da, DAL82, DAP, DAT1, DBF-A, DBF4, DBP, DBSF, dCREB, dDP, dE2F, DEF, Delilah, delta factor, deltaCREB, deltaE1, deltaEF1, deltaMax, DENF, DEP, DF-1, Dfd, dFRA, dioxin receptor, dJRA, D1, DII, Dlx, DM-SSRP1, DMLP1, DP-1, Dpn, Dr1, DRTF, DSC1, DSP1, DSXF, DSXM, DTF, E, E1A, E2, E2BP, E2F, E2F-BF, E2F-I, E4, E47, E4BP4, E4F, E4TF2, E7, E74, E75, EBF, EBF1, EBNA, EBP, EBP40, EC, ECF, ECH, EcR, eE-TF, EF-1A, EF-C, EF1, EFgamma, Egr, eH-TF, EIIa, EivF, EKLF, Elf-1, Elg, Elk-1, ELP, Elt-2, EmBP-1, embryo DNA binding protein, Emc, EMF, Ems, Emx, En, ENH-binding protein, ENKTF-1, epsilonF1, ER, Erg, Esc, ETF, Eve, Evi, Evx, Exd, Ey, f(alpha-epsilon), F-ACT1, f-EBP, F2F, factor 1-3, factor B1, factor B2, factor delta, factor 1, FBF-A1, Fbf1, FKBP59, Fkh, F1bD, F1h, Fli-1, FLV-1, Fos-B, Fra-2, FraI, FRGY1, FRGY2, FTS, Ftz, Ftz-F1, G factor, G6 factor, GA-BF, GABP, GADD 153, GAF, GAGA factor, GAL4, GAL80, gamma-factor, gammaCAAT, gammaCAC, gammaOBP, GATA-1, GATA-2, GATA-3, GBF, GC1, GCF, GCF, GCN4, GCR1, GE1, GEBF-I, GF1, GFI, Gfi-1, GFII, GHF-5, GL1, Glass, GLO, GM-PBP-1, GP, GR, GRF-1, Gsb, Gsbn, Gsc, Gt, GT-1, Gtx, H, H16, H1ITF1, H$_2$Babp1, H2RIIBP, H2TF1, H4TF-1, HAC1, HAP1, Hb, HBLF, HBP-1, HCM1, heat-induced factor, HEB, HEF-1B, HEF-1T, HEF-4C, HEN1, HES-1, HIF-1, HiNF-A, HIP1, HIV-EP2, HIf, HMBI, HNF-1, HNF-3, Hox11, HOXA1, HOXA10, HOXA10PL2, HOXA11, HOXA2, HOXA3, HOXA4, HOXA5, HOXA7, HOXA9, HOXB1, HOXB3, HOXB4, HOXB5, HOXB6, HOXB7, HOXB8, HOXB9, HOXC5, HOXC6, HOXC8, HOXD1, HOXD10, HOXD11, HOXD12, HOXD13, HOXD4, HOXD8, HOXD9, HP1 site factor, Hp55, Hp65, HrpF, HSE-binding protein, HSF1, HSF2, HSF24, HSF3, HSF30, HSF8, hsp56, Hsp90, HST, HSTF, I-POU, IBF, IBP-1, ICER, ICP4, ICSBP, Id1, Id2, Id3, Id4, IE1, EBP1, IEFga, IF1, IF2, IFNEX, IgPE-1, IK-1, IkappaB, Il-1 RF, IL-6 RE-BP, Il-6 RF, ILF, ILRF-A, IME1, INO2, INSAF, IPF1, IRBP, IRE-ABP, IREBF-1, IRF-1, ISGF-1, Isl-1, ISRF, ITF, IUF-1, Ixr1, JRF, Jun-D, JunB, JunD, K-2, kappay factor, kBF-A, KBF1, KBF2, KBP-1, KER-1, Ker1, KN1, Kni, Knox3, Kr, kreisler, KRF-1, Krox-20, Krox-24, Ku autoantigen, KUP, Lab, LAC9, LBP, Lc, LCR-F1, LEF-1, LEF-1S, LEU3, LF-A1, LF-B1, LF-C, LF-H3beta, LH-2, Lim-1, Lim-3, lin-11, lin-31, lin-32, LIP, LIT-1, LKLF, Lmx-1, LRF-1, LSF, LSIRF-2, LVa, LVb-binding factor, LVc, LyF-1, Lyl-1, M factor, M-Twist, M1, m3, Mab-18, MAC1, Mad, MAF, MafB, MafF, MafG, MafK, Ma163, MAPF1, MAPF2, MASH-1, MASH-2, mat-Mc, mat-Pc, MATa1, MATalpha1, MATalpha2, MATH-1, MATH-2, Max1, MAZ, MBF-1, MBP-1, MBP-2, MCBF, MCM1, MDBP, MEB-1, Mec-3, MECA, mediating factor, MEF-2, MEF-2C, MEF-2D, MEF1, MEP-1, Meso1, MF3, Mi, MIF, MIG1, MLP, MNB1a, MNF1, MOK-2, MP4, MPBF, MR, MRF4, MSN2, MSN4, Msx-1, Msx-2, MTF-1, mtTF1, muEBP-B, muEBP-C2, MUF1, MUF2, Mxi1, Myef-2, Myf-3, Myf-4, Myf-5, Myf-6, Myn, MyoD, myogenin, MZF-1, N-Myc, N-Oct-2, N-Oct-3, N-Oct-4, N-Oct-5, Nau, NBF, NC1, NeP1, Net, NeuroD, neurogenin, NF III-a, NF-1, NF-4FA, NF-AT, NF-BA1, NF-CLE0a, NF-D, NF-E, NF-E1b, NF-E2, NF-EM5, NF-GMa, NF-H1, NF-IL-2A, NF-InsE1, NF-kappaB, NF-lambda2, NF-MHCIIA, NF-muE1, NF-muNR, NF-S, NF-TNF, NF-U1, NF-W1, NF-X, NF-Y, NF-Zc, NFalpha1, NFAT-1, NFbetaA, NFdeltaE3A, NFdeltaE4A, NFe, NFE-6, NFH3-1, NFH3-2, NFH3-3, NFH3-4, NGFI-B, NGFI-C, NHP, Nil-2-a, NIP, NIT2, Nkx-2.5, NLS1, NMH7, NP-III, NP-IV, NP-TCII, NP-Va, NRDI, NRF-1, NRF-2, Nrf1, Nrf2, NRL, NRSF form 1, NTF, NUC-1, Nur77, OBF, OBP, OCA-B, OCSTF, Oct-1, Oct-10, Oct-11, Oct-2, Oct-2.1, Oct-2.3, Oct-4, Oct-5, Oct-6, Oct-7, Oct-8, Oct-9, Oct-B2, Oct-R, Octa-factor, octamer-binding factor, Odd, Olf-1, Opaque-2, Otd, Otx1, Otx2, Ovo, P, P1, p107, p130, p28 modulator, p300, p38erg, p40x, p45, p49erg, p53, p55, p55erg, p58, p65delta, p67, PAB1, PacC, Pap1, Paraxis, Pax-1, Pax-2, Pax-3, Pax-5, Pax-6, Pax-7, Pax-8, Pb, Pbx-1a, Pbx-1b, PC, PC2, PC4, PC5, Pcr1, PCRE1, PCT1, PDM-1, PDM-2, PEA1, PEB1, PEBP2, PEBP5, Pep-1, PF1, PGA4, PHD1, PHO2, PHO4, PHO80, Phox-2, Pit-1, PO-B, pointedP1, Pou2, PPAR, PPUR, PPYR, PR, PRA, Prd, PrDI-BF1, PREB, Prh proein a, protein b, protein c, protein d, PRP, PSE1, PTF, Pu box binding factor, PU.1, PUB1, PuF, PUF-I, Pur factor, PUT3, pX, qa-1F, QBP, R, R1, R2, RAd-1, RAF, RAP1, RAR, Rb, RBP-Jkappa, RBP60, RC1, RC2, REB1, Re1A, Re1B, repressor of CAR1 expression, REX-1, RF-Y, RF1, RFX, RGM1, RIM1, RLM1, RME1, Ro, RORalpha, Rox1, RPF1, RPGalpha, RREB-1, RRF1, RSRFC4, runt, RVF, RXR-alpha, RXR-beta, RXR-beta2, RXR-gamma, S-CREM, S-CREMbeta, S8, SAP-1a, SAP1, SBF, Sc, SCBPalpha, SCD1/BP, SCM-inducible factor, Scr, Sd, Sdc-1, SEF-1, SF-1, SF-2, SF-3, SF-A, SGC1, SGF-1, SGF-2, SGF-3, SGF-4, SIF, SIII, Sim, SIN1, Skn-1, SKO1, Slp1, Sn, SNP1, SNF5, SNAPC43, Sox-18, Sox-2, Sox-4, Sox-5, Sox-9, Sox-LZ, Sp1, spE2F, Sph factor, Spi-B, Sprm-1, SRB10, SREBP, SRF, SRY, SSDBP-1, ssDBP-2, SSRP1, STAF-50, STAT, STAT1, STAT2, STAT3, STAT4, STAT5, STAT6, STC, STD1, Ste11, Ste12, Ste4, STM, Su(f), SUM-1, SWI1, SWI4, SWI5, SWI6, SWP, T-Ag, t-Pou2, T3R, TAB, all TAFs including subunits, Tal-1, TAR factor, tat, Tax, TBF1, TBP, TCF, TDEF, TEA1, TEC1, TEF, tel, Tf-LF1, TFE3, all TFII related proteins, TBA1a, TGGCA-binding protein, TGT3, Th1, TIF1, TIN-1, TIP, T11, TMF, TR2, Tra-1, TRAP, TREB-1, TREB-2, TREB-3, TREF1, TREF2, Tsh, TTF-1, TTF-2, Ttk69k, TTP, Ttx, TUBF, Twi, TxREBP, TyBF, UBP-1, Ubx, UCRB, UCRF-L, UF1-H3beta, UFA, UFB, UHF-1, UME6, Unc-86, URF, URSF, URTF, USF, USF2, v-ErbA, v-Ets, v-Fos, v-Jun, v-Maf, v-Myb, v-Myc, v-Qin; v-Rel, Vab-3, vaccinia virus DNA-binding protein, Vav, VBP, VDR, VETF, vHNF-1, VITF, Vmw65, Vp1, Vp16, Whn, WT1, X-box binding protein, X-Twist, X2BP, XBP-1, XBP-2, XBP-3, XF1, XF2, XFD-1, XFD-3, xMEF-2, XPF-1, XrpFI, XW, XX, yan, YB-1, YEB3, YEBP, Yi, YPF1, YY1, ZAP, ZEM1, ZEM2/3, Zen-1, Zen-2, Zeste, ZF1, ZF2, Zfh-1, Zfh-2, Zfp-35, ZID, Zmhoxla, Zta and all related characterized and uncharacterized homologs and family members related to these DNA binding proteins or activities, and the DNA sequence recognized by the above-recited DNA binding proteins. Methods of identifying a DNA sequence recognized by a DNA binding protein are known in the art (see for example, U.S. Pat. No. 6,139,833).

The invention also contemplates DNA sequence/DNA binding protein interactions including but not limited to the tetracycline (tet) repressor, beta.-galactosidase (lac repressor), the tryptophan (trp) repressor, the lambda specific repressor protein, CRO, and the catabolite activator protein, CAP and the DNA sequence recognized by each of these DNA binding proteins and known in the art. DNA/DNA binding protein interactions useful according to the invention also include restriction enzymes and the corresponding restriction sites, preferably under conditions wherein the nuclease activity of the restriction enzyme is suppressed (U.S. Pat. No. 5,985,550, incorporated herein by reference).

Other DNA:Protein interactions useful according to the invention include (i) the DNA protein interactions listed in Tables 1 and 2, and (ii) bacterial, yeast, and phage systems such as lambda OL-OR/CrO (U.S. Pat. No. 5,726,014, incorporated herein by reference). Any pair comprising a protein that binds to a specific recognition sequence and the cognate recognition sequence may be useful in the present invention.

TABLE 1

DNA-BINDING SEQUENCES

| Test sequence | DNA-binding Protein |
|---|---|
| EBV origin of replication | EBNA |
| HSV origin of replication | UL9 |
| VZV origin of replication | UL9-like |
| HPV origin of replication | E2 |
| Interleukin 2 enhancer | NFAT-1 |
| HIV LTR | NFAT-1 |
|  | NFkB |
| HBV enhancer | HNF-1 |
| Fibrogen promoter | HNF-1 |

TABLE 2

|  | Name | DNA Sequence Recognized* |
|---|---|---|
| Bacteria | lac repressor | AATTGTGAGCGGATAACAATT TTAACACTCGCCTATTGTTAA |
|  | CAP | TGTGAGTTAGCTCACT ACACTCAATCGAGTGA |
|  | lambda repressor | TATCACCGCCAGAGGTA ATAGTGGCGGTCTCCAT |
| Yeast | GAL4 | CGGAGGACTGTCCTCCG GCCTCCTGACAGGAGGC |
|  | MAT α2 | CATGTAATT GTACATTAA |
|  | GCN4 | ATGACTCAT TACTGAGTA |

TABLE 2-continued

|  | Name | DNA Sequence Recognized* |
|---|---|---|
| Drosophila | Krüppel | AACGGGTTAA TTGCCCAATT |
|  | bicoid | GGGATTAGA CCCTAATCT |
| Mammals | Sp1 | GGGCGG CCCGCC |
|  | Oct-1 | ATGCAAAT TACGTTTA |
|  | GATA-1 | TGATAG ACTATC |

*Each protein in this table can recognize a set of closely related DNA sequences; for convenience, only one recognition sequence is given for each protein.

Methods of performing a reaction wherein specific binding occurs between a capture element, as defined herein and a binding moiety, as defined herein, are well known in the art, see for example, Sambrook et al., supra; Ausubel et al., supra). A capture element, according to the invention can also be any moiety that specifically binds (e.g. via covalent or hydrogen bonding or electrostatic attraction or via an interaction between, for example a protein and a ligand, an antibody and an antigen, protein subunits, a nucleic acid binding protein and a nucleic acid binding site) a binding moiety or a tag, as a result of attractive forces that exist between the binding moiety or tag and the capture element. Methods of performing a reaction wherein specific binding occurs between a capture element, as defined herein and a tag, as defined herein, are well known in the art, see for example, Sambrook et al., supra; Ausubel et al., supra). Specific binding only occurs when the secondary structure of the probe comprising the binding moiety has "changed", as defined herein. Capture elements useful according to the invention include but are not limited to a nucleic acid binding protein or a nucleotide sequence, biotin, streptavidin, a hapten, a protein, a nucleotide sequence or a chemically reactive moiety.

In one embodiment of the invention, the reaction products, including the released labeled fragments, are subjected to size analysis. Methods for determining the size of a labeled fragment are known in the art and include, for example, gel electrophoresis, sedimentation in gradients, gel exclusion chromatography, mass spectroscopy, and homochromatography.

2. Solid Substrate

A solid substrate according to the invention is any surface to which a molecule (e.g., capture element) can be irreversibly bound, including but not limited to membranes, magnetic beads, tissue culture plates, silica based matrices, membrane based matrices, beads comprising surfaces including but not limited to styrene, latex or silica based materials and other polymers for example cellulose acetate, teflon, polyvinylidene difluoride, nylon, nitrocellulose, polyester, carbonate, polysulphone, metals, zeolites, paper, alumina, glass, polypropyle, polyvinyl chloride, polyvinylidene chloride, polytetrafluorethylene, polyethylene, polyamides, plastic, filter paper, dextran, germanium, silicon, (poly)tetrafluorethylene, gallium arsenide, gallium phosphide, silicon oxide, silicon nitrate and combinations thereof.

Useful solid substrates according to the invention are also described in Sambrook et al., supra, Ausubel et al., supra, U.S. Pat. Nos. 5,427,779, 5,512,439, 5,589,586, 5,716,854 and 6,087,102, Southern et al., 1999, *Nature Genetics Supplement*, 21:5 and Joos et al., 1997, *Analytical Biochemistry*, 247:96.

Methods of attaching a capture element to a solid support are known in the art and are described in Sambrook et al., supra, Ausubel et al., supra, U.S. Pat. Nos. 5,427,779, 5,512,439, 5,589,586, 5,716,854 and 6,087,102 and in Southern et al., supra and Joos et al., supra. Methods of immobilizing a nucleic acid sequence on a solid support are also provided by the manufacturers of the solid support, e.g., for membranes: Pall Corporation, Schleicher & Schuell, for magnetic beads; Dyal, for culture plates; Costar, Nalgenunc, and for other supports useful according to the invention, CPG, Inc.

The amount of released labeled fragment that is bound to a capture element attached to a solid support can be measured while the labeled fragment remains bound to the capture element or after release of the labeled fragment from the capture element. Release of a labeled fragment from a capture element is carried out by incubating labeled fragment-capture element complexes in the presence of an excess amount of a competing, unlabeled fragment or by the addition of a buffer that inhibits binding of the labeled fragment to the capture element, for example as a result of salt concentration or pH.

During or after amplification, separation of the released labeled fragments from, for example, a PCR mixture can be accomplished by, for example, contacting the PCR with a solid phase extractant (SPE). For example, materials having an ability to bind nucleic acids on the basis of size, charge, or interaction with the nucleic acid bases can be added to the PCR mixture, under conditions where labeled, uncleaved nucleic acids are bound and short, labeled fragments are not. Such SPE materials include ion exchange resins or beads, such as the commercially available binding particles Nensorb (DuPont Chemical Co.), Nucleogen (The Nest Group), PEI, BakerBond™ PEI, Amicon PAE 1,000, Selectacel™ PEI, Boronate SPE with a 3'-ribose probe, SPE containing sequences complementary to the 3'-end of the probe, and hydroxylapatite. In a specific embodiment, if a dual labeled oligonucleotide comprising a 3' biotin label separated from a 5' label by a nuclease susceptible cleavage site is employed as the signal means, the reaction mixture, for example a PCR amplified mixture can be contacted with materials containing a specific binding element such as avidin or streptavidin, or an antibody or monoclonal antibody to biotin, bound to a solid support such as beads and particles, including magnetic particles.

Following the step in which a reaction mixture, for example a PCR mixture has been contacted with an SPE, the SPE material can be removed by filtration, sedimentation, or magnetic attraction, leaving the labeled fragments free of uncleaved labeled oligonucleotides and available for detection.

3. Binding Moieties

A binding moiety according to the invention refers to a region of a probe that is released upon cleavage of the probe by a nuclease and binds specifically (via hydrogen binding with a complementary nucleic acid or via an interaction with a binding protein) to a capture element as a result of attractive forces that exist between the binding moiety and the capture element, and wherein specific binding between the binding moiety and the capture element only occurs when the secondary structure of the probe has "changed", as defined herein.

A "tag" refers to a moiety that is operatively linked to the 5' end of a probe (for example R in FIG. 1) and specifically binds to a capture element as a result of attractive forces that exist between the tag and the capture element, and wherein specific binding between the tag and the capture element only occurs when the secondary structure of the probe has changed (for example, such that the tag is accessible to a capture element). "Specifically binds" as it refers to a "tag" and a capture element means via covalent or hydrogen bonding or electrostatic attraction or via an interaction between, for example a protein and a ligand, an antibody and an antigen, protein subunits, or a nucleic acid binding protein and a nucleic acid binding site. Second binding moieties include but are not limited to biotin, streptavidin, a hapten, a protein, or a chemically reactive moiety.

According to the invention, a binding moiety includes a region of a probe that binds to a capture element. A capture element according to the invention can be a nucleic acid sequence that is complementary to and binds to, for example, via hydrogen bonding, a binding moiety comprising a region of a probe that binds to a capture element. For example, a binding moiety is a region of a probe comprising the nucleic acid sequence 5'AGCTACTGATGCAGTCACGT3' and the corresponding capture element comprises the nucleic acid sequence 5'TCGATGACTACGTCAGTGCA3'.

The invention also provides for binding moiety-capture element or tag-capture element pairs wherein the binding moiety or tag is a DNA binding protein and the corresponding capture element is the DNA sequence recognized and bound by the DNA binding protein. The invention also provides for binding moiety-capture element or tag-capture element pairs wherein the capture element is a DNA binding protein and the corresponding binding moiety or tag is the DNA sequence recognized and bound by the DNA binding protein.

DNA binding sequence/DNA binding protein interactions useful according to the invention are described above in the section entitled, "Detection of Released Labeled Fragments".

Methods of incorporating a tag, as defined herein, into a nucleic acid (e.g., a probe according to the invention) are well known in the art and are described in Ausubel et al., supra, Sambrook et al., supra, and U.S. Pat. Nos. 5,716,854 and 6,087,102.

IV. Determining the Stability of the Secondary Structure of a Probe

A. Melting Temperature Assay

A melting temperature assay, takes advantage of the different absorption properties of double stranded and single stranded DNA, that is, double stranded DNA (the double stranded DNA being that portion of a nucleic acid sequence that has folded back on itself to generate an antiparallel duplex structure wherein complementary sequences (base pairs) are associated via hydrogen bonding) absorbs less light than single stranded DNA at a wavelength of 260 nm, as determined by spectrophotometric measurement.

Figure 12A:
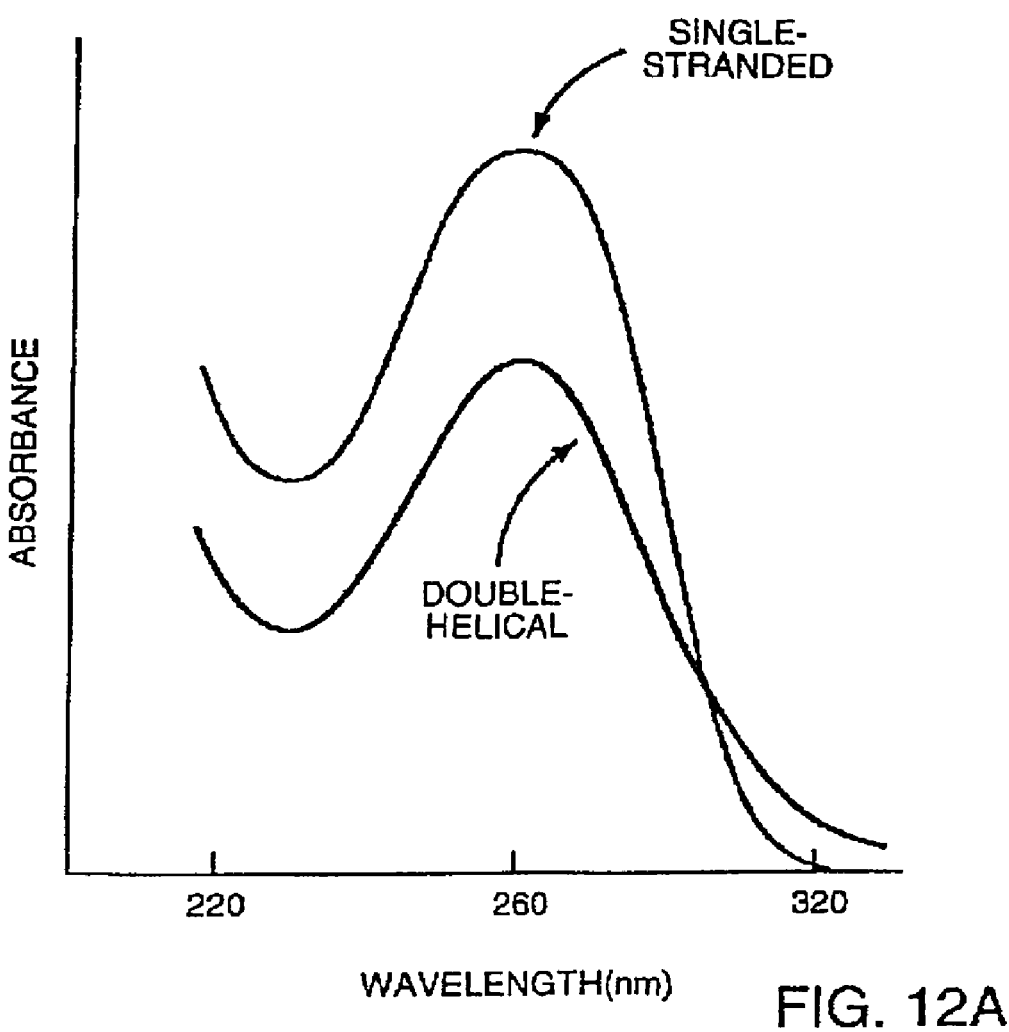
FIG. 12a is a graph demonstrating the difference in light absorbance of double-stranded versus single-stranded DNA.
Figure 12B:
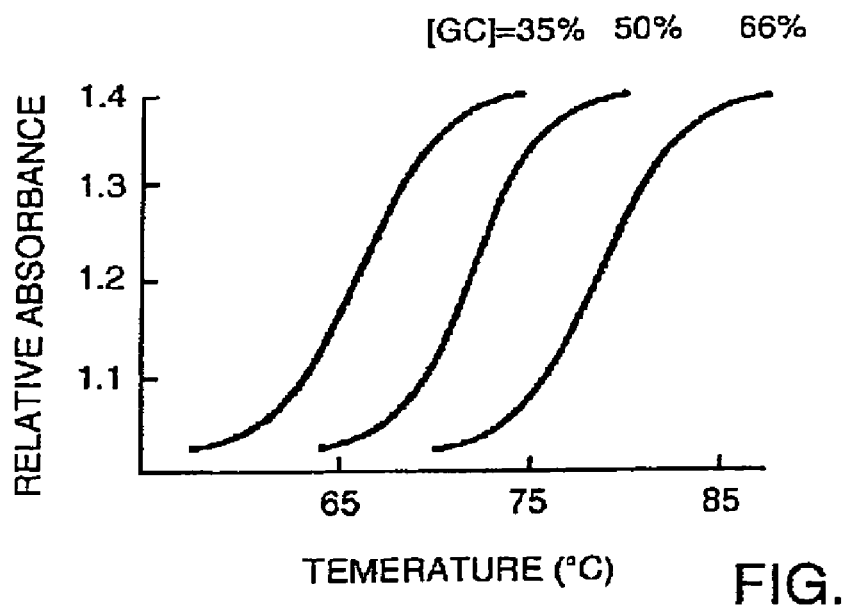
FIG. 12b is a graph demonstrating DNA melting curves.
Figure 12C:
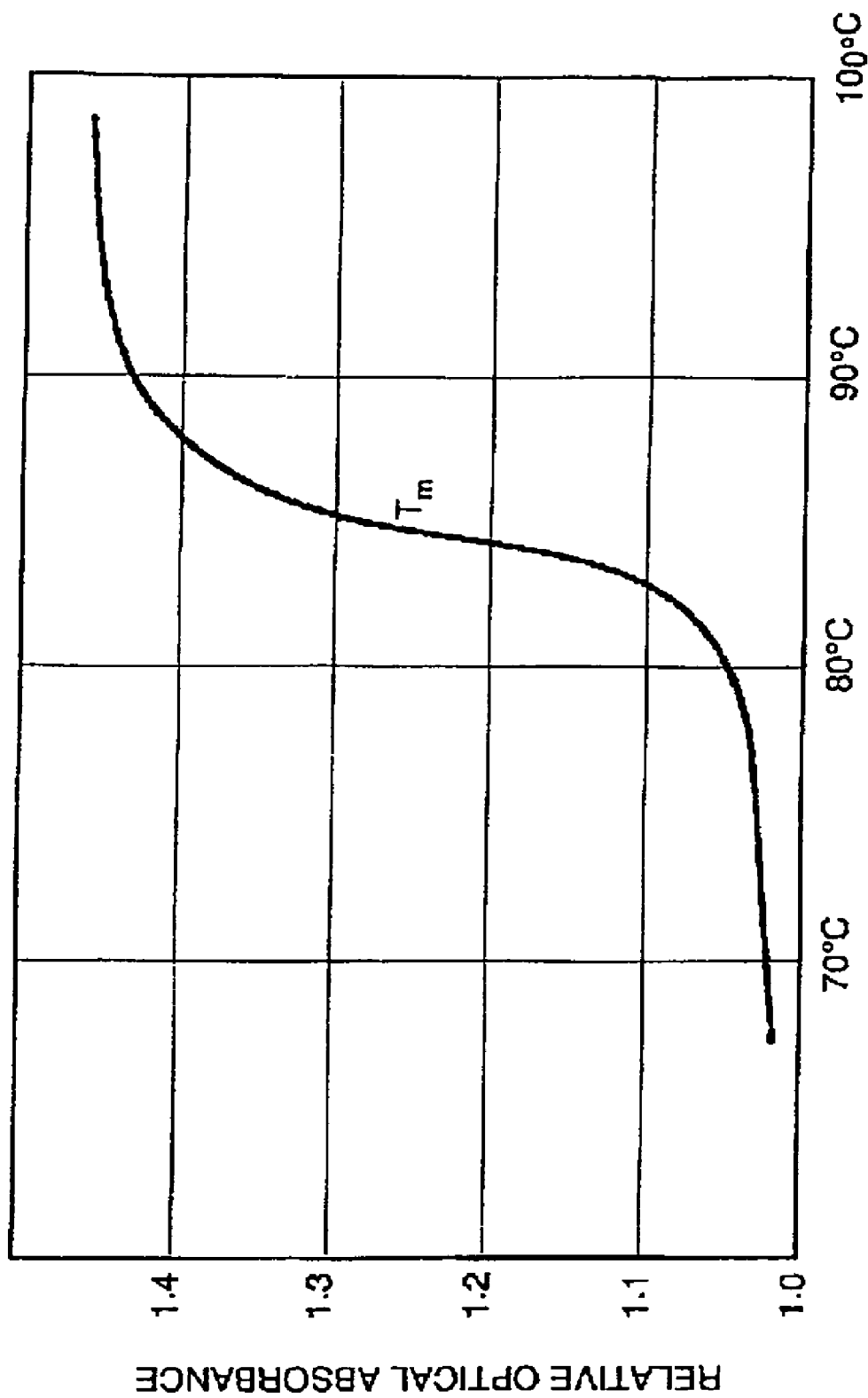
FIG. 12c is a graph demonstrating the effects of temperature on the relative optical absorbance of DNA.

The denaturation of DNA occurs over a narrow temperature range and results in striking changes in many of the physical properties of DNA. A particularly useful change occurs in optical density. The heterocyclic rings of nucleotides adsorb light strongly in the ultraviolet range (with a maximum close to 260 nm that is characteristic for each base). However, the adsorption of DNA is approximately 40% less than would be displayed by a mixture of free nucleotides of the same composition. This effect is called hyperchromism and results from interactions between the electron systems of the bases, made possible by their stacking in the parallel array of the double helix. Any departure from the duplex state is immediately reflected by a decline in this effect (that is, by an increase in optical density toward the value characteristic of free bases (FIG. 12a). The denaturation of double stranded DNA can therefore be followed by this hyperchromicity (FIGS. 12b and 12c)

The midpoint of the temperature range over which the strands of DNA separate is called the melting temperature, denoted $T_m$. An example of a melting curve determined by change in optical absorbance is shown in FIG. 12c. The curve always takes the same form, but its absolute position on the temperature scale (that is, its $T_m$) is influenced by both the base composition of the DNA and the conditions employed for denaturation.

The melting temperature of a DNA molecule depends markedly on its base composition. DNA molecules rich in GC base pairs have a higher Tm than those having an abundance of AT base pairs (FIG. 13b). The Tm of DNA from many species varies linearly with GC content, rising from 77° to 100° C. as the fraction of GC pairs increases from 20% to 78%. That is, the dependence of $T_m$ on base composition is linear, increasing about 0.4° C. for every percent increase in G-C content. GC base pairs are more stable than AT pairs because their bases are held together by three hydrogen bonds rather than by two. In addition, adjacent GC base pairs interact more strongly with one another than do adjacent AT base pairs. Hence, the AT-rich regions of DNA are the first to melt.

A major effect on $T_m$ is exerted by the ionic strength of the solution. The $T_m$ increases 16.6° C. for every tenfold increase in monovalent cation concentration. The most commonly used condition is to perform manipulations of DNA in 0.12 M phosphate buffer, which provides a monovalent Na+ concentration of 0.18M, and a $T_m$ of the order of 90° C.

The $T_m$ can be greatly varied by performing the reaction in the presence of reagents, such as formamide, that destabilize hydrogen bonds. This allows the $T_m$ to be reduced to as low as 40° C. with the advantage that the DNA does not suffer damage (such as strand breakage) that can result from exposure to high temperatures. (Stryer, Biochemistry, 1998, 3$^{rd}$ Edition, W.H. Freeman and Co., pp. 81-82 and Lewin, Genes II, 1985, John Wiley & Sons, p. 63-64).

The stability of the secondary structure of the probe according to the invention is determined in a melting temperature assay as follows.

A standard curve for the probe (for example FIG. 12c), wherein absorbance is plotted versus temperature, is prepared by incubating a sample comprising from about 0.2 µg/ml to 100 µg/ml of the probe in a buffer which allows for denaturing and reannealing of the probe at various temperatures for a time sufficient to permit denaturing and reannealing of the probe and measuring the absorbance of a sample in a quartz cuvette (with a pathlength appropriate for the spectrophotometer being used, e.g., 1 cm), in a spectrophotometer over a range of temperatures wherein the lower temperature limit of the range is at least 50° C. below, and the upper temperature limit of the range is at least 50° C. above the Tm or predicted Tm of the probe. The Tm of the probe is predicted based on the base pair composition according to methods well known in the art (see, Sambrook, supra; Ausubel, supra). Standard curves are generated and compared, using a variety of buffers (e.g., 1×TNE buffer (10×-0.1M Tris base, 10 mM EDTA, 2.0 M NaCl, pH 7.4), FEN nuclease buffer, described herein, 1× Cloned Pfu buffer, described herein, 1× Sentinel Molecular beacon buffer, described herein) including a buffer that is possible and preferentially optimal for the particular nuclease to be employed in the cleavage reaction. The pH of the buffer will be monitored as the temperature increases, and adjusted as is needed.

The assay is performed in a single-beam ultraviolet to visible range (UV-VIS) spectrophotometer Preferably, the assay is performed in a double-beam spectrophotometer to simplify measurements by automatically comparing the cuvette holding the sample solution to a reference cuvette (matched cuvette) that contains the blank. The blank is an equal volume of sample buffer.

The temperature of the spectrophotometer can be controlled such that the absorbance of the sample is measured at specific temperatures. Spectrophotometers useful according to the invention include but are not limited to the Beckman Coulter DU® 600/7000 Spectrophotometers in combination with the MicroTm Analysis Accessory (Beckman Coulter, Inc., Columbia, Md.).

Figure 12D:
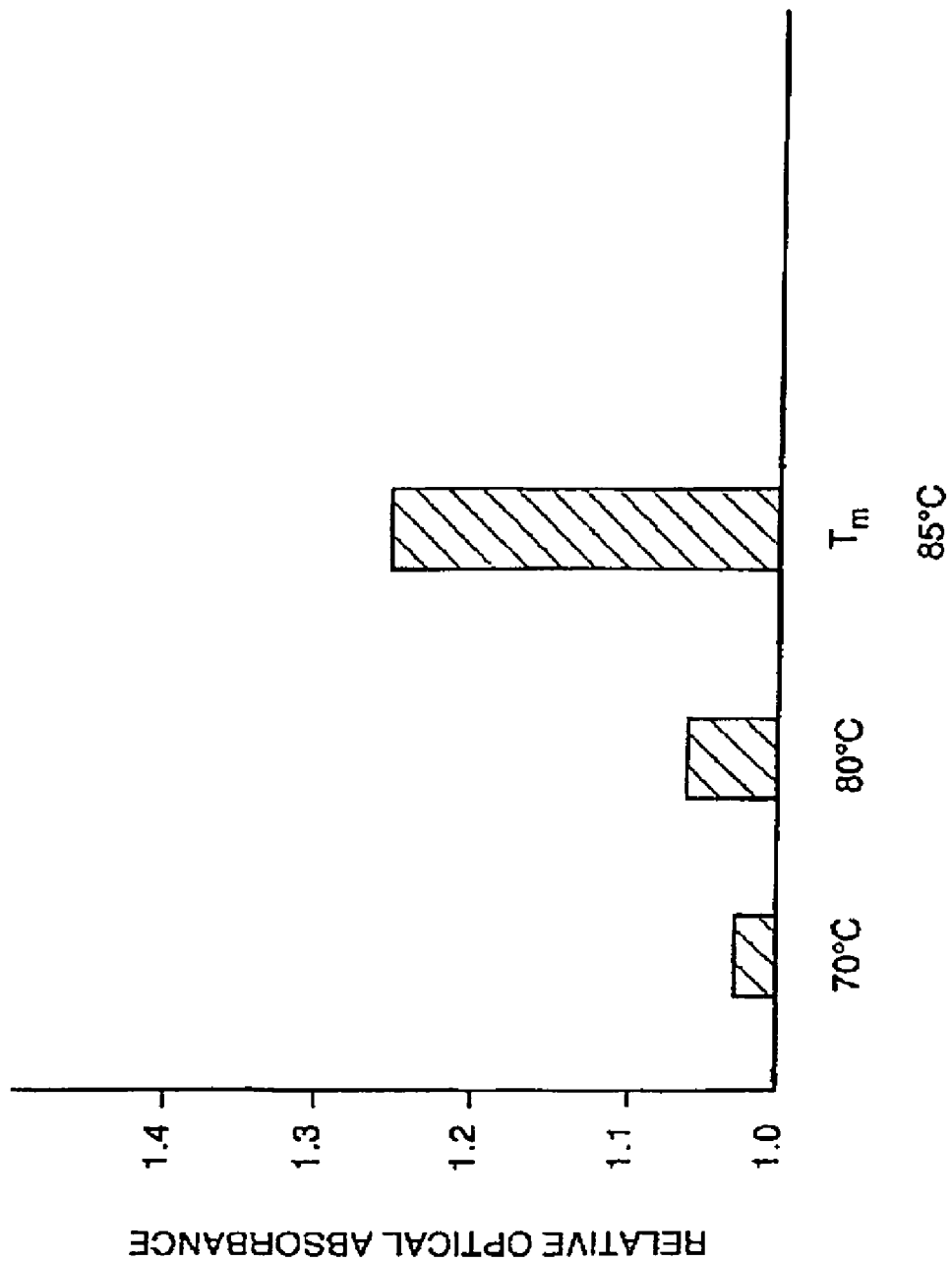
FIG. 12d is a graph demonstrating the effects of temperature on the relative optical absorbance of DNA.

The stability of the secondary structure of a probe at a particular temperature and in a buffer that is possible and preferentially optimal for the nuclease to be employed in the cleavage reaction of the probe, is determined by measuring the absorbance of the probe at a particular temperature, as above, and determining if the value of the absorbance is less than the absorbance at the Tm, as determined from the standard curve, wherein the standard curve is generated using either the same buffer as used at the test temperature, or a buffer known to produce a comparable standard curve, as described above. The secondary structure of the probe is "stable" in a melting temperature assay, at a temperature that is at or below the temperature of the cleavage reaction (i.e., at which cleavage is performed) if the level of light absorbance at the temperature at or below the temperature of the cleavage reaction is less (i.e., at least 5%, preferably 20% and most preferably 25% or more) than the level of light absorbance at a temperature that is equal to the Tm of the probe (see FIGS. 12c and 12d).

B. FRET

A FRET assay is useful in the invention for two purposes. The first is to determine whether the secondary structure of a probe is "stable" as defined herein. The second is to determine whether the secondary structure of the probe has undergone a "change" upon binding of the probe to the target nucleic acid.

"FRET" is a distance-dependent interaction between the electronic excited states of two dye molecules in which excitation is transferred from a donor molecule to an acceptor molecule. FRET is caused by a change in the distance separating a fluorescent donor group from an interacting resonance energy acceptor, either another fluorophore, a chromophore, or a quencher. Combinations of donor and acceptor moieties are known as "FRET pairs". Efficient FRET interactions require that the absorption and emission spectra of the dye pairs have a high degree of overlap.

In most embodiments, the donor and acceptor dyes for FRET are different, in which case FRET can be detected by the appearance of sensitized fluorescence of the acceptor and/or by quenching of donor fluorescence. When the donor and acceptor are the same, FRET is detected by the resulting fluorescence depolarization. FRET is dependent on the inverse sixth power of the intermolecular separation (Stryer et al., 1978, Ann. Rev. Biochem., 47:819; Selvin, 1995, Methods Enzymol., 246:300).

As used herein, the term "donor" refers to a fluorophore which absorbs at a first wavelength and emits at a second, longer wavelength. The term "acceptor" refers to a fluorophore, chromophore or quencher with an absorption spectrum which overlaps the donor's emission spectrum and is able to absorb some or most of the emitted energy from the donor when it is near the donor group (typically between 1-100 nm). If the acceptor is a fluorophore capable of exhibiting FRET, it then re-emits at a third, still longer wavelength; if it is a chromophore or quencher, then it releases the energy absorbed from the donor without emitting a photon. Although the acceptor's absorption spectrum overlaps the donor's emission spectrum when the two groups are in proximity, this need not be the case for the spectra of the molecules when free in solution. Acceptors thus include fluorophores, chromophores or quenchers which exhibit either FRET or quenching when placed in proximity, on a probe according to the invention, to the donor due to the presence of a probe secondary structure that changes upon binding of the probe to the target nucleic acid, as defined herein. Acceptors do not include fluorophores, chromophores or quenchers that exhibit FRET or quenching a) at temperatures equal to or greater than the Tm (e.g. more than 5° above the Tm, for example 6°, 10°, 25°, 50°or more above the Tm) or b) in the presence of a target nucleic acid.

Reference herein to "fluorescence" or "fluorescent groups" or "fluorophores" include luminescence, luminescent groups and suitable chromophores, respectively. Suitable luminescent probes include, but are not limited to, the luminescent ions of europium and terbium introduced as lanthium chelates (Heyduk & Heyduk, 1997). The lanthanide ions are also good donors for energy transfer to fluorescent groups (Selvin 1995). Luminescent groups containing lanthanide ions can be incorporated into nucleic acids utilizing an 'open cage' chelator phosphoramidite.

As used herein, the term "quenching" refers to the transfer of energy from donor to acceptor which is associated with a reduction of the intensity of the fluorescence exhibited by the donor.

The donor and acceptor groups may independently be selected from suitable fluorescent groups, chromophores and quenching groups. Donors and acceptors useful according to the invention include but are not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloylfluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl) -3,6-bis(dimethylamino); EDANS (5-((2-aminoethyl) amino)naphthalene-1-sulfonic acid); 1,5-IAEDANS (5-((((2-iodoacetyl)amino)ethyl) amino) naphthalene-1-sulfonic acid); DABCYL (4-((4-(dimethylamino)phenyl) azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), as well as suitable derivatives thereof.

In certain embodiments of the invention, a probe may also be labeled with two chromophores, and a change in the absorption spectra of the label pair is used as a detection signal, as an alternative to measuring a change in fluorescence.

In the method of the invention, fluorescence intensity of the probe is measured at one or more wavelengths with a fluorescence spectrophotometer or microtitre plate reader, according to methods known in the art.

C. Fluorescence Quenching Assay

A fluorescence quenching assay is useful in the invention for two purposes. The first is to determine whether the secondary structure of a probe is "stable" as defined herein. The second is to determine whether the secondary structure of the probe has undergone a "change" upon binding of the probe to the target nucleic acid.

A probe according to the invention is labeled with a pair of interactive labels (e.g., a FRET or non-FRET pair) wherein one member of the pair is a fluorophore and the other member of the pair is a quencher. For example, a probe according to the invention is labeled with a fluorophore and a quencher and fluorescence is measured in the absence of a target nucleic acid, over a range of temperatures, e.g., wherein the lower temperature limit of the range is at least 50° Celsius below, and the upper temperature limit of the range is at least 50° Celsius above the Tm or the predicted Tm of the probe.

D. Stability

The "stability" of the secondary structure of a probe according to the invention is determined as follows. A probe is labeled with a pair of interactive labels (for example, tetramethylrhodamine and DABCYL, or any of the interactive labels (either FRET or non-FRET pairs) described herein according to methods well known in the art (for example as described in Glazer and Mathies, 1997, $Curr. Opin. Biotechnol.$, 8:94; Ju et al., 1995, $Analytical Biochem.$, 231:131)). The location of the interactive labels on the probe is such that the labels are separated when the secondary structure of the probe changes following binding of the probe to the target nucleic acid.

Figure 12E:
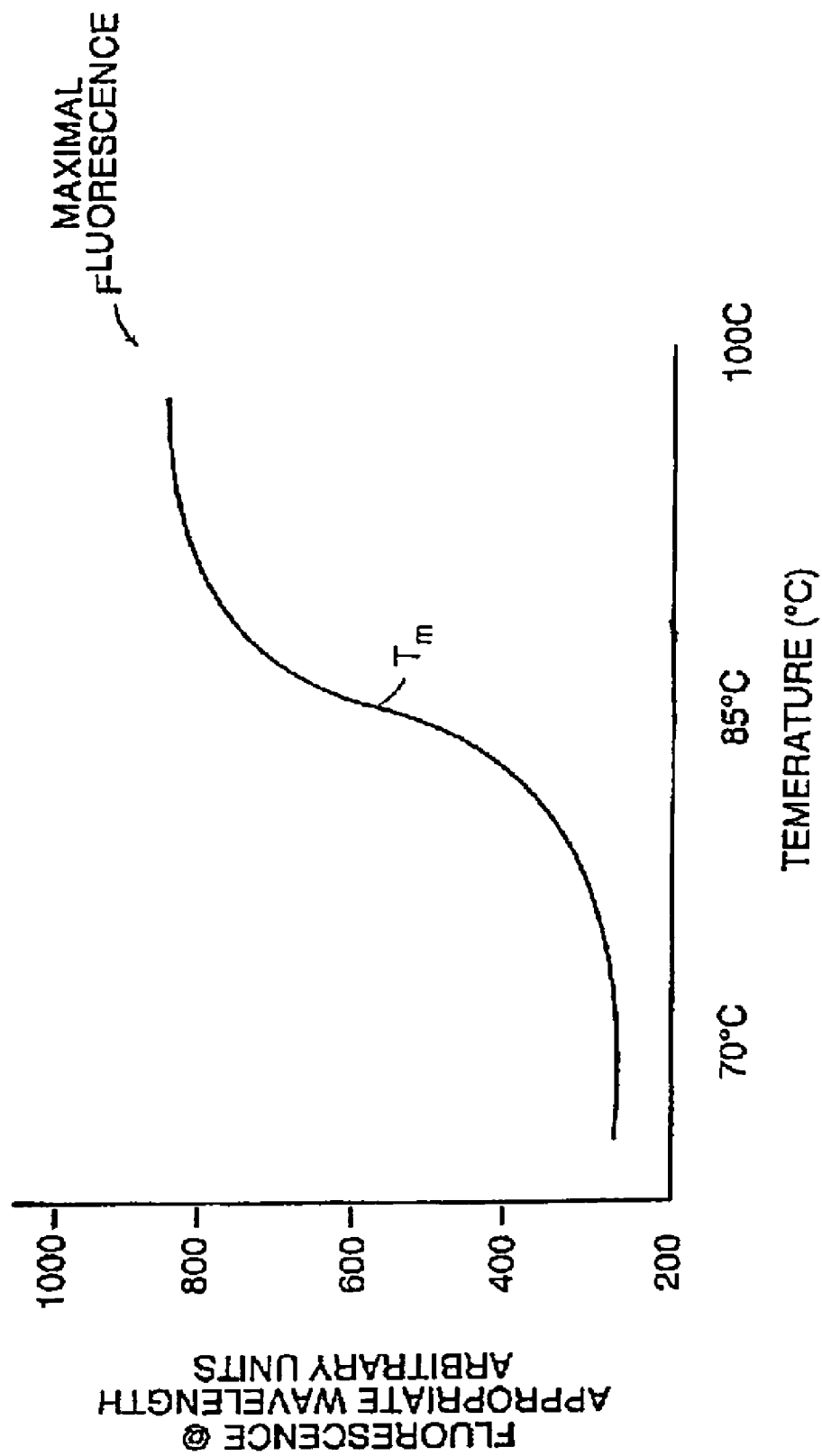
FIG. 12e is a graph demonstrating the effects of temperature on the fluorescence of DNA labeled with a pair of interactive labels.

A standard curve for the probe (for example FIG. 12e), wherein fluorescence is plotted versus temperature, is prepared by incubating a sample comprising typically 125 nM probe in 1× Melting Buffer (20 mM Tris-HCl, pH 8.0, 1 mM $MgCl_2$) or alternatively, in 5 mM Tris-HCl, pH 8.0, 0.1 mM EDTA, or other appropriate buffers for a time that is sufficient to permit denaturing and reannealing of the probe (typically the standard curve is generated using a fluorometer or spectrometer that undergoes a 1° C. per minute change, and measuring the fluorescence in a fluorometer or scanning fluorescence spectrophotometer over a range of temperatures wherein the lower temperature limit of the range is at least 50° C. below, and the upper temperature limit of the range is at least 50° C. above the Tm or predicted Tm of the probe. The Tm of the probe is predicted based on the base pair composition according to methods well known in the art (see, Sambrook, supra; Ausubel, supra).

Standard curves are generated and compared, using a variety of buffers (e.g., 1×TNE buffer (10×-0.1M Tris base, 10 mM EDTA, 2.0 M NaCl, pH 7.4), FEN nuclease buffer, described herein, 1× Cloned Pfu buffer, described herein, 1× Sentinel Molecular beacon buffer, described herein) including a buffer that is possible and preferentially optimal for the particular nuclease to be employed in the cleavage reaction. The pH of the buffer will be monitored as the temperature increases, and adjusted as is needed.

The temperature of the fluorometer or spectrophotometer can be controlled such that the fluorescence of the sample is measured at specific temperatures. Fluorescence can be measured for example with a Perkin-Elmer LS50B Luminescence Spectrometer in combination with a temperature regulatable water bath (e.g., for example available from Fisher Scientific)

Figure 12F:
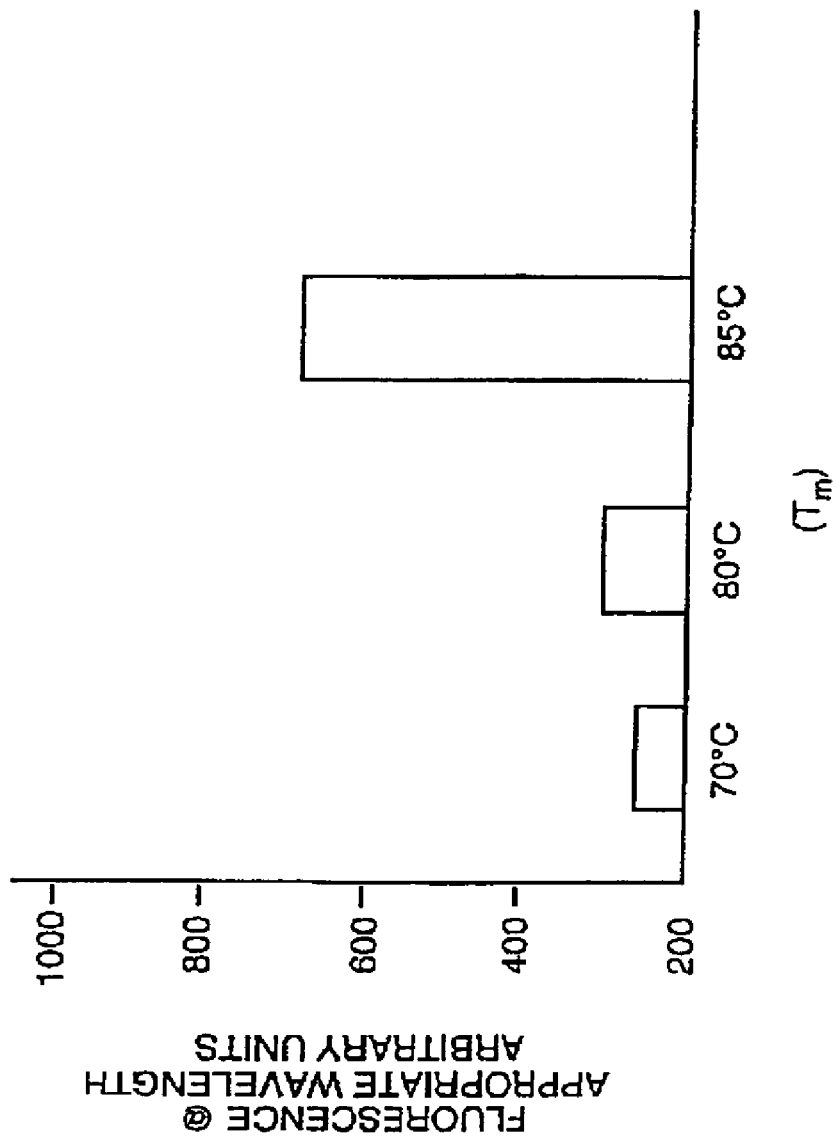
FIG. 12f is a graph demonstrating the effects of temperature on the fluorescence of DNA labeled with a pair of interactive labels.

The stability of the secondary structure of a probe at a particular temperature is determined by measuring the fluorescence of the probe at a particular temperature, as above, and determining if the value of the fluorescence is less than the fluorescence at the Tm, as determined from the standard curve. The secondary structure of the probe is "stable" in a FRET assay, at a temperature that is at or below the temperature of the cleavage reaction (i.e., at which cleavage is performed) if the level of fluorescence at the temperature at or below the temperature of the cleavage reaction is altered (i.e., at least 5%, preferably 20% and most preferably 25% more or less than) the level of fluorescence at a temperature that is equal to the Tm of the probe. The secondary structure of the probe is "stable" in a fluorescence quenching assay, at a temperature that is at or below the temperature of the cleavage reaction (i.e., at which cleavage is performed) if the level of fluorescence at the temperature at or below the temperature of the cleavage reaction is less (i.e., at least 5%, preferably 20% and most preferably 25% more or less than) the level of fluorescence at a temperature that is equal to the Tm of the probe (see FIGS. 12f and 12g).

Alternatively, the stability of the secondary structure of the probe is determined by modifying the method of Gelfand et al. (1999, Proc. Natl. Acad. Sci. USA, 96:6113), incorporated herein by reference, to determine the fluorescence of a probe labeled with a pair of interactive labels over a range of temperatures, as described hereinabove.

V. Detecting a Secondary Structure

A secondary structure according to the invention is detected by generating a standard curve of fluorescence versus temperature for a probe comprising a pair of interactive labels in a FRET or fluorescence quenching assay, as described above (see FIG. 12e). A probe that exhibits a change in fluorescence that correlates with a change in temperature (see FIG. 12e) (e.g., fluorescence increases as the temperature of the FRET reaction is increased) is capable of forming a secondary structure.

VI. Measuring a Change in Secondary Structure

A "change" in secondary structure according to the invention is detected by analyzing a probe comprising a pair of interactive labels in a FRET or fluorescence quenching assay at a particular temperature below the Tm of the probe, (e.g., the cleaving temperature), as described above, in the presence or absence of 100 nM to 10 µM of a target nucleic acid (typically the target nucleic acid is in a 2-4 molar excess over the probe concentration, i.e., 250-500 nM target nucleic acid is used).

Alternatively, a change in the secondary structure of the probe is determined by modifying the method of Gelfand et al. (1999, Proc. Natl. Acad. Sci. USA, 96:6113), incorporated herein by reference, to determine the fluorescence of a probe labeled with a pair of interactive labels in the presence or absence of a target nucleic acid as described hereinabove.

Figure 12G:
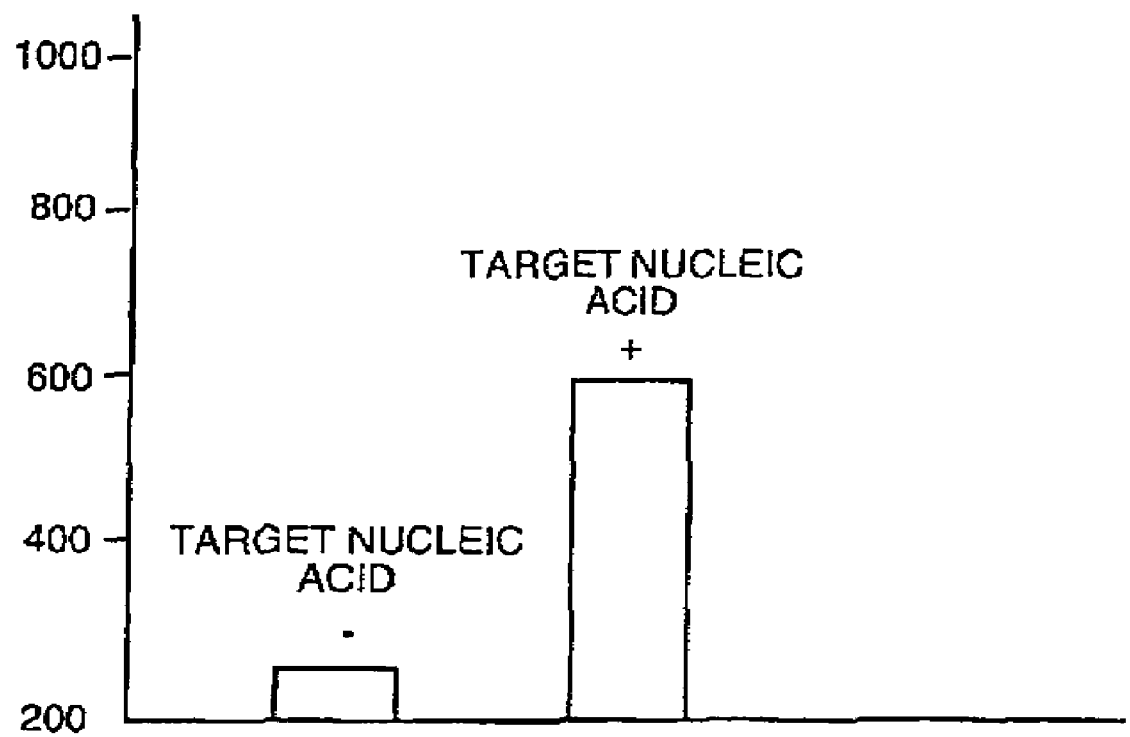
FIG. 12g is a graph demonstrating the effects of a target nucleic acid on the fluorescence of DNA labeled with a pair of interactive labels.

A "change" in secondary structure that occurs when a probe according to the invention binds to a target nucleic acid, is measured as an increase in fluorescence, such that the level of fluorescence after binding of the probe to the target nucleic acid at the temperature below the Tm of the probe, is greater than (e.g., at least 5%, preferably 5-20% and more preferably 25 or more) the level of fluorescence observed in the absence of a target nucleic acid (see FIG. 12g).

VII. Methods of Use

The invention provides for a method of generating a signal indicative of the presence of a target nucleic acid in a sample comprising the steps of forming a labeled cleavage structure by incubating a target nucleic acid with a probe having a secondary structure, as defined herein, that changes upon binding to a target nucleic acid and comprising a binding moiety, and cleaving the cleavage structure with a nuclease (e.g. a FEN nuclease). The method of the invention can be used in a PCR based assay as described below.

A labeled cleavage structure comprising an upstream oligonucleotide primer (for example A, FIG. 4), a 5' end labeled downstream oligonucleotide probe having a secondary structure that changes upon binding to a target nucleic acid and comprising a binding moiety (for example C in FIG. 4) and a target nucleic acid (for example B in FIG. 4) is formed as described above in the section entitled "Cleavage Structure". Briefly, a cleavage structure is formed and cleaved in the presence of a target nucleic acid, in the presence or absence of an upstream primer (for example A, FIG. 4), a labeled downstream probe as defined herein (for example C, FIG. 4) amplification primers specific for the target nucleic acid, a nucleic acid polymerase deficient in 5' to 3' exonuclease activity a nuclease (e.g. a FEN nuclease) and an appropriate buffer (for example 10×Pfu buffer, Stratagene, Catalog#200536) in a PCR reaction with the following thermocycling parameters: 95° C. for 2 minutes and 40 cycles of 95° C. for 15 sec (denaturation step), 60° C. for 60 sec (annealing step) and 72° C. for 15 sec (extension step). During this reaction an upstream oligonucleotide (for example A, FIG. 4) is extended such that oligonucleotide A partially displaces the 5' labeled end of a downstream oligonucleotide probe according to the invention (for example oligonucleotide C, FIG. 4) and the resulting labeled structure is cleaved with a nuclease (e.g., a FEN nuclease) according to the invention. Alternatively, a downstream probe comprising a secondary structure, as defined herein, (including a stem loop, a hairpin, an internal loop, a bulge loop, a branched structure and a pseudoknot) or multiple secondary structures, cloverleaf structures, or any three dimensional structure, as defined herein, can be used. Bi-molecular or multimolecular probes, as defined herein, can also be used. The released labeled fragment is captured by specific binding of the binding moiety to a capture element on a solid support according to methods well known in the art (see Sambrook et al., supra and Ausubel et al., supra). Alternatively, a cleavage structure can be formed and cleaved in the presence of a nucleic acid polymerase that possesses 5' to 3' exonuclease activity.

The methods of the invention can also be used in non-PCR based applications to detect a target nucleic acid, where such target may be immobilized on a solid support. Methods of immobilizing a nucleic acid sequence on a solid support are known in the art and are described in Ausubel F M et al. Current Protocols in Molecular Biology, John Wiley and Sons, Inc. and in protocols provided by the manufacturers, e.g. for membranes: Pall Corporation, Schleicher & Schuell, for magnetic beads: Dynal, for culture plates: Costar, Nalgenunc, and for other supports useful according to the invention, CPG, Inc. A solid support useful according to the invention includes but is not limited to silica based matrices, membrane based matrices and beads comprising surfaces including, but not limited to any of the solid supports described above in the section entitled, "Cleavage Structure" and including styrene, latex or silica based materials and other polymers. Magnetic beads are also useful according to the invention. Solid supports can be obtained from the above manufacturers and other known manufacturers.

The invention also provides for a non-PCR based assay for detecting a target nucleic acid in solution. The method of the invention can be used to detect naturally occurring target nucleic acids in solution including but not limited to RNA and DNA that is isolated and purified from cells, tissues, single cell organisms, bacteria or viruses. The method of the invention can also be used to detect synthetic targets in solution, including but not limited to RNA or DNA oligonucleotides, and peptide nucleic acids (PNAs). Non-PCR assays include but are not limited to detection assays involving isothermal linear or exponential amplification, where the amount of nucleic acid synthesized by the 3'-5' synthetic activity increases linearly or exponentially, and a nuclease (e.g. a FEN nuclease) is used to cleave the displaced strand during synthesis. One such example utilizes rolling circle amplification.

In one embodiment of the invention, detection of a nucleic acid target sequence that is either immobilized or in solution can be performed by incubating an immobilized nucleic acid target sequence or a target nucleic acid in solution with an upstream oligonucleotide primer that is complementary to the target nucleic acid (for example A, FIG. 4) and a downstream oligonucleotide probe having a secondary structure that changes upon binding to a target nucleic acid and comprising a binding moiety, that is complementary to the target nucleic acid (for example C, FIG. 4), a nuclease (e.g. a FEN nuclease) and a nucleic acid polymerase that possesses or lacks 5' to 3' exonuclease activity. The downstream probe is either end labeled at the 5' or 3' end, or is labeled internally. Alternatively, a downstream probe comprising a secondary structure, as defined herein, (including a stem loop, a hairpin, an internal loop, a bulge loop, a branched structure and a pseudoknot) or multiple secondary structures, cloverleaf structures, or any three dimensional structure, as defined herein, can be used. Bi-molecular or multimolecular probes, as defined herein, can also be used. Detection of a released labeled fragment that is captured by binding of the binding moiety to a capture element involves isotopic, enzymatic, or colorimetric methods appropriate for the specific label that has been incorporated into the probe and well known in the art (for example, Sambrook et al., supra, Ausubel et al., supra). Labels useful according to the invention and methods for the detection of labels useful according to the invention are described in the section entitled "Cleavage Structure". Alternatively, the downstream probe further comprises a pair of interactive signal generating labeled moieties (for example a dye and a quencher) that are positioned such that when the probe is intact, the generation of a detectable signal is quenched, and wherein the pair of interactive signal generating moieties are separated by a nuclease cleavage site (e.g. a FEN nuclease cleavage site). In another embodiment, the downstream probe further comprises a pair of interactive signal generating labeled moieties (for example a dye and a quencher) that are positioned such that when the probe is not hybridized to the target nucleic acid, the generation of a detectable signal is quenched. Upon cleavage by a nuclease (e.g. a FEN nuclease), the two signal generating moieties are separated from each other and a detectable signal is produced. The presence of a pair of interactive signal generating labeled moieties, as described above, allows for discrimination between annealed, uncleaved probe that may bind to a capture element, and released labeled fragment that is bound to a capture element. Nucleic acid polymerases that are useful for detecting an immobilized nucleic acid target sequence or a nucleic acid target sequence in solution according to the method of the invention include mesophilic, thermophilic or hyper-thermophilic DNA polymerases lacking 5' to 3' exonucleolytic activity (described in the section entitled, "Nucleic Acid Polymerases)". Any nucleic acid polymerase that possess 5' to 3' exonuclease activity is also useful according to the invention.

According to this non-PCR based method, the amount of a target nucleic acid that can be detected is preferably about 1 pg to 1 µg, more preferably about 1 pg to 10 ng and most preferably about 1 pg to 10 pg. Alternatively, this non-PCR based method can measure or detect preferably about 1 molecule to $10^{20}$ molecules, more preferably about 100 molecules to $10^{17}$ molecules and most preferably about 1000 molecules to $10^{14}$ molecules.

The invention also provides for a method of detecting a target nucleic acid in a sample wherein a cleavage structure is formed as described in the section entitled, "Cleavage Structure"; and the target nucleic acid is amplified by a non-PCR based method including but not limited to an isothermal method, for example rolling circle, Self-sustained Sequence Replication Amplification (3SR), Transcription based amplification system (TAS), and Strand Displacement Amplification (SDA) and a non-isothermal method, for example Ligation chain reaction (LCR). A nuclease (e.g., a FEN nuclease) useful for non-PCR amplification methods will be active at a temperature range that is appropriate for the particular amplification method that is employed.

In the amplification protocols described below, samples which need to be prepared in order to quantify the target include: samples, no-template controls, and reactions for preparation of a standard curve (containing dilutions over the range of six orders of magnitude of a solution with a defined quantity of target).

Strand Displacement Amplification (SDA) is based on the ability of a restriction enzyme to nick the unmodified strand of a hemiphosphorothioate form of its recognition site. The appropriate DNA polymerase will initiate replication at this nick and displace the downstream non-template strand (Walker, 1992, Proc. Natl. Acad. Sci. USA, 89: 392, and PCR Methods and Applications 3: 1-6, 1993). The polymerases (Bca and Bst) which are used according to the method of SDA can also be used in nuclease (e.g. FEN nuclease) directed cleavage according to the invention. According to the method of the invention, a molecular beacon is replaced by a nuclease (e.g., a FEN nuclease) active at 42° C. and a cleavable probe having a secondary structure that changes upon binding to a target nucleic acid and further comprising a binding moiety, and comprising a cleavage structure according to the invention.

A molecular beacon (Mb) is a fluorogenic probe which forms a stem-loop structure is solution. Typically: 5'-fluorescent dye (e.g. FAM); attached to the 5'-stem region (5-7 nt), the loop region (complementary to the target, 20 to 30 nt), the 3'-stem region (complementary to the 5'-stem region), and the quencher (e.g. DABCYL). If no target is present, the MB forms its stem, which brings dye and quencher into close proximity, and therefore no fluorescence is emitted. When an MB binds to its target, the stem is opened, dye is spatially separated from the quencher, and therefore the probe emits fluorescence (Tyagi S and Kramer FR, Nature Biotechnology 14: 303-308 (1996) and U.S. Pat. No. 5,925,517).

Strand Displacement Amplification (SDA) is essentially performed as described by Spargo et al., Molecular and Cellular Probes 10: 247-256 (1996). The enzymes used include restriction endonuclease BsoBI (New England Biolabs), DNA polymerase 5'-exo- Bca (PanVera Corporation). The target is an insertion-like element (IS6110) found in the *Mycobacterium tuberculosis* (Mtb) genome. The primers used are B1: cgatcgagcaagcca, B2: cgagccgctcgctg, S1: accgcatcgaatgcatgtctcgggtaaggcgtactcgacc and S2: cgattccgctccagacttctcgggtgtactgagatcccct. The *Mycobacterium tuberculosis* genomic DNA is serially diluted in human placental DNA. SDA is performed in 50 µl samples containing 0 to 1000 Mtb genome equivalents, 500 ng human placental DNA, 160 units BsoB1, 8 units of 5'-exo- Bca, 1.4 mM each dCTPalphaS, TTP, dGTP, dATP, 35 mM $K_2PO_4$, pH 7.6 0.1 mg/ml acetylated bovine serum albumin (BSA), 3 mM Tris-HCl, 10 mM $MgCl_2$, 11 mM NaCl, 0.3 mM DTT, 4 mM KCl, 4% glycerol, 0.008 mM EDTA, 500 nM primers S1 and S2 and 50 nM primers B1 and B2 (KCl, glycerol and EDTA are contributed by the BsoB1 storage solution). The samples (35 µl) were heated in a boiling water bath for 3 minutes before the addition of BsoB1 and 5'-exo Bca (10.7 units/µl BsoB1 and 0.53 units/µl 5'-exo Bca in 15 µl of New England Biolabs Buffer 2 (20 mM Tris-HCl pH 7.9, 10 mM $MgCl_2$, 50 mM NaCl, 1 mM DTT). Incubation is at 60° C. for 15 minutes, followed by 5 minutes in a boiling water bath.

Five μl of each sample in duplicate are removed for detection. Each reaction contains 1× Cloned Pfu buffer, 3.0 mM MgCl$_2$, 200 μM of each dNTP, 5 units exo-Pfu, 23 ng Pfu FEN-1, 1 ng PEF, 300 nM each upstream primer: aaggcg-tactcgacctgaaa and fluorogenic probe (for example FAM-DABCYL): accatacggataggggatctc. The reactions are subjected to one cycle in a thermal cycler: 2 minutes at 95° C., 1 minute at 55° C., 1 minute at 72° C. The fluorescence is then determined in a fluorescence plate reader, such as Stratagene's FluorTracker or PE Biosystems' 7700 Sequence Detection System in Plate-Read Mode. The method of the invention can also be performed with a polymerase that exhibits 5' to 3' exonuclease activity and any nuclease included in the section entitled, "Nucleases".

According to the method of nucleic acid sequence-based amplification (NASBA), molecular beacons are used for quantification of the NASBA RNA amplicon in real-time analysis (Leone, et al., 1998, *Nucleic Acids Res.* 26: 2150). According to the method of the invention, NASBA can be carried out wherein the molecular beacon probe is replaced by a nuclease (e.g. a FEN nuclease) cleavable probe having a secondary structure that changes upon binding to a target nucleic acid and comprising a binding moiety, and further comprising a cleavage structure according to the invention and a nuclease (e.g. a FEN nuclease) active at 41° C.

NASBA amplification is performed essentially as described by Leone G, et al., Nucleic Acids Res. 26: 2150-2155 (1998). Genomic RNA from the potato leafroll virus (PLRV) is amplified using the PD415 or PD416 (antisense) and the PD417 (sense) primers, which are described in detail in Leone G et al., J. Virol. Methods 66: 19-27 (1997). Each NASBA reaction contains a premix of 6 μl of sterile water, 4 μl of 5×NASBA buffer (5×NASBA buffer is 200 mM Tris-HCl, pH 8.5, 60 mM MgCl$_2$, 350 mM KCl, 2.5 mM DTT, 5 mM each of dNTP, 10 mM each of ATP, UTP and CTP, 7.5 mM GTP and 2.5 mM ITP), 4 μl of 5× primer mix (75% DMSO and 1 μM each of antisense and sense primers). The premix is divided into 14 μl aliquots, to which 1 μl of PLRV target is added. After incubation for 5 minutes at 65° C. and cooling to 41° C. for 5 minutes, 5 μl of enzyme mix is added (per reaction 375 mM sorbitol, 2.1 μg BSA, 0.08 units of RNase H (Pharmacia), 32 units of T7 RNA polymerase (Pharmacia) and 6.4 units of AMV-RT (Seigakaku)). Amplification is for 90 minutes at 41° C.

Five μl of each sample in duplicate are removed for detection. Each reaction contains 1× Cloned Pfu buffer, 3.0 mM MgCl$_2$, 200 μM of each dNTP, 5 units exo-Pfu, 23 ng Pfu FEN-1, 1 ng PEF, 300 nM each upstream primer PD415 or PD416 and the fluorogenic probe (for example FAM-DABCYL): gcaaagtatcatccctccag. The reactions are subjected to one cycle in a thermal cycler: 2 minutes at 95° C., 1 minute at 55° C., 1 minute at 72° C. The fluorescence in then determined in a fluorescence plate reader, such as Stratagene's FluorTracker or PE Biosystems' 7700 Sequence Detection System in Plate-Read Mode.

Generally, according to these methods wherein amplification occurs by a non-PCR based method, amplification may be carried out in the presence of a nuclease (e.g. a FEN nuclease), and amplification and cleavage by the nuclease (e.g. a FEN nuclease) occur simultaneously. Detection of released labeled fragments captured by binding of a binding moiety to a capture element on a solid support is performed as described in the section entitled "Cleavage Structure" and may occur concurrently with (real time) or after (end-point) the amplification and cleavage process have been completed.

Endpoint assays can be used to quantify amplified target produced by non-PCR based methods wherein the amplification step is carried out in the presence of a nuclease (e.g., a FEN nuclease) (described above).

Endpoint assays include, but are not limited to the following.

A. Ligation chain reaction (LCR), as described in Landegren, et al., 1988, *Science,* 241: 1077 and Barany, PCR Methods and Applications 1: 5-16 (1991). An LCR product useful according to the invention will be long enough such that the upstream primer and the labeled downstream probe are separated by a gap larger than 8 nucleotides to allow for efficient cleavage by a nuclease (e.g. a FEN nuclease).

B. Self-sustained sequence replication amplification (3SR) Fahy, et al. PCR Methods and Applications 1: 25-33 (1991). Self-Sustained Sequence Replication Amplification (3SR) is a technique which is similar to NASBA. Ehricht R, et al., Nucleic Acids Res. 25: 4697-4699 (1997) have evolved the 3SR procedure to a cooperatively coupled in vitro amplification system (CATCH). Thus, in one embodiment of the invention, a molecular beacon probe is used for real-time analysis of an RNA amplicon by CATCH. The synthetic target amplified has the sequence: cctctgcagactactattacataataca-gagactcactatagggatctgcacgtattagcctatagtgagtcgtattaataggaa-acaccaaagatgatatttcgtcacagcaagaattcagg. The 3SR reactions contain 40 mM Tris-HCl pH 8.0, 5 mM KCl, 30 mM MgCl$_2$, 1 mM of each dNTP, 1 nM of the double stranded target, 2 μM P1: cctctgcagactactattac and P2:cctgaattcttgctgtgacg, 5 mM DTT, 2 mM spermidine, 6 units/ul His tagged HIV-1 reverse transcriptase, 3 units/ul T7-RNA polymerase and 0.16 units/ul *Escherichia coli* RNase H. The 100 ul reactions are incubated for 30 minutes at 42° C.

Five μl of each sample in duplicate are removed for detection. Each reaction contains 1× Cloned Pfu buffer, 3.0 mM MgCl$_2$, 200 μM of each dNTP, 5 units exo-Pfu, 23 ng Pfu FEN-1, 1 ng PEF, 300 nM each upstream primer P1 and fluorogenic probe (for example FAM-DABCYL): taggaaa-caccaaagatgatattt. The reactions are subjected to one cycle in a thermal cycler: 2 minutes at 95° C., 1 minute at 55° C., 1 minute at 72° C. The fluorescence in then determined in a fluorescence plate reader, such as Stratagene's FluorTracker or PE Biosystems' 7700 Sequence Detection System in Plate-Read Mode. The method of 3SR can also be carried out with a polymerase that exhibits 5' to 3' exonuclease activity and any nuclease described in the section entitled, "Nucleases".

C. Rolling circle amplification is described in U.S. Pat. No. 5,854,033 and the related Ramification-Extension Amplification Method (RAM) (U.S. Pat. No. 5,942,391). Rolling circle amplification adapted to the invention is described below.

Real-time assays can also be used to quantify amplified target produced by non-PCR based methods wherein the amplification step is carried out in the presence of a nuclease (e.g. a FEN nuclease) (described above). The method of rolling circle amplification (U.S. Pat. No. 5,854,033) is adapted to include secondary primers for amplification and detection; in conjunction with a nuclease (e.g. a FEN nuclease) and a cleavable probe having a secondary structure that changes upon binding to a target nucleic acid and comprising a binding moiety, and further comprising a cleavage structure according to the invention, and is carried out at temperatures between 50-60° C. The cleavage pattern of a nuclease (e.g. a FEN nuclease) can be altered by the presence of a single mismatched base located anywhere between 1 and 15 nucleotides from the 5' end of the primer wherein the DNA primer is otherwise fully annealed. Typically, on a fully annealed substrate, a nuclease (e.g. a FEN nuclease) will exonucleolytically cleave the 5' most nucleotide. However, a single nucleotide mismatch up to 15 nucleotides in from the 5' end promotes endonucleolytic cleavages. This constitutes a 5' proofreading process in which the mismatch promotes the nuclease action that leads to its removal. Thus, the mechanism of nuclease (e.g. FEN nuclease) cleavage is shifted from predominantly exonucleolytic cleavage to predominantly endonucleolytic cleavage simply by the presence of a single mismatched base pair. Presumably this occurs because a mismatch allows a short flap to be created (Rumbaugh et al., 1999, *J. Biol. Chem.*, 274:14602).

The method of the invention can be used to generate a signal indicative of the presence of a sequence variation in a target nucleic acid, wherein a labeled cleavage structure comprising a fully annealed DNA primer is formed by incubating a target nucleic acid with a probe having a secondary structure that changes upon binding to a target nucleic acid and comprising a binding moiety (as described in the section entitled, "Cleavage Structure") and cleaving the labeled cleavage structure with a nuclease (e.g. a FEN nuclease) wherein the release of labeled fragments comprising endonucleolytic cleavage products, and the detection of released fragments that are captured by binding of a binding moiety to a capture element on a solid support, is indicative of the presence of a sequence variation. Released labeled fragments are detected as described in the section entitled, "Cleavage Structure".

V. Samples

The invention provides for a method of detecting or measuring a target nucleic acid in a sample, as defined herein. As used herein, "sample" refers to any substance containing or presumed to contain a nucleic acid of interest (a target nucleic acid) or which is itself a target nucleic acid, containing or presumed to contain a target nucleic acid of interest. The term "sample" thus includes a sample of target nucleic acid (genomic DNA, cDNA or RNA), cell, organism, tissue, fluid or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

EXAMPLES

The invention is illustrated by the following nonlimiting examples wherein the following materials and methods are employed. The entire disclosure of each of the literature references cited hereinafter are incorporated by reference herein.

Example 1

Probe Design and Preparation

The invention provides for a probe having a secondary structure that changes upon binding of the probe to a target nucleic acid and comprising a binding moiety.

A probe according to one embodiment of the invention is 5-250 nucleotides in length and ideally 17-40 nucleotides in length, and has a target nucleic acid binding sequence that is from 7 to about 140 nucleotides, and preferably from 10 to about 140 nucleotides. Probes may also comprise non-covalently bound or covalently bound subunits.

Figure 4:
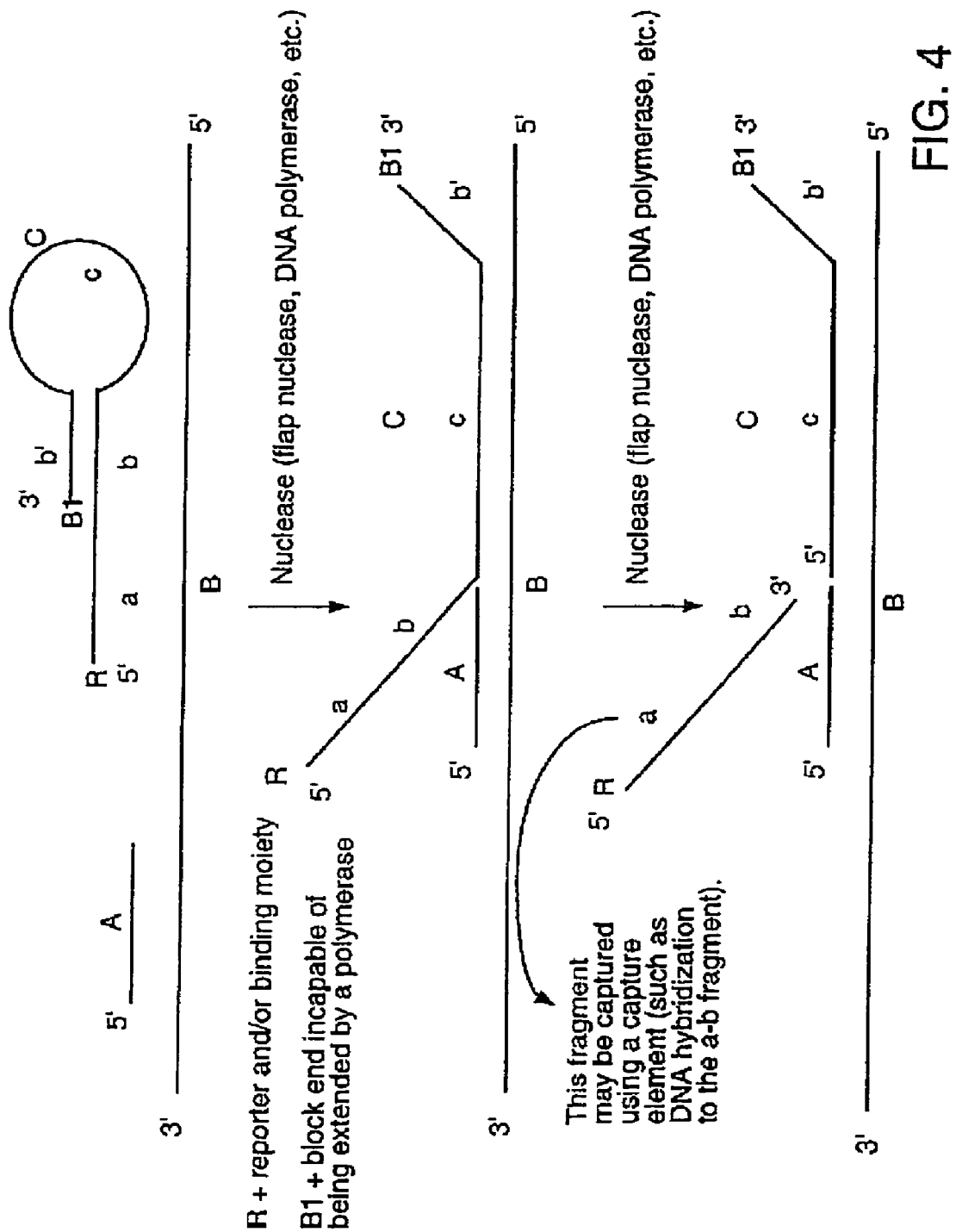
FIG. 4 is a diagram illustrating a synthesis and cleavage reaction to generate a signal according to the invention.

One embodiment of a probe comprises a first complementary nucleic acid sequence (for example, b in FIG. 4) and a second complementary nucleic acid sequence (for example, b' in FIG. 4). In one embodiment wherein the probe is unimolecular, the first and second complementary nucleic acid sequences are in the same molecule. In one embodiment, the probe is labeled with a fluorophore and a quencher (for example, tetramethylrhodamine and DABCYL, or any of the fluorophore and quencher molecules described herein (see the section entitled "How To Prepare a Labeled Cleavage Structure"). A probe according to the invention is labeled with an appropriate pair of interactive labels (e.g., a FRET pair or a non-FRET pair). The location of the interactive labels on the probe is such that an appropriate spacing of the labels on the probe is maintained to permit the separation of the labels when the probe undergoes a change in the secondary structure of the probe upon binding to a target nucleic acid. For example, the donor and quencher moieties are positioned on the probe to quench the generation of a detectable signal when the probe is not bound to the target nucleic acid.

The probe further comprises a binding moiety (for example ab in FIG. 4, comprising a nucleic acid sequence, i.e., 5'AGC-TACTGATGCAGTCACGT3'). In one embodiment of the invention, upon hybridization to a target nucleic acid, the probe according to the invention, forms a cleavage structure comprising a 5' flap (e.g., ab in FIG. 4). The flap of the cleavage structure thus comprises the binding moiety of the probe. Cleaving is performed at a cleaving temperature, and the secondary structure of the probe when not bound to the target nucleic acid is stable at or below the cleaving temperature. Upon cleavage of the hybridized probe by a nuclease, the binding moiety is released and binds specifically to a capture element comprising a nucleic acid sequence, i.e., 5'TCGAT-GACTACGTCAGTGCA3'. According to this embodiment, the binding moiety comprises two regions (for example a and b in FIG. 4). The region of a "binding moiety" that is not a "complementary nucleic acid sequence", as defined herein, (e.g., a in FIG. 4), is from 1-60 nucleotides, preferably from 1-25 nucleotides and most preferably from 1-10 nucleotides in length. Region b is one of at least two complementary nucleic acid sequences of the probe, as defined herein, the length of which is described in detail below.

In one embodiment, in the absence of the target nucleic acid the probe folds back on itself to generate an antiparallel duplex structure wherein the first and second complementary nucleic acid sequences anneal by the formation of hydrogen bonds to form a secondary structure. The secondary structure of the probe is detected by performing a FRET or fluorescence quenching assay at different temperatures, including temperatures that are above and below the Tm of the probe, as described herein. A probe that exhibits a change in fluorescence that correlates with a change in temperature (e.g., fluorescence increases as the temperature of the FRET reaction is increased), greater than a change in fluorescence simply due to thermal effects on the efficiency of fluorophore emission, has secondary structure. Secondary structure is eliminated at a temperature wherein the maximal level of fluorescence is detected (e.g., fluorescence does not increase above this level at increased temperatures). The stability of the secondary structure of the probe is determined in a melting temperature assay or by FRET or fluorescence quenching assay, as described herein.

As a result of the change in the secondary structure of the probe, the binding moiety becomes accessible for cleavage by a nuclease. In the presence of the target nucleic acid, and at a temperature that is selected according to the factors that influence the efficiency and selectivity of hybridization of the probe to the target nucleic acid, (e.g., primer length, nucleotide sequence and/or composition, buffer composition, as described in the section entitled, "Primers and Probes Useful According to the Invention") to permit specific binding of the probe and the target nucleic acid, the probe binds to the target nucleic acid and undergoes a change in the secondary structure. A change in the secondary structure of the probe can be determined by FRET or fluorescence quenching, as described herein.

In one embodiment, first and second complementary nucleic acid sequences are 3-25, preferably 4-15 and more preferably 5-11 nucleotides long. The length of the first and second complementary nucleic acid sequences is selected such that the secondary structure of the probe when not bound to the target nucleic acid is stable at the temperature at which cleavage of a cleavage structure comprising the probe bound to a target nucleic acid is performed. As the target nucleic acid binding sequence increases in size up to 100 nucleotides, the length of the complementary nucleic acid sequences may increase up to 15-25 nucleotides. For a target nucleic acid binding sequence greater than 100 nucleotides, the length of the complementary nucleic acid sequences are not increased further.

Alternatively, an allele discriminating probe having secondary structure and comprising a binding moiety is prepared.

In one embodiment, an allele discriminating probe according to the invention preferably comprises a target nucleic acid binding sequence from 6 to 50 and preferably from 7 to 25 nucleotides, and sequences of the complementary nucleic acid sequences from 3 to 8 nucleotides. The guanosine-cytidine content of the secondary structure and probe-target hybrids, salt, and assay temperature are considered, for example magnesium salts have a strong stabilizing effect, when designing short, allele-discriminating probes.

An allele-discriminating probe with a target nucleic acid binding sequence near the upper limits of 50 nucleotides long, is designed such that the single nucleotide mismatch to be discriminated against occurs at or near the middle of the target nucleic acid binding sequence. For example, probes comprising a sequence that is 21 nucleotides long are preferably designed so that the mismatch occurs opposite one of the 14 most centrally located nucleotides of the target nucleic acid binding sequence and most preferably opposite one of the 7 most centrally located nucleotides.

Example 2

Probe Design and Preparation

The invention provides for a probe having a secondary structure that changes upon binding of the probe to a target nucleic acid and comprising a binding moiety.

A probe according to one embodiment of the invention is 5-250 nucleotides in length and ideally 17-40 nucleotides in length, and has a target nucleic acid binding sequence that is from 7 to about 140 nucleotides, and preferably from 10 to about 140 nucleotides. Probes may also comprise non-covalently bound or covalently bound subunits.

One embodiment of a probe comprises a first complementary nucleic acid sequence (for example, b in FIG. 4) and a second complementary nucleic acid sequence (for example, b' in FIG. 4). In one embodiment wherein the probe is unimolecular, the first and second complementary nucleic acid sequences are in the same molecule. In one embodiment, the probe is labeled with a fluorophore and a quencher (for example, tetramethylrhodamine and DABCYL, or any of the fluorophore and quencher molecules described herein (see the section entitled "How To Prepare a Labeled Cleavage Structure"). A probe according to the invention is labeled with an appropriate pair of interactive labels (e.g., a FRET pair or a non-FRET pair). The location of the interactive labels on the probe is such that an appropriate spacing of the labels on the probe is maintained to permit the separation of the labels when the probe undergoes a change in the secondary structure of the probe upon binding to a target nucleic acid. For example, the donor and quencher moieties are positioned on the probe to quench the generation of a detectable signal when the probe is not bound to the target nucleic acid.

The probe further comprises a tag comprising the lac repressor protein. In one embodiment of the invention, upon hybridization to a target nucleic acid, the probe forms a cleavage structure comprising a 5' flap (e.g., ab in FIG. 4). Cleaving is performed at a cleaving temperature, and the secondary structure of the probe when not bound to the target nucleic acid is stable at or below the cleaving temperature. Upon cleavage of the hybridized probe by a nuclease, the lac repressor protein binds specifically to a capture element comprising the double stranded DNA sequence recognized and bound specifically by the lac repressor protein:

AATTGTGAGCGGATAACAATT

TTAACACTCGCCTATTGTTAA.

In one embodiment, in the absence of the target nucleic acid the probe folds back on itself to generate an antiparallel duplex structure wherein the first and second complementary nucleic acid sequences anneal by the formation of hydrogen bonds to form a secondary structure. The secondary structure of the probe is detected by performing a FRET or fluorescence quenching assay at different temperatures, including temperatures that are above and below the Tm of the probe, as described herein. A probe that exhibits a change in fluorescence that correlates with a change in temperature (e.g., fluorescence increases as the temperature of the FRET reaction is increased), greater than a change in fluorescence simply due to thermal effects on the efficiency of fluorophore emission, has secondary structure. Secondary structure is eliminated at a temperature wherein the maximal level of fluorescence is detected (e.g., fluorescence does not increase above this level at increased temperatures). The stability of the secondary structure of the probe is determined in a melting temperature assay or by FRET or fluorescence quenching assay, as described herein.

As a result of the change in the secondary structure of the probe, the tag becomes accessible for cleavage by a nuclease. In the presence of the target nucleic acid, and at a temperature that is selected according to the factors that influence the efficiency and selectivity of hybridization of the probe to the target nucleic acid, (e.g., primer length, nucleotide sequence and/or composition, buffer composition, as described in the section entitled, "Primers and Probes Useful According to the Invention") to permit specific binding of the probe and the target nucleic acid, the probe binds to the target nucleic acid and undergoes a change in the secondary structure. A change in the secondary structure of the probe can be determined by FRET or fluorescence quenching, as described herein.

In one embodiment, first and second complementary nucleic acid sequences are 3-25, preferably 4-15 and more preferably 5-11 nucleotides long. The length of the first and second complementary nucleic acid sequences is selected such that the secondary structure of the probe when not bound to the target nucleic acid is stable at the temperature at which cleavage of a cleavage structure comprising the probe bound to a target nucleic acid is performed. As the target nucleic acid binding sequence increases in size up to 100 nucleotides, the length of the complementary nucleic acid sequences may increase up to 15-25 nucleotides. For a target nucleic acid binding sequence greater than 100 nucleotides, the length of the complementary nucleic acid sequences are not increased further.

Alternatively, an allele discriminating probe having secondary structure and comprising a binding moiety is prepared.

In one embodiment, an allele discriminating probe according to the invention preferably comprises a target nucleic acid binding sequence from 6 to 50 and preferably from 7 to 25 nucleotides, and sequences of the complementary nucleic acid sequences from 3 to 8 nucleotides. The guanosine-cytidine content of the secondary structure and probe-target hybrids, salt, and assay temperature are considered, for example magnesium salts have a strong stabilizing effect, when designing short, allele-discriminating probes.

An allele-discriminating probe with a target nucleic acid binding sequence near the upper limits of 50 nucleotides long, is designed such that the single nucleotide mismatch to be discriminated against occurs at or near the middle of the target nucleic acid binding sequence. For example, probes comprising a sequence that is 21 nucleotides long are preferably designed so that the mismatch occurs opposite one of the 14 most centrally located nucleotides of the target nucleic acid binding sequence and most preferably opposite one of the 7 most centrally located nucleotides.

Example 3

A target nucleic acid can be detected and/or measured by the following method. A labeled cleavage structure is formed prior to the addition of a FEN nuclease by heating at 95° C. for 5 minutes and then cooling to approximately 50-60° C. (a) a sample containing a target nucleic acid (B in FIG. 4) with (b) an upstream oligonucleotide that specifically hybridizes to the target nucleic acid, (A, in FIG. 4), and (c) a downstream, 5' end labeled oligonucleotide probe having a secondary structure that changes upon binding of the probe to the target nucleic acid and comprising a binding moiety (for example ab in FIG. 4, comprising a nucleic acid sequence, i.e., 5'AGCTACTGATGCAGTCACGT3'), wherein the probe specifically hybridizes to a region of the target nucleic acid that is downstream of the hybridizing region of oligonucleotide A. A polymerase that lacks a 5' to 3' exonuclease activity but that possesses a 3' to 5' DNA synthetic activity, such as the enzyme a) Yaq exo-, (prepared by mutagenesis using the Stratagene QuikChange Site-Directed Mutagenesis kit, catalog number #200518, to modify Taq polymerase (Tabor and Richardson, 1985, Proc. Natl. Acad. Sci. USA, 82:1074)), a mutant form of Taq polymerase that lacks 5' to 3' exonuclease activity, b) Pfu, or c) a mutant form of Pfu polymerase that lacks 3' to 5' exonuclease activity (exo-Pfu) is added and incubated under conditions that permit the polymerase to extend oligonucleotide A such that it partially displaces the 5' end of oligonucleotide C (for example 72° C. in 1×Pfu buffer (Stratagene) for 5 minutes to 1 hour. The displaced region of oligonucleotide C forms a 5' flap that is cleaved upon the addition of a FEN nuclease. Alternatively, extension is performed with a polymerase that exhibits 5' to 3' exonuclease activity and with any nuclease included in the section entitled, "Nucleases".

A mutant form of Taq polymerase that lacks a 5' to 3' exonuclease activity but that possesses a 3' to 5' DNA synthetic activity comprises the following mutation: D144S/F667Y Taq wherein D144S eliminates 5' to 3' exonuclease activity and F667Y improves ddNTP incorporation.

Exo- mutants of PolI polymerase can be prepared according to the method of Xu et al., 1997, *J. Mol. Biol.*, 268: 284.

A labeled cleavage structure according to the invention is cleaved with a preparation of PfuFEN-1 (i.e. cloned *Pyrococcus furiosus* FEN-1 that is prepared as described below in Example 9). Cleaving is performed at a cleaving temperature, and the secondary structure of the probe when not bound to the target nucleic acid is stable at or below the cleaving temperature. Cleavage is carried out by adding 2 μl of PfuFEN-1 to a 7 μl reaction mixture containing the following:

| | |
|---|---|
| 3 μl | cleavage structure (10 ng-10 μg) |
| 0.7 μl | 10x FEN nuclease buffer (10X FEN nuclease buffer contains 500 mM Tris-HCl pH 8.0, 100 mM MgCl$_2$) |
| 2.00 μl | PfuFEN-1 enzyme or H$_2$O |
| 1.3 μl | H$_2$O |
| 7.00 μl | total volume |

Samples are incubated for one hour at 50° C. in a Robocyler 96 hot top thermal cycler. Following the addition of 2 μl of Sequencing Stop dye solution (included in the Stratagene Cyclist DNA sequencing kit, catalog #200326), samples are heated at 99° C. for five minutes. Released, labeled, fragments comprising the binding moiety are bound via binding of the binding moiety to a capture element comprising a nucleic acid sequence, i.e., 5'TCGATGACTACGTCAGTGCA3', on a solid support. In one embodiment, the labeled fragments are eluted from the capture element by, for example, decreasing the salt concentration (stringent hybridization conditions typically include salt concentrations of less than about 1M, more usually less than about 500 mM and preferably less than about 200 mM) or by adding an excess of unlabeled, competitor fragment. Samples containing eluted labeled fragments are analyzed by gel electrophoresis as follows. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80° C.). The gel is exposed overnight to X-ray film to detect the presence of a signal that is indicative of the presence of a target nucleic acid.

Alternatively, extension is performed with a polymerase that exhibits 5' to 3' exonuclease activity and with any nuclease included in the section entitled, "Nucleases".

Example 4

A target nucleic acid can be detected and/or measured by the following method. A labeled cleavage structure is formed prior to the addition of a FEN nuclease by heating at 95° C. for 5 minutes and then cooling to approximately 50-60° C. (a) a sample containing a target nucleic acid (B in FIG. 4) with (b) an upstream oligonucleotide that specifically hybridizes to the target nucleic acid, (A, in FIG. 4), and (c) a downstream, 5' end labeled oligonucleotide probe having a secondary structure that changes upon binding of the probe to the target nucleic acid and comprising a lac repressor protein tag, wherein the probe specifically hybridizes to a region of the target nucleic acid that is downstream of the hybridizing region of oligonucleotide A. A polymerase that lacks a 5' to 3' exonuclease activity but that possesses a 3' to 5' DNA synthetic activity, such as the enzyme a) Yaq exo-, (prepared by mutagenesis using the Stratagene QuikChange Site-Directed Mutagenesis kit, catalog number #200518, to modify Taq polymerase (Tabor and Richardson, 1985, Proc. Natl. Acad. Sci. USA, 82:1074)), a mutant form of Taq polymerase that lacks 5' to 3' exonuclease activity, b) Pfu, or c) a mutant form of Pfu polymerase that lacks 3' to 5' exonuclease activity (exo-Pfu) is added and incubated under conditions that permit the polymerase to extend oligonucleotide A such that it partially displaces the 5' end of oligonucleotide C (for example 72° C. in 1×Pfu buffer (Stratagene) for 5 minutes to 1 hour. The displaced region of oligonucleotide C forms a 5' flap that is cleaved upon the addition of a FEN nuclease. Alternatively, extension is performed with a polymerase that exhibits 5' to 3' exonuclease activity and with any nuclease included in the section entitled, "Nucleases".

A mutant form of Taq polymerase that lacks a 5' to 3' exonuclease activity but that possesses a 3' to 5' DNA synthetic activity comprises the following mutation: D144S/F667Y Taq wherein D144S eliminates 5' to 3' exonuclease activity and F667Y improves ddNTP incorporation.

Exo- mutants of PolI polymerase can be prepared according to the method of Xu et al., 1997, J. Mol. Biol., 268: 284.

A labeled cleavage structure according to the invention is cleaved with a preparation of PfuFEN-1 (i.e. cloned *Pyrococcus furiosus* FEN-1 that is prepared as described below in Example 9). Cleaving is performed at a cleaving temperature, and the secondary structure of the probe when not bound to the target nucleic acid is stable at or below the cleaving temperature. Cleavage is carried out by adding 2 µl of PfuFEN-1 to a 7 µl reaction mixture containing the following:

| | |
|---|---|
| 3 µl | cleavage structure (10 ng-10 µg) |
| 0.7 µl | 10x FEN nuclease buffer (10X FEN nuclease buffer contains 500 mM Tris-HCl pH 8.0, 100 mM MgCl$_2$) |
| 2.00 µl | PfuFEN-1 enzyme or H$_2$O |
| 1.3 µl | H$_2$O |
| 7.00 µl | total volume |

Samples are incubated for one hour at 50° C. in a Robocyler 96 hot top thermal cycler. Following the addition of 2 µl of Sequencing Stop dye solution (included in the Stratagene Cyclist DNA sequencing kit, catalog #200326), samples are heated at 99° C. for five minutes. Released, labeled, fragments comprising the lac repressor protein are bound via binding of the lac repressor protein to a capture element comprising the double stranded DNA sequence recognized by the lac repressor protein:

```
AATTGTGAGCGGATAACAATT

TTAACACTCGCCTATTGTTAA,
``` on a solid support.

In one embodiment, the labeled fragments are eluted from the capture element by, for example, altering the salt concentration, i.e., decreasing the salt concentration (stringent hybridization conditions typically include salt concentrations of less than about 1M, more usually less than about 500 mM and preferably less than about 200 mM) or by adding an excess of competitor a) lac repressor protein or b) double stranded DNA sequence recognized by the lac repressor protein. Samples containing eluted labeled fragments are analyzed by gel electrophoresis as follows. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80° C.). The gel is exposed overnight to X-ray film to detect the presence of a signal that is indicative of the presence of a target nucleic acid.

Alternatively, extension is performed with a polymerase that exhibits 5' to 3' exonuclease activity and with any nuclease included in the section entitled, "Nucleases".

Example 5

A target nucleic acid can be detected and/or measured by the following method. A labeled cleavage structure is formed prior to the addition of a FEN nuclease by annealing at 95° C. for 5 minutes and then cooling to approximately 50-60° C. (a) a sample containing a target nucleic acid (B in FIG. 4) with (b) an upstream oligonucleotide primer that specifically hybridizes to the target nucleic acid, (A, in FIG. 4), and (c) a downstream, 5' end labeled oligonucleotide probe having a secondary structure that changes upon binding of the probe to the target nucleic acid and comprising a binding moiety (for example ab in FIG. 4, comprising a nucleic acid sequence 5'AGCTACTGATGCAGTCACGT3'), wherein the probe specifically hybridizes to a region of the target nucleic acid that is adjacent to the hybridizing region of oligonucleotide A and further comprises a 5' region that does not hybridize to the target nucleic acid and forms a 5' flap. Annealing is carried out in the presence of 1× Sentinel Molecular beacon core buffer or 10×Pfu buffer.

A labeled cleavage structure according to the invention is cleaved with a preparation of PfuFEN-1 (i.e. cloned *Pyrococcus furiosus* FEN-1 that is prepared as described below in Example 9). Cleaving is performed at a cleaving temperature, and the secondary structure of the probe when not bound to the target nucleic acid is stable at or below the cleaving temperature. Cleavage is carried out by adding 2 µl of PfuFEN-1 to a 7 µl reaction mixture containing the following:

| | |
|---|---|
| 3 µl | cleavage structure (10 ng-10 µg) |
| 0.7 µl | 10x FEN nuclease buffer (10X FEN nuclease buffer contains 500 mM Tris-HCl pH 8.0, 100 mM MgCl$_2$) |
| 2.00 µl | PfuFEN-1 enzyme or H$_2$O |
| 1.3 µl | H$_2$O |
| 7.00 µl | total volume |

Samples are incubated for one hour at 50° C. in a Robocyler 96 hot top thermal cycler. Following the addition of 2 µl of Sequencing Stop dye solution (included in the Stratagene Cyclist DNA sequencing kit, catalog #200326), samples are heated at 99° C. for five minutes. Released, labeled, fragments comprising a binding moiety are bound via binding of the binding moiety to a capture element comprising the sequence, 5'TCGATGACTACGTCAGTGCA3', on a solid support. In one embodiment, the labeled fragments are eluted from the capture element by, for example, decreasing the salt concentration (stringent hybridization conditions typically include salt concentrations of less than about 1M, more usually less than about 500 mM and preferably less than about 200 mM) or by adding an excess of unlabeled, competitor fragment. Samples containing eluted labeled fragments are analyzed by gel electrophoresis as follows. Samples are loaded on an eleven inch long, hand-poured, 20% acrylamide/ bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80° C.). The gel is exposed overnight to X-ray film to detect the presence of a signal that is indicative of the presence of a target nucleic acid.

Alternatively, extension is performed with a polymerase that exhibits 5' to 3' exonuclease activity and with any nuclease included in the section entitled, "Nucleases".

Example 6

A target nucleic acid can be detected and/or measured by the following method. A labeled cleavage structure is formed prior to the addition of a FEN nuclease by annealing at 95° C. for 5 minutes and then cooling to approximately 50-60° C. (a) a sample containing a target nucleic acid (B in FIG. 4) with (b) an upstream oligonucleotide primer that specifically hybridizes to the target nucleic acid, (A, in FIG. 4), and (c) a downstream, 5' end labeled oligonucleotide probe having a secondary structure that changes upon binding of the probe to the target nucleic acid and comprising a lac repressor protein tag, wherein the probe specifically hybridizes to a region of the target nucleic acid that is adjacent to the hybridizing region of oligonucleotide A and further comprises a 5' region that does not hybridize to the target nucleic acid and forms a 5' flap. Annealing is carried out in the presence of 1× Sentinel Molecular beacon core buffer or 10×Pfu buffer.

A labeled cleavage structure according to the invention is cleaved with a preparation of PfuFEN-1 (i.e. cloned *Pyrococcus furiosus* FEN-1 that is prepared as described below in Example 9). Cleaving is performed at a cleaving temperature, and the secondary structure of the probe when not bound to the target nucleic acid is stable at or below the cleaving temperature. Cleavage is carried out by adding 2 μl of PfuFEN-1 to a 7 μl reaction mixture containing the following:

| 3 μl | cleavage structure (10 ng-10 μg) |
| 0.7 μl | 10x FEN nuclease buffer (10X FEN nuclease buffer contains 500 mM Tris-HCl pH 8.0, 100 mM MgCl$_2$) |
| 2.00 μl | PfuFEN-1 enzyme or H$_2$O |
| 1.3 μl | H$_2$O |
| 7.00 μl | total volume |

Samples are incubated for one hour at 50° C. in a Robocyler 96 hot top thermal cycler. Following the addition of 2 μl of Sequencing Stop dye solution (included in the Stratagene Cyclist DNA sequencing kit, catalog #200326), samples are heated at 99° C. for five minutes.

Upon cleavage of the hybridized probe by a nuclease, the lac repressor protein binds specifically to a capture element comprising the double stranded DNA sequence recognized by the lac repressor protein:

```
AATTGTGAGCGGATAACAATT
TTAACACTCGCCTATTGTTAA,
``` on a solid support.

In one embodiment, the labeled fragments are eluted from the capture element as described in Example 4, above. Samples containing eluted labeled fragments are analyzed by gel electrophoresis as follows. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80° C.). The gel is exposed overnight to X-ray film to detect the presence of a signal that is indicative of the presence of a target nucleic acid.

Alternatively, extension is performed with a polymerase that exhibits 5' to 3' exonuclease activity and with any nuclease included in the section entitled, "Nucleases".

Example 7

A target nucleic acid can be detected and/or measured by the following method. A labeled cleavage structure is formed prior to the addition of a FEN nuclease by annealing at 95° C. for 5 minutes and then cooling to approximately 50-60° C. (a) a sample containing a target nucleic acid (B in FIG. 4) with (b) a downstream, 5' end labeled oligonucleotide probe having a secondary structure that changes upon binding of the probe to the target nucleic acid and a binding moiety (for example ab in FIG. 4, comprising a nucleic acid sequence, i.e., 5'AGC-TACTGATGCAGTCACGT3'), wherein the probe specifically hybridizes to a region of the target nucleic acid and comprises a 5' region that does not hybridize to the target nucleic acid and forms a 5' flap. Annealing is carried out in the presence of 1× Sentinel Molecular beacon core buffer or 10×Pfu buffer.

A labeled cleavage structure according to the invention is cleaved with a nuclease that is capable of cleaving this cleavage structure (e.g., Taq polymerase). Cleaving is performed at a cleaving temperature, and the secondary structure of the probe when not bound to the target nucleic acid is stable at or below the cleaving temperature. Cleavage is carried out by adding 2 μl of a nuclease to a 7 μl reaction mixture containing the following:

| 3 μl | cleavage structure (10 ng-10 μg) |
| 0.7 μl | 10x nuclease buffer (500 mM Tris-HCl pH 8.0, 100 mM MgCl$_2$) |
| 2.00 μl | nuclease or H$_2$O |
| 1.3 μl | H$_2$O |
| 7.00 μl | total volume |

Samples are incubated for one hour at 50° C. in a Robocyler 96 hot top thermal cycler. Following the addition of 2 μl of Sequencing Stop dye solution (included in the Stratagene Cyclist DNA sequencing kit, catalog #200326), samples are heated at 99° C. for five minutes. Released, labeled, fragments comprising a binding moiety are bound via binding of the binding moiety to a capture element comprising a nucleic acid sequence, i.e., 5'TCGATGACTACGTCAGTGCA3', on a solid support. In one embodiment, the labeled fragments are eluted from the capture element by, for example, decreasing the salt concentration (stringent hybridization conditions typically include salt concentrations of less than about 1M, more usually less than about 500 mM and preferably less than about 200 mM) or by adding an excess of unlabeled, competitor fragment. Samples containing eluted labeled fragments are analyzed by gel electrophoresis as follows. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80° C.). The gel is exposed overnight to X-ray film to detect the presence of a signal that is indicative of the presence of a target nucleic acid.

Alternatively, extension is performed with a polymerase that exhibits 5' to 3' exonuclease activity and with any nuclease included in the section entitled, "Nucleases".

Example 8

A target nucleic acid can be detected and/or measured by the following method.

A labeled cleavage structure is formed prior to the addition of a FEN nuclease by annealing at 95° C. for 5 minutes and then cooling to approximately 50-60° C. (a) a sample containing a target nucleic acid (B in FIG. 4) with (b) a downstream, 5' end labeled oligonucleotide probe having a secondary structure that changes upon binding of the probe to the target nucleic acid and a tag comprising the lac repressor protein, wherein the probe specifically hybridizes to a region of the target nucleic acid and comprises a 5' region that does not hybridize to the target nucleic acid and forms a 5' flap. Annealing is carried out in the presence of 1× Sentinel Molecular beacon core buffer or 10×Pfu buffer.

A labeled cleavage structure according to the invention is cleaved with a nuclease that is capable of cleaving this cleavage structure (e.g., Taq polymerase). Cleaving is performed at a cleaving temperature, and the secondary structure of the probe when not bound to the target nucleic acid is stable at or below the cleaving temperature. Cleavage is carried out by adding 2 µl of a nuclease to a 7 µl reaction mixture containing the following:

| | |
|---|---|
| 3 µl | cleavage structure (10 ng-10 µg) |
| 0.7 µl | 10x nuclease buffer (500 mM Tris-HCl pH 8.0, 100 mM MgCl₂) |
| 2.00 µl | nuclease or H₂O |
| 1.3 µl | H₂O |
| 7.00 µl | total volume |

Samples are incubated for one hour at 50° C. in a Robocyler 96 hot top thermal cycler. Following the addition of 2 µl of Sequencing Stop dye solution (included in the Stratagene Cyclist DNA sequencing kit, catalog #200326), samples are heated at 99° C. for five minutes. Upon cleavage of the hybridized probe by a nuclease, the lac repressor protein binds specifically to a capture element comprising the double stranded DNA sequence recognized by the lac repressor protein:

AATTGTGAGCGGATAACAATT

TTAACACTCGCCTATTGTTAA, on a solid support.

In one embodiment, the labeled fragments are eluted from the capture element as described in Example 4, above. Samples containing eluted labeled fragments are analyzed by gel electrophoresis as follows. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80° C.). The gel is exposed overnight to X-ray film to detect the presence of a signal that is indicative of the presence of a target nucleic acid.

Alternatively, extension is performed with a polymerase that exhibits 5' to 3' exonuclease activity and with any nuclease included in the section entitled, "Nucleases".

Example 9

Cloning Pfu FEN-1

A thermostable FEN nuclease enzyme useful according to the invention can be prepared according to the following method.

The thermostable FEN nuclease gene can be isolated from genomic DNA derived from *P. furiosus* (ATCC #43587) according to methods of PCR cloning well known in the art. The cloned PfuFEN-1 can be overexpressed in bacterial cells according to methods well known in the art and described below.

The following pCAL-n-EK cloning oligonucleotides were synthesized and purified:

a. 5'GACGACGACAAGATGGGTGTCCCAATTGGTGAGATTATACCAAGA AAAG 3'
and b. 5'GGAACAAGACCCGTTTATCTCTTGAACCAACTTTCAAGGGTTGAT TGTTTCCACT 3'.

The Affinity® Protein Expression and Purification System was obtained from Stratagene and used according to the manufacturer's protocols.

Amplification

The insert DNA was prepared by PCR amplification with gene-specific primers (oligonucleotides a and b, described above) that include 12 and 13-nucleotide sequences at the 5' ends that are complementary to the pCAL-n-EK vector single-stranded tails, thus allowing for directional cloning. The FEN-1 sequence was amplified from genomic DNA derived from *P. furiosus* by preparing amplification reactions (five independent 100 µl reactions) containing:

| | |
|---|---|
| 50 µl | 10 × cPfu Buffer (Stratagene) |
| 7.5 µl | Pfu Genomic DNA (approx. 100 ng/µl) |
| 7.5 µl | PfuTurbo(2.5 u/µl), (Stratagene, Catalog # 600250) |

-continued

| | | |
|---|---|---|
| 15 µl | mixed primer pair (100 ng/µl each) (oligonucleotides a and b, described above) | |
| 4 µl | 100 mM dNTP | |
| 416 µl | H₂O | |
| 500 µl | total | | and carrying out the amplification under the following conditions using a Stratagene Robocycler 96 hot top thermal cycler:

| | | | |
|---|---|---|---|
| Window 1 | 95° C. | 1 minute | 1 cycle |
| Window 2 | 95° C. | 1 minute | |
| | 50° C. | 1 minute | 30 cycles |
| | 72° C. | 3 minutes | |

The PCR products from each of the five reactions were combined into one tube, purified using StrataPrep PCR and eluted in 50 µl 1 mM Tris-HCl pH 8.6. The FEN-1 PCR product was analyzed on a gel and was determined to be approximately 1000 bp.

The PCR product comprising the fen-1 gene was cloned into the pCALnEK LIC vector (Stratagene) by creating ligation independent cloning termini (LIC), annealing the PCR product comprising the fen-1 gene to the pCALnEK LIC vector (Stratagene), and transforming cells with the annealing mixture according to the following method. Briefly, following PCR amplification, the PCR product is purified and treated with Pfu DNA polymerase in the presence of dATP (according to the manual included with the Affinity® Protein Expression and Purification System, Stratagene, catalog #200326). In the absence of dTTP, dGTP and dCTP, the 3' to 5'-exonuclease activity of Pfu DNA polymerase removes at least 12 and 13 nucleotides at the respective 3' ends of the PCR product. This activity continues until the first adenine is encountered, producing a DNA fragment with 5'-extended single-stranded tails that are complementary to the single-stranded tails of the pCAL-n-EK vector.

Creating LIC Termini

LIC termini were created by preparing the following mixture:
45 µl purified PCR product (~0.5 µg/µl)
2.5 µl 10 mM dATP
5 µl 10×cPfu buffer
1 µl cPfu (2.5 u/µl)
0.5 µl H₂O cPfu and cPfu buffer can be obtained from Stratagene (cPfu, Stratagene Catalog #600153 and cPfu buffer, Stratagene Catalog #200532).

Samples were incubated at 72° C. for 20 minutes and products were cooled to room temperature. To each sample was added 40 ng prepared pCALnEK LIC vector (the prepared vector is available commercially from Stratagene in the Affinity LIC Cloning and Protein Purification Kit (214405)). The vector and insert DNA are combined, allowed to anneal at room temperature and transformed into highly competent bacterial host cells (Wyborski et al., 1997, *Strategies*, 10:1).

Preparing Cells for Production of FEN

Two liters of LB-AMP was inoculated with 20 ml of an overnight culture of a FEN-1 clone (clone 3). Growth was allowed to proceed for approximately 11 hours at which point cells had reached an OD$_{600}$=0.974. Cells were induced overnight (about 12 hours) with 1 mM IPTG. Cells were collected by centrifugation and the resulting cell paste was stored at −20° C.

Purification of Tagged FEN-1

Cells were resuspended in 20 ml of Calcium binding buffer

CaCl₂ Binding Buffer
50 mM Tris-HCl (pH 8.0)
150 mM NaCl
1.0 mM MgOAc
2 mM CaCl₂

The samples were sonicated with a Branson Sonicator using a microtip. The output setting was 5 and the duty cycle was 90%. Samples were sonicated three times and allowed to rest on ice during the intervals. The sonicate was centrifuged at 26,890×g. Cleared supernatants were mixed with 1 ml of washed (in CaCl₂ binding buffer) calmodulin agarose (CAM agarose) in a 50 ml conical tube and incubated on a slowly rotating wheel in a cold room (4° C.) for 5 hours. The CAM agarose was collected by light centrifugation (5000 rpm in a table top centrifuge).

Following removal of the supernatant, the CAM agarose was washed with 50 ml CaCl₂ binding buffer and transferred to a disposable drip column. The original container and pipet were rinsed thoroughly to remove residual agarose. The column was rinsed with approximately 200 ml of CaCl₂ binding buffer.

Elution was carried out with 10 ml of 50 mM NaCl elution buffer (50 mM NaCl, 50 mM Tris-HCl pH 8.0, 2 mM EGTA). 0.5 ml fractions were collected. A second elution step was carried out with 1M NaCl elution buffer wherein 0.5 ml fractions were collected.

Evaluation of Purified Tagged FEN-1

Figure 5:
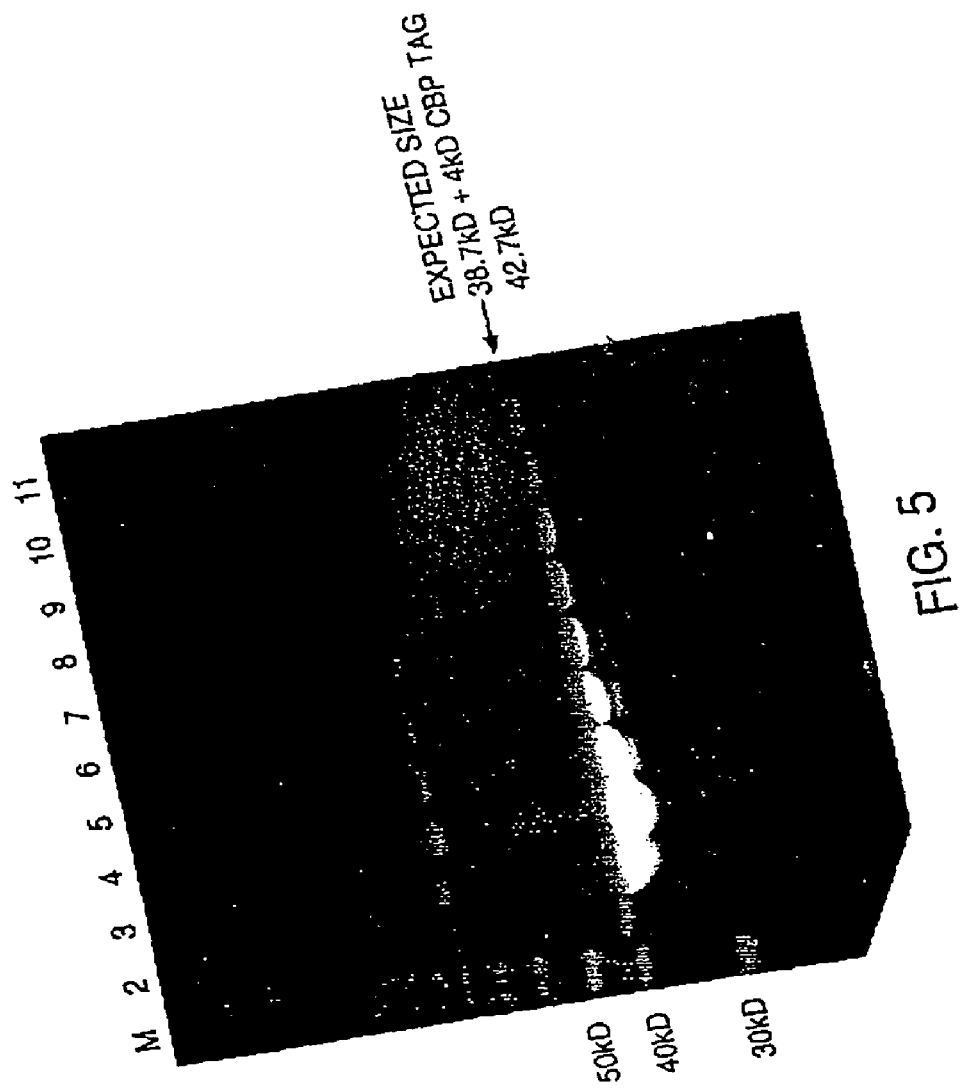
FIG. 5 is a Sypro Orange stained polyacrylamide gel demonstrating CBP-tagged PFU FEN-1 protein.

Fractions containing CBP-tagged Pfu FEN-1 eluted in 1M NaCl were boiled in SDS and analyzed by SDS-PAGE on a 4-20% gel stained with Sypro Orange (FIG. 5).

The protein concentration of uncleaved FEN-1 was determined to be approximately 150 ng/microliter (below).

Enterokinase Protease (EK) Cleavage of the Purified FEN-1

Fractions 3-9 were dialyzed in 50 mM NaCl, 50 mM Tris-HCl pH 8.0 and 2 mM CaCl₂ overnight at 4° C.

An opaque, very fine precipitate appeared in the dialyzed FEN-1. When the sample was diluted 1/20 the precipitate was removed. When the sample was diluted 1/3 insoluble material was still detectable. The 1/3 diluted material was heated at 37° C. for 2 minutes and mixed with Tween 20 to a final concentration of 0.1%. Upon the addition of the Tween 20, there was an almost immediate formation of "strings" and much coarser solids in the solution which could not be reversed even after the solution was adjusted to 1M NaCl.

EK cleavage was carried out using as a substrate the sample that was diluted 1/20 as well as with a dilute sample prepared by rinsing the dialysis bag with 1×EK buffer.

EK cleavage was carried out by the addition of 1 µl EK (1 u/µl) overnight at room temperature (about 16 hours).

100 µl of STI agarose combined with 100 µl of CAM agarose were rinsed twice with 10 ml of 1×STI buffer (50 mM Tris-HCl pH 8.0, 200 mM NaCl, 2 mM CaCl₂, 0.1% Tween 20). NaCl was added to the two EK samples to bring the final concentration to 200 mM NaCl. The two samples were combined and added to the rinsed agarose. The samples were rotated slowly on a wheel at 4° C. for three hours and separated by light centrifugation in a table top centrifuge (as described). The supernatant was removed and the resin was rinsed twice with 500 µl 1×STI. The two rinses were combined and saved separately from the original supernatant. Samples were analyzed by SDS-PAGE on a 4-20% gel.

The concentration of digested product was approximately 23 ng/µl as determined by comparison to a Pfu standard at a concentration of approximately 50 ng/ml.

Example 10

FEN Nuclease Activity

The endonuclease activity of a FEN nuclease and the cleavage structure requirements of a FEN nuclease prepared as described in Example 2 can be determined according to the methods described either in the section entitled "FEN nucleases" or below.

Briefly, three templates (FIG. 2) are used to evaluate the activity of a FEN nuclease according to the invention. Template 1 is a 5' $^{33}$P labeled oligonucleotide (Heltest4) with the following sequence:

5'AAAATAAATAAAAAAAATACTGTTGGGAAGGGCGATCGGTGCG3'.

The underlined section of Heltest4 represents the region complementary to M13mp18+. The cleavage product is an 18 nucleotide fragment with the sequence AAAATAAA-TAAAAAAAAT. Heltest4 binds to M13 to produce a complementary double stranded domain as well as a non-complementary 5' overhang. This duplex forms template 2 (FIG. 2). Template 3 (FIG. 2) has an additional primer (FENAS) bound to M13 which is directly adjacent to Heltest 4. The sequence of FENAS is: 5'CCATTCGCCATTCAGGCTGCGCA 3'. In the presence of template 3, a FEN nuclease binds the free 5' terminus of Heltest4, migrates to the junction and cleaves Heltest4 to produce an 18 nucleotide fragment. The resulting cleavage products are separated on a 6% acrylamide, 7M urea sequencing gel.

Templates are prepared as described below:

|  | Template 1 | Template 2 | Template 3 |
|---|---|---|---|
| Heltest4 | 14 µl | 14 µl | 14 µl |
| M13 | ** | 14 µl | 14 µl |
| FENAS | ** | ** | 14 µl |
| H$_2$O | 28 µl | 14 µl | ** |
| 10 × Pfu Buff. | 4.6 µl | 4.6 µl | 4.6 µl |

Pfu buffer can be obtained from Stratagene (Catalog #200536).

The template mixture is heated at 95° C. for five minutes, cooled to room temperature for 45 minutes and stored at 4° C. overnight. The enzyme samples are as follows:

A. H$_2$O (control)
B. 2 µl undiluted uncleaved FEN-1 (~445 ng/µl)
C. 2 µl 1/10 dilution of uncleaved FEN-1 (~44.5 ng/µl)
D. 2 µl enterokinase protease (EK) cleaved FEN-1 (~23 ng/µl)

The four reaction mixtures are mixed with the three templates as follows:

| 3 µl | template 1, template 2 or template 3 |
| 0.7 µl | 10 × cloned Pfu buffer |
| 0.6 µl | 100 mM MgCl$_2$ |
| 2.00 µl | FEN-1 or H$_2$O |
| 0.7 µl | H$_2$O |
| 7.00 µl | total volume |

The reactions are allowed to proceed for 30 minutes at 50° C. and stopped by the addition of 2 µl formamide "Sequencing Stop" solution to each sample. Samples are heated at 95° C. for five minutes and loaded on a 6% acrylamide 7M urea CastAway gel (Stratagene).

Alternatively, FEN nuclease activity can be analyzed in the following buffer wherein a one hour incubation time is utilized.

10 × FEN Nuclease Buffer 500 mM Tris – HCl pH 8.0

100 mM MgCl$_2$

The reaction mixture is as follows:

| 3 µl | template 1, template 2 or template 3 |
| 0.7 µl | 10 × FEN nuclease buffer |
| 2.00 µl | FEN-1 or H$_2$O (A-D, above) |
| 1.3 µl | H$_2$O |
| 7.00 µl | total volume |

Samples are incubated for one hour at 50° C. in the Robocyler 96 hot top thermal cycler. Following the addition of 2 µl of Sequencing Stop (95% formamide, 20 mM EDTA, 0.05% bromophenol blue, 0.05% xylene cyanol, available from Stratagene) dye solution, samples are heated at 99° C. for five minutes. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80° C.). The gel is exposed overnight to X-ray film.

An autoradiograph of a FEN-1 nuclease assay wherein templates 1, 2 and 3 (prepared as described above) are cleaved by the addition of:

A. H$_2$O
B. 2 µl of CBP-tagged Pfu FEN-1
C. 2 µl of CBP-tagged Pfu FEN-1 diluted (1:10)
D. 2 µl of EK cleaved Pfu FEN-1 is presented in FIG. 6.

The lanes are as follows. Lanes 1A, 1B, 1C and 1D represent template 1 cleaved with H$_2$O, undiluted CBP-tagged Pfu FEN-1, a 1:10 dilution of CBP-tagged Pfu FEN-1 and EK cleaved Pfu FEN-1, respectively. Lanes 2A, 2B, 2C and 2D represent template 2 cleaved with H$_2$O, undiluted CBP-tagged Pfu FEN-1, a 1:10 dilution of CBP-tagged Pfu FEN-1 and EK cleaved Pfu FEN-1, respectively. Lanes 3A, 3B, 3C and 3D represent template 3 cleaved with H$_2$O, undiluted CBP-tagged Pfu FEN-1, a 1:10 dilution of CBP-tagged Pfu FEN-1 and EK cleaved Pfu FEN-1, respectively.

Tagged Pfu FEN-1 contains the N-terminal CBP affinity purification tag. Any differences in activity between tagged and untagged versions of FEN-1 are due to differences in protein concentration (concentrations of enzyme samples are provided above) since the amounts of tagged versus untagged FEN-1 are not equivalent. Both tagged and untagged Pfu FEN-1 demonstrate cleavage activity.

Figure 6:
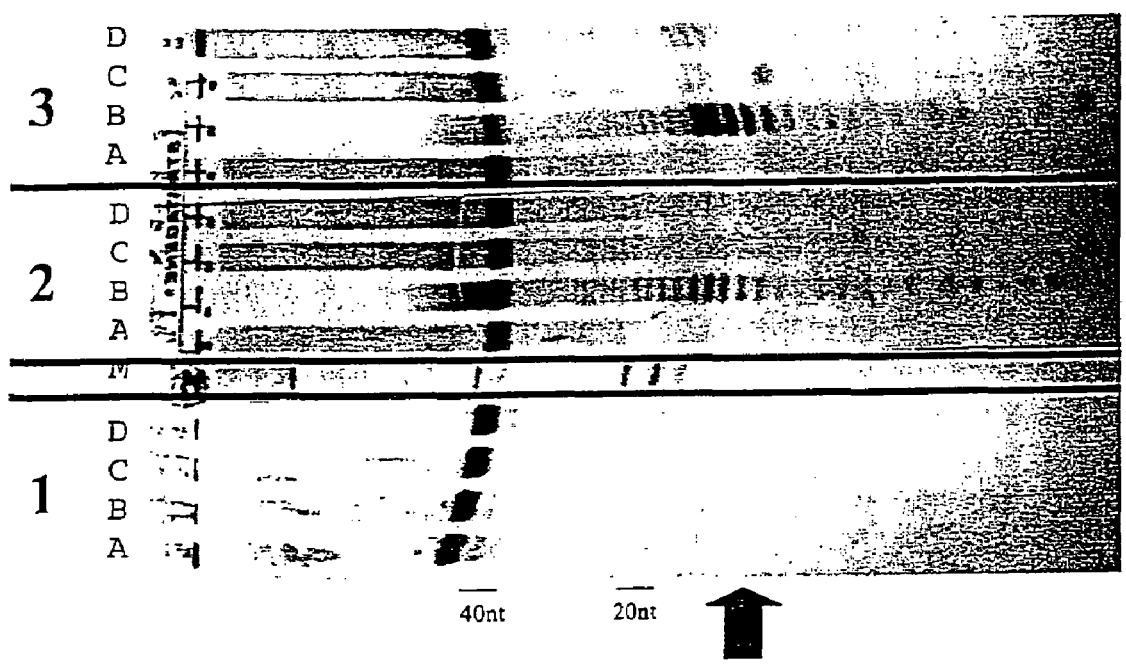
FIG. 6 is an autoradiograph of a FEN-1 nuclease assay.

FIG. 6 demonstrates the background level of cleavage in the absence of FEN-1 (lanes 1A, 2A and 3A). Further, this figure demonstrates that tagged Pfu FEN-1 cleaves more of template 2 as compared to template 1. In particular, the greatest amount of template 2 is cleaved in the presence of undiluted, tagged Pfu FEN-1 (lane 2B). Analysis of template 3 demonstrates that the greatest amount of template 3 is cleaved by undiluted, tagged Pfu FEN-1 and the least amount of template 3 is cleaved by diluted tagged FEN-1. Labeled probe migrates as a 40-43 nucleotide band. FEN-1 preferentially cleaves template 3 (which comprises an upstream primer) as compared to template 2. The cleavage product bands are the major bands migrating at 16-20 nucleotides. Heterogeneity in the labeled cleavage products is the result of heterogeneity in the labeled substrate, which was not gel-purified prior to use.

Example 11

PCR Amplification and Detection of β-Actin in the Presence of a FEN-1 Nuclease and a Tag Polymerase Deficient in 5' to 3' Exonuclease Activity A PCR assay is used to detect a target nucleic acid. According to the method of this assay, a PCR reaction is carried out in the presence of a probe having a secondary structure that changes upon binding to a target nucleic acid and comprising a binding moiety or a tag, Taq polymerase deficient in 5' to 3' exonuclease activity (for example Yaq exo-), and a thermostable FEN-1 nuclease (e.g. Pfu FEN-1, prepared as described in Example 2). Detection of the release of fluorescently labeled fragments that bind, via binding of the binding moiety or tag, to a capture element on a solid support indicates the presence of the target nucleic acid.

Duplicate PCR reactions containing 1× Sentinel Molecular beacon core buffer, 3.5 mM $MgCl_2$, 200 µM of each dNTP, a Taq polymerase deficient in 5' to 3' exonuclease activity (~1.45 U), Pfu FEN-1 (~23 ng), β-Actin primers (300 nM each) and a β-actin specific fluorogenic probe having a secondary structure that changes upon binding of the probe to the β-Actin target sequence and comprising a binding moiety or tag. 10 ng of human genomic DNA (Promega) is used as the target nucleic acid in each reaction. This reaction is performed in a 50 µl volume. Negative control reactions containing either Pfu FEN-1 alone, a Taq polymerase deficient in 5' to 3' exonuclease activity alone or reaction mixtures containing all components except a human genomic DNA template are prepared. Positive control reactions comprising 2.5 Units of Taq 2000 are also prepared. During the PCR reaction, there is simultaneous formation of a cleavage structure, amplification of the β-actin target sequence and cleavage of the cleavage structure. Thermocycling parameters are selected such that cleavage of the cleavage structure is performed at a cleaving temperature, and the secondary structure of the probe, when not bound to the target nucleic acid is stable at or below the cleaving temperature. Reactions are assayed in a spectrofluorometric thermocycler (ABI 7700). Thermocycling parameters are 95°C for 2 min and 40 cycles of 95°C for 15 sec, 60°C for 60 sec and 72°C for 15 sec. Samples are interrogated during the annealing step.

Released, fluorescently labeled fragments are bound, via the binding moiety or tag present on the probe, to a capture element bound to a solid support.

Example 12

PCR Amplification and Detection of β-Actin in the Presence of a FEN-1 Nuclease and a Pfu Polymerase Deficient in 5' to 3' Exonuclease Activity A PCR assay is used to detect a target nucleic acid. According to the method of this assay, a PCR reaction is carried out in the presence of a probe having a secondary structure that changes upon binding of the probe to the β-actin target nucleic acid and comprising a binding moiety or tag, Pfu polymerase (naturally lacking 5' to 3' exonuclease activity) or, in addition, Pfu polymerase deficient in 3' to 5' exonuclease activity as well (for example exo-Pfu), and a thermostable FEN-1 nuclease (Pfu FEN-1). Detection of the release of fluorescently labeled fragments that bind, via binding of the binding moiety or tag, to a capture element on a solid support indicates the presence of the target nucleic acid.

Duplicate PCR reactions containing 1× Cloned Pfu buffer (available from Stratagene, Catalog #200532), 3.0 mM $MgCl_2$, 200 µM of each dNTP, 5 units of a Pfu polymerase deficient in 3' to 5' exonuclease activity, tagged or untagged Pfu FEN-1 (~23 ng), PEF (1 ng) (described in WO 98/42860), β-Actin primers (300 nM each), and fluorogenic probe having a secondary structure that changes upon binding of the probe to the target β-actin nucleic acid sequence are prepared. 10 ng of human genomic DNA (Promega) is used as the target nucleic acid in each reaction. Reactions are performed in a 50 µl volume. Negative control reactions comprising a Pfu polymerase deficient in both 5' to 3' and 3' to 5' exonuclease activities alone or containing all of the components except the human genomic DNA template are also prepared. A reaction mixture containing 2.5 Units of Taq 2000 is prepared and used as a positive control. During the PCR reaction, there is simultaneous formation of a cleavage structure, amplification of the β-actin target sequence and cleavage of the cleavage structure. Thermocycling parameters are selected such that cleavage of the cleavage structure is performed at a cleaving temperature, and the secondary structure of the probe, when not bound to the target nucleic acid is stable at or below the cleaving temperature. Reactions are analyzed in a spectrofluorometric thermocycler (ABI 7700). Thermocycling parameters are 95°C for 2 min and 40 cycles of 95°C for 15 sec, 60°C for 60 sec and 72°C for 15 sec.

Released, fluorescently labeled fragments are bound via the binding moiety or tag present on the probe, to a capture element bound to a solid support.

Example 13

Figure 7A:
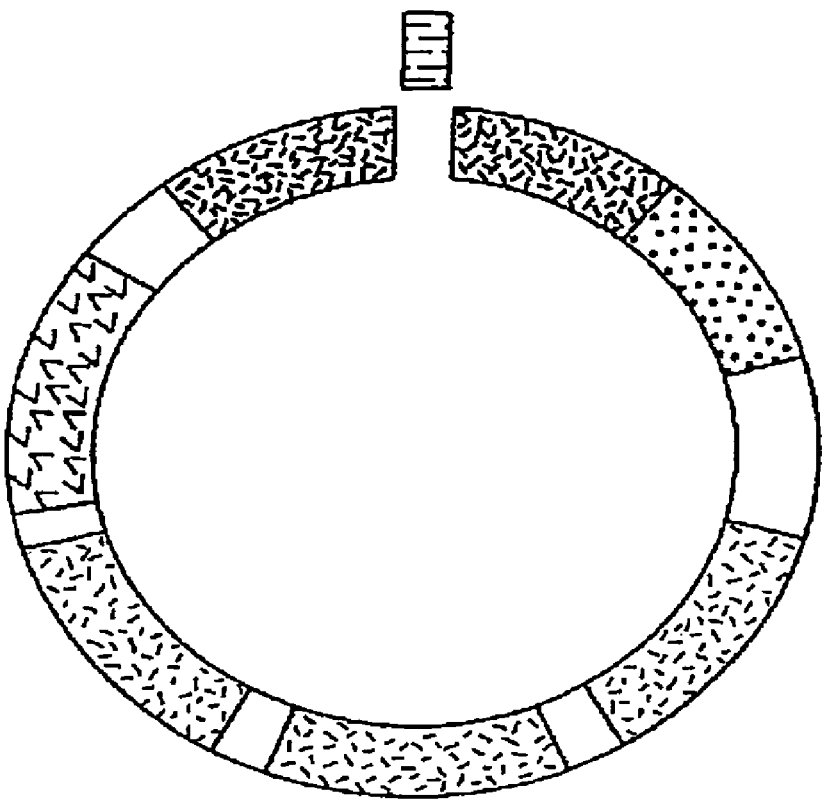
FIG. 7 is a representation of an open circle probe for rolling circle amplification.
Figure 7B:
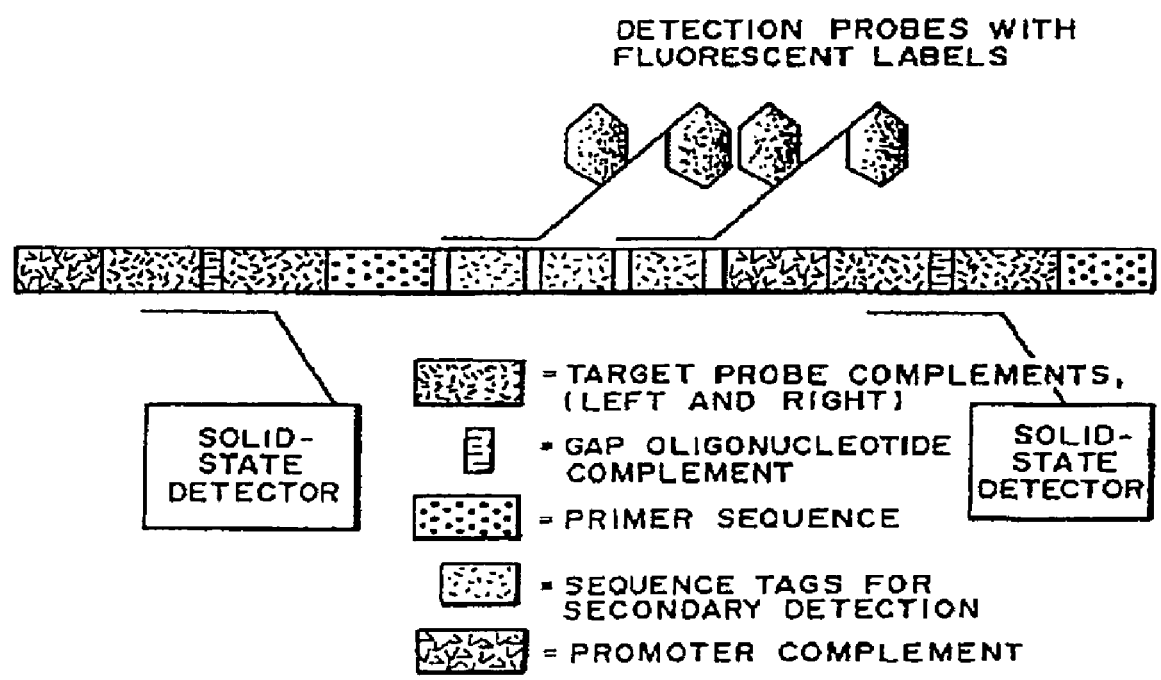
Figure 8B:
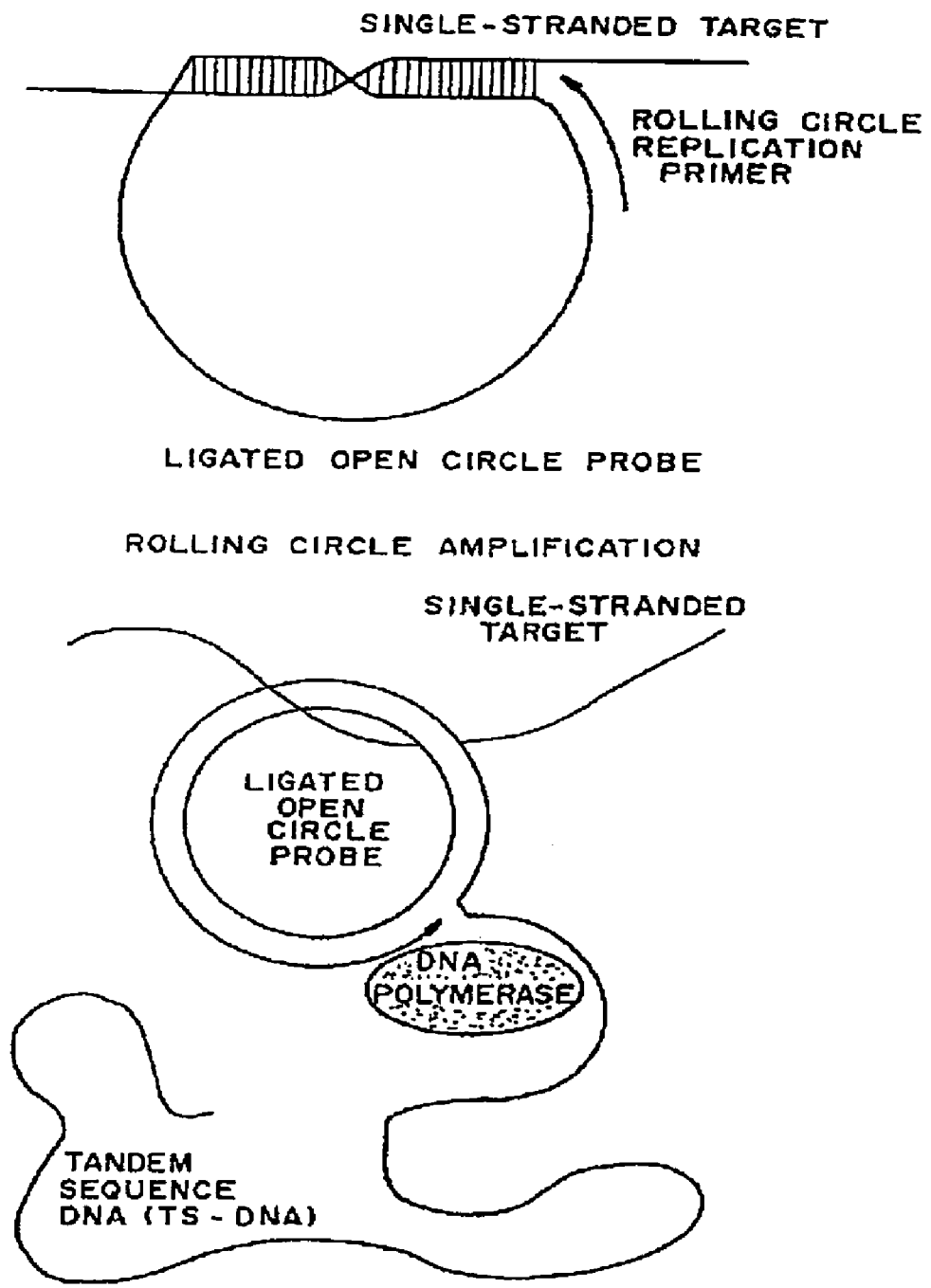
FIG. 8 is a representation of rolling circle amplification.

An assay according to the invention involving rolling circle amplification is performed using the human ornithine transcarbamylase gene as a target, which is detected in human DNA extracted from buffy coat by standard procedures. Target (400 ng) is heat-denatured for 4 minutes at 97° C., and incubated under ligation conditions in the presence of two 5'-phosphorylated oligonucleotides, an open circle probe and one gap oligonucleotide. The open circle probe has the sequence: gaggagaataaaagtttctca taagactcgtcatgtctcagcagct-tctaacggtcactaatacgactcactataggttctgcctctgggaacac, the gap nucleotide for the wild-type sequence is: tagtgatc. FIGS. 7 and 8 depict rolling circle probes and rolling circle amplification. The reaction buffer (40 ul) contains 5 units/µl of T4 DNA ligase (New England Biolabs), 10 mM Tris-HCl, pH 7.5, 0.2 M NaCl, 10 mM $MgCl_2$, 4 mM ATP, 80 nM open circle probe and 100 nM gap oligonucleotide. After incubation for 25 minutes at 37° C., 25 ul are removed and added to 25 ul of a solution containing 50 mM Tris-HCl, pH 7.5, 10 mM $MgCl_2$, 1 mM DTT, 400 µM each of dTTP, dATP, dGTP, dCTP, 0.2 µM rolling circle replication primer: gctgagacat-gacgagtc, phi29 DNA polymerase (160 ng/50 ul). The sample is incubated for 30 minutes at 30° C.

RNA is produced from a T7 promoter present in the open circle probe, by the addition of a compensating buffer (a stock solution or concentrate) that is diluted to achieve the following concentration of reagents: 35 mM Tris-HCl, pH 8.2, 2 mM spermidine, 18 mm $MgCl_2$, 5 mM GMP, 1 mM of ATP, CTP, GTP, 333 uM UTP, 667 uM Biotin-16-UTP, 0.03% Tween 20, 2 units per ul of T7 RNA polymerase. RNA production is performed as described in U.S. Pat. No. 5,858,033. The incubation is allowed to proceed for 90 minutes at 37° C.

Five μl of each sample (the actual test sample, a (−) ligase control sample, a (−) phi29 DNA polymerase control and a (−) T7 RNA polymerase control) in duplicate are removed for detection. The reverse transcription process includes the steps of A) ligating the open circle, B) synthesizing rolling circle single stranded DNA, C) making RNA (from a T7 promoter present in the open circle probe), D) reverse transcribing the RNA to make cDNA, and E) performing PCR amplification of the cDNA using primers and probes for generation of an detection of FEN cleavage structures, according to the invention. For reverse transcription, the reagents and protocols supplied with the Stratagene Sentinel Single-Tube RT-PCR Core Reagent Kit (Cat#600505) are used, except for the substitution of equal amounts of Yaq DNA polymerase for the Taq 2000 DNA polymerase which is recommended by the manufacturer. Each reaction contains 1×Sentinel molecular beacon RT-PCR core buffer, 3.5 mM $MgCl_2$, 200 μM of each dNTP, 5 units exo-Pfu, 23 ng Pfu FEN-1, 1 ng PEF, 500 nM each of the upstream primer: aagtttctcataagactcgtcat, the reverse primer: aggcagaacctatagtgagtcgt, and the fluorogenic probe (for example labeled with FAM-DABCYL) having a secondary structure, as defined herein, that changes upon binding to the target nucleic acid and further comprising a binding moiety. The reactions are subjected to incubation for 30 minutes at 45° C., 3 minutes at 95° C., followed by one cycle in a thermal cycler: 2 minutes at 95° C., 1 minute at 50° C., 1 minute at 72° C. The fluorescence in then determined in a fluorescence plate reader, such as Stratagene's FluorTracker or PE Biosystems' 7700 Sequence Detection System in Plate-Read Mode.

A crosscheck for the efficiency of detection is possible because of the incorporation of Biotin-16-UTP in the rolling circle amplification RNA product. An aliquot of the reactions is captured on glass slides (or alternatively in microwell plates) using an immobilized capture probe. Detection of the captured RNA amplicon is described in detail in U.S. Pat. No. 5,854,033, hereby incorporated by reference.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

I claim:

1. A composition for generating a signal indicative of the presence of a target nucleic acid sequence in a sample, said composition comprising a probe having a 5' region and a 3' flap and a *P. furiosus* polymerase having 3' exonuclease activity, wherein said probe comprises at least one labeled moiety capable of providing a signal and a secondary structure that changes upon binding of said probe to said target nucleic acid sequence, wherein said probe and said target nucleic acid sequence together form a cleavage structure and wherein said cleavage structure generates a signal when cleaved by a nuclease.

2. The composition of claim 1, further comprising a target nucleic acid.

3. The composition of claim 2, wherein the 5' region of the probe is complementary to the target nucleic acid.

4. The composition of claim 1, wherein the at least one labeled moiety is operatively coupled to the 3' flap of the probe.

5. The composition of claim 1, further comprising an upstream oligonucleotide primer, wherein said upstream oligonucleotide primer hybridizes upstream of the probe.

6. A kit for generating a signal indicative of the presence of a target nucleic acid sequence in a sample, comprising a probe having a 5' region and a 3' flap, a *P. furiosus* polymerase having 3' exonuclease activity and a suitable buffer, wherein the probe comprises at least one labeled moiety capable of providing a signal and a secondary structure that changes upon binding of said probe to said target nucleic acid sequence, wherein said probe and said target nucleic acid sequence together form a cleavage structure and wherein said cleavage structure generates a signal when cleaved by a nuclease.

7. The kit of claim 6, wherein the 5' region of the probe is complementary to the target.

8. The kit of claim 6, wherein the at least one labeled moiety is operatively coupled to the 3' flap of the probe.

9. The kit of claim 6, further comprising an upstream oligonucleotide primer, wherein said upstream oligonucleotide primer hybridizes upstream of the probe.

* * * * *

SEQUENCE LISTING

```
<160> NUMBER OF SEQ ID NOS: 49

<210> SEQ ID NO 1
<211> LENGTH: 43
<212> TYPE: DNA
<213> ORGANISM: Artificial Sequence
<220> FEATURE:
<222> LOCATION: (1)..(43)
<223> OTHER INFORMATION: Heltest 4 oligonucleotide for FEN endonuclease
      activity assay

<400> SEQUENCE: 1
aaaataaata aaaaaatac tgttgggaag ggcgatcggt gcg                    43

<210> SEQ ID NO 2
<211> LENGTH: 18
<212> TYPE: DNA
<213> ORGANISM: Artificial Sequence
<220> FEATURE:
<222> LOCATION: (1)..(18)
<223> OTHER INFORMATION: cleavage product of oligonucleotide Heltest4

<400> SEQUENCE: 2
aaaataaata aaaaaat                                                18

<210> SEQ ID NO 3
<211> LENGTH: 23
<212> TYPE: DNA
<213> ORGANISM: Artificial Sequence
<220> FEATURE:
<222> LOCATION: (1)..(23)
<223> OTHER INFORMATION: FENAS primer

<400> SEQUENCE: 3
ccattcgcca ttcaggctgc gca                                         23
```

```
<210> SEQ ID NO 4
<211> LENGTH: 21
<212> TYPE: DNA
<213> ORGANISM: Escherichia coli
<220> FEATURE:
<222> LOCATION: (1)..(21)
<223> OTHER INFORMATION: Lac repressor binding site

<400> SEQUENCE: 4
aattgtgagc ggataacaat t                                          21

<210> SEQ ID NO 5
<211> LENGTH: 21
<212> TYPE: DNA
<213> ORGANISM: Escherichia coli
<220> FEATURE:
<222> LOCATION: (1)..(21)
<223> OTHER INFORMATION: Lac repressor binding site

<400> SEQUENCE: 5
ttaacactcg cctattgtta a                                          21

<210> SEQ ID NO 6
<211> LENGTH: 16
<212> TYPE: DNA
<213> ORGANISM: Escherichia coli
<220> FEATURE:
<222> LOCATION: (1)..(16)
<223> OTHER INFORMATION: CAP DNA binding site

<400> SEQUENCE: 6
tgtgagttag ctcact                                                16

<210> SEQ ID NO 7
<211> LENGTH: 16
<212> TYPE: DNA
<213> ORGANISM: Escherichia coli
<220> FEATURE:
<222> LOCATION: (1)..(16)
<223> OTHER INFORMATION: CAP DNA binding site

<400> SEQUENCE: 7
acactcaatc gagtga                                                16

<210> SEQ ID NO 8
<211> LENGTH: 17
<212> TYPE: DNA
<213> ORGANISM: Bacteriophage lambda
<220> FEATURE:
<222> LOCATION: (1)..(17)
<223> OTHER INFORMATION: lambda repressor DNA binding site

<400> SEQUENCE: 8
tatcaccgcc agaggta                                               17

<210> SEQ ID NO 9
<211> LENGTH: 17
<212> TYPE: DNA
<213> ORGANISM: Bacteriophage lambda
<220> FEATURE:
<222> LOCATION: (1)..(17)
<223> OTHER INFORMATION: lambda repressor DNA binding site

<400> SEQUENCE: 9
atagtggcgg tctccat                                               17
```

```
<210> SEQ ID NO 10
<211> LENGTH: 17
<212> TYPE: DNA
<213> ORGANISM: Saccharomyces sp.
<220> FEATURE:
<222> LOCATION: (1)..(17)
<223> OTHER INFORMATION: GAL4 DNA binding site

<400> SEQUENCE: 10
cggaggactg tcctccg                                                    17

<210> SEQ ID NO 11
<211> LENGTH: 17
<212> TYPE: DNA
<213> ORGANISM: Saccharomyces sp.
<220> FEATURE:
<222> LOCATION: (1)..(17)
<223> OTHER INFORMATION: GAL4 DNA binding site

<400> SEQUENCE: 11
gcctcctgac aggaggc                                                    17

<210> SEQ ID NO 12
<211> LENGTH: 9
<212> TYPE: DNA
<213> ORGANISM: Saccharomyces sp.
<220> FEATURE:
<222> LOCATION: (1)..(9)
<223> OTHER INFORMATION: MAT alpha 2 DNA binding site

<400> SEQUENCE: 12 catgtaatt                                                              9

<210> SEQ ID NO 13
<211> LENGTH: 9
<212> TYPE: DNA
<213> ORGANISM: Saccharomyces sp.
<220> FEATURE:
<222> LOCATION: (1)..(9)
<223> OTHER INFORMATION: MAT alpha 2 DNA binding site

<400> SEQUENCE: 13 gtacattaa                                                              9

<210> SEQ ID NO 14
<211> LENGTH: 9
<212> TYPE: DNA
<213> ORGANISM: Saccharomyces sp.
<220> FEATURE:
<222> LOCATION: (1)..(9)
<223> OTHER INFORMATION: GCN4 DNA binding site

<400> SEQUENCE: 14 atgactcat                                                              9

<210> SEQ ID NO 15
<211> LENGTH: 9
<212> TYPE: DNA
<213> ORGANISM: Saccharomyces sp.
<220> FEATURE:
<222> LOCATION: (1)..(9)
<223> OTHER INFORMATION: GCN4 DNA binding site

<400> SEQUENCE: 15 tactgagta                                                              9
```

```
<210> SEQ ID NO 16
<211> LENGTH: 10
<212> TYPE: DNA
<213> ORGANISM: Drosophila sp.
<220> FEATURE:
<222> LOCATION: (1)..(10)
<223> OTHER INFORMATION: Kruppel DNA binding site

<400> SEQUENCE: 16
aacgggttaa                                                          10

<210> SEQ ID NO 17
<211> LENGTH: 10
<212> TYPE: DNA
<213> ORGANISM: Drosophila sp.
<220> FEATURE:
<222> LOCATION: (1)..(10)
<223> OTHER INFORMATION: Kruppel DNA binding site

<400> SEQUENCE: 17
ttgcccaatt                                                          10

<210> SEQ ID NO 18
<211> LENGTH: 9
<212> TYPE: DNA
<213> ORGANISM: Drosophila sp.
<220> FEATURE:
<222> LOCATION: (1)..(9)
<223> OTHER INFORMATION: bicoid DNA binding site

<400> SEQUENCE: 18 gggattaga                                                            9

<210> SEQ ID NO 19
<211> LENGTH: 9
<212> TYPE: DNA
<213> ORGANISM: Drosophila sp.
<220> FEATURE:
<222> LOCATION: (1)..(9)
<223> OTHER INFORMATION: bicoid DNA binding site

<400> SEQUENCE: 19 ccctaatct                                                            9

<210> SEQ ID NO 20
<211> LENGTH: 6
<212> TYPE: DNA
<213> ORGANISM: Homo sapiens
<220> FEATURE:
<222> LOCATION: (1)..(6)
<223> OTHER INFORMATION: SP1 DNA binding site

<400> SEQUENCE: 20 gggcgg                                                               6

<210> SEQ ID NO 21
<211> LENGTH: 6
<212> TYPE: DNA
<213> ORGANISM: Homo sapiens
<220> FEATURE:
<222> LOCATION: (1)..(6)
<223> OTHER INFORMATION: SP1 DNA binding site

<400> SEQUENCE: 21 cccgcc                                                               6
```

```
<210> SEQ ID NO 22
<211> LENGTH: 8
<212> TYPE: DNA
<213> ORGANISM: Homo sapiens
<220> FEATURE:
<222> LOCATION: (1)..(8)
<223> OTHER INFORMATION: Oct1 DNA binding site

<400> SEQUENCE: 22 atgcaaat                                                                    8

<210> SEQ ID NO 23
<211> LENGTH: 8
<212> TYPE: DNA
<213> ORGANISM: Homo sapiens
<220> FEATURE:
<222> LOCATION: (1)..(8)
<223> OTHER INFORMATION: Oct-1 DNA binding site

<400> SEQUENCE: 23 tacgttta                                                                    8

<210> SEQ ID NO 24
<211> LENGTH: 6
<212> TYPE: DNA
<213> ORGANISM: Homo sapiens
<220> FEATURE:
<222> LOCATION: (1)..(6)
<223> OTHER INFORMATION: GATA-1 DNA binding site

<400> SEQUENCE: 24 tgatag                                                                      6

<210> SEQ ID NO 25
<211> LENGTH: 6
<212> TYPE: DNA
<213> ORGANISM: Homo sapiens
<220> FEATURE:
<222> LOCATION: (1)..(6)
<223> OTHER INFORMATION: GATA-1 DNA binding site

<400> SEQUENCE: 25 actatc                                                                      6

<210> SEQ ID NO 26
<211> LENGTH: 20
<212> TYPE: DNA
<213> ORGANISM: Artificial Sequence
<220> FEATURE:
<222> LOCATION: (1)..(20)
<223> OTHER INFORMATION: probe sequence

<400> SEQUENCE: 26
agctactgat gcagtcacgt                                                      20

<210> SEQ ID NO 27
<211> LENGTH: 20
<212> TYPE: DNA
<213> ORGANISM: Artificial Sequence
<220> FEATURE:
<222> LOCATION: (1)..(20)
<223> OTHER INFORMATION: capture element

<400> SEQUENCE: 27
tcgatgacta cgtcagtgca                                                      20
```

<210> SEQ ID NO 28
<211> LENGTH: 21
<212> TYPE: DNA
<213> ORGANISM: Escherichia coli
<220> FEATURE:
<222> LOCATION: (1)..(21)
<223> OTHER INFORMATION: lac repressor DNA binding site (complimentary strand)

<400> SEQUENCE: 28
ttaacactcg cctattgtta a                                          21

<210> SEQ ID NO 29
<211> LENGTH: 49
<212> TYPE: DNA
<213> ORGANISM: Artificial Sequence
<220> FEATURE:
<223> OTHER INFORMATION: primer
<220> FEATURE:
<222> LOCATION: (1)..(49)
<223> OTHER INFORMATION: pCAL-n-EK cloning oligonucleotide

<400> SEQUENCE: 29
gacgacgaca agatgggtgt cccaattggt gagattatac caagaaaag            49

<210> SEQ ID NO 30
<211> LENGTH: 56
<212> TYPE: DNA
<213> ORGANISM: Artificial Sequence
<220> FEATURE:
<222> LOCATION: (1)..(56)
<223> OTHER INFORMATION: pCAL-n-EK cloning oligonucleotide

<400> SEQUENCE: 30
ggaacaagac ccgtttatct cttgaaccaa ctttcaaggg ttgattgttt tccact    56

<210> SEQ ID NO 31
<211> LENGTH: 19
<212> TYPE: DNA
<213> ORGANISM: Artificial Sequence
<220> FEATURE:
<221> NAME/KEY: Universal hairpin probe b171
<222> LOCATION: (1)..(19)
<223> OTHER INFORMATION: Universal hairpin probe b171consists of a 5' terminal T attached to a fluorophor FAM group and a 3' terminal A attached to a quencher Dabcyl group.

<400> SEQUENCE: 31
tcgcagtgtc gacctgcgc                                             19

<210> SEQ ID NO 32
<211> LENGTH: 40
<212> TYPE: DNA
<213> ORGANISM: Artificial Sequence
<220> FEATURE:
<221> NAME/KEY: probe SP170a
<222> LOCATION: (1)..(40)
<223> OTHER INFORMATION: Probe 2 or SP170a consists of a stem-loop comprising two domains: the 5' two thirds have a (universal) sequence complementary to the hairpin probe 1 (SEQ ID NO: 31), and nucleotides that will
<220> FEATURE:
<223> OTHER INFORMATION: stop the DNA polymerase, and the 3' one third, which serves as the target specific primer. X: any nucleotid

<400> SEQUENCE: 32
cagccgtcga tccgcaggtc gacactgccg tcgacggctg                      40

```
<210> SEQ ID NO 33
<211> LENGTH: 12
<212> TYPE: DNA
<213> ORGANISM: Artificial Sequence
<220> FEATURE:
<222> LOCATION: (1)..(12)
<223> OTHER INFORMATION: Sequence of top strand synthesized from reverse
      primer (3' one third of probe 2, SP170a, SEQ ID NO: 32

<400> SEQUENCE: 33
gcagctgccg ac                                                            12

<210> SEQ ID NO 34
<211> LENGTH: 30
<212> TYPE: DNA
<213> ORGANISM: Artificial Sequence
<220> FEATURE:
<222> LOCATION: (1)..(30)
<223> OTHER INFORMATION: 5' two thirds of probe 2 (SEQ ID NO: 32)
      containing sequences that are complimentary to the universal
      hairpin probe 1 (b171, SEQ ID NO: 31

<400> SEQUENCE: 34
tccgcaggtc gacactgccg tcgacggctg                                         30

<210> SEQ ID NO 35
<211> LENGTH: 15
<212> TYPE: DNA
<213> ORGANISM: Artificial Sequence
<220> FEATURE:
<222> LOCATION: (1)..(15)
<223> OTHER INFORMATION: B1 primer

<400> SEQUENCE: 35
cgatcgagca agcca                                                         15

<210> SEQ ID NO 36
<211> LENGTH: 14
<212> TYPE: DNA
<213> ORGANISM: Artificial Sequence
<220> FEATURE:
<222> LOCATION: (1)..(14)
<223> OTHER INFORMATION: primer B2

<400> SEQUENCE: 36
cgagccgctc gctg                                                          14

<210> SEQ ID NO 37
<211> LENGTH: 40
<212> TYPE: DNA
<213> ORGANISM: Artificial Sequence
<220> FEATURE:
<222> LOCATION: (1)..(40)
<223> OTHER INFORMATION: primer S1

<400> SEQUENCE: 37
accgcatcga atgcatgtct cgggtaaggc gtactcgacc                              40

<210> SEQ ID NO 38
<211> LENGTH: 80
<212> TYPE: DNA
<213> ORGANISM: Artificial Sequence
<220> FEATURE:
<223> OTHER INFORMATION: primer
<220> FEATURE:
<222> LOCATION: (1)..(40)
<223> OTHER INFORMATION: primer S2
```

-continued

```
<400> SEQUENCE: 38
cgattccgct ccagacttct cgggtgtact gagatcccct accgcatcga atgcatgtct    60
cgggtaaggc gtactcgacc                                                80

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
aaggcgtact cgacctgaaa                                                20

<210> SEQ ID NO 40
<211> LENGTH: 21
<212> TYPE: DNA
<213> ORGANISM: Artificial Sequence
<220> FEATURE:
<222> LOCATION: (1)..(21)
<223> OTHER INFORMATION: probefluorogenic

<400> SEQUENCE: 40
accatacgga tagggatct c                                               21

<210> SEQ ID NO 41
<211> LENGTH: 20
<212> TYPE: DNA
<213> ORGANISM: Artificial Sequence
<220> FEATURE:
<223> OTHER INFORMATION: synthetic DNA

<400> SEQUENCE: 41
gcaaagtatc atccctccag                                                20

<210> SEQ ID NO 42
<211> LENGTH: 120
<212> TYPE: DNA
<213> ORGANISM: Artificial Sequence
<220> FEATURE:
<222> LOCATION: (1)..(120)
<223> OTHER INFORMATION: target synthetic

<400> SEQUENCE: 42
cctctgcaga ctactattac ataatacgac tcactatagg gatctgcacg tattagccta    60
tagtgagtcg tattaatagg aaacaccaaa gatgatattt cgtcacagca agaattcagg   120

<210> SEQ ID NO 43
<211> LENGTH: 20
<212> TYPE: DNA
<213> ORGANISM: Artificial Sequence
<220> FEATURE:
<223> OTHER INFORMATION: synthetic DNA
<220> FEATURE:
<222> LOCATION: (1)..(20)
<223> OTHER INFORMATION: target DNA P1

<400> SEQUENCE: 43
cctctgcaga ctactattac                                                20

<210> SEQ ID NO 44
<211> LENGTH: 20
<212> TYPE: DNA
<213> ORGANISM: Artificial Sequence
```

```
<220> FEATURE:
<223> OTHER INFORMATION: synthetic DNA
<220> FEATURE:
<222> LOCATION: (1)..(20)
<223> OTHER INFORMATION: target DNA P2

<400> SEQUENCE: 44
cctgaattct tgctgtgacg                                                    20

<210> SEQ ID NO 45
<211> LENGTH: 24
<212> TYPE: DNA
<213> ORGANISM: Artificial Sequence
<220> FEATURE:
<222> LOCATION: (1)..(24)
<223> OTHER INFORMATION: probe fluorogenic

<400> SEQUENCE: 45
taggaaacac caaagatgat attt                                               24

<210> SEQ ID NO 46
<211> LENGTH: 95
<212> TYPE: DNA
<213> ORGANISM: Artificial Sequence
<220> FEATURE:
<222> LOCATION: (1)..(95)
<223> OTHER INFORMATION: circle probe open

<400> SEQUENCE: 46
gaggagaata aaagtttctc ataagactcg tcatgtctca gcagcttcta acggtcacta        60
atacgactca ctataggttc tgcctctggg aacac                                   95

<210> SEQ ID NO 47
<211> LENGTH: 18
<212> TYPE: DNA
<213> ORGANISM: Artificial Sequence
<220> FEATURE:
<222> LOCATION: (1)..(18)
<223> OTHER INFORMATION: circle replication primer rolling

<400> SEQUENCE: 47
gctgagacat gacgagtc                                                      18

<210> SEQ ID NO 48
<211> LENGTH: 23
<212> TYPE: DNA
<213> ORGANISM: Artificial Sequence
<220> FEATURE:
<222> LOCATION: (1)..(23)
<223> OTHER INFORMATION: primer upstream

<400> SEQUENCE: 48
aagtttctca taagactcgt cat                                                23

<210> SEQ ID NO 49
<211> LENGTH: 23
<212> TYPE: DNA
<213> ORGANISM: Artificial Sequence
<220> FEATURE:
<222> LOCATION: (1)..(23)
<223> OTHER INFORMATION: primer reverse

<400> SEQUENCE: 49
aggcagaacc tatagtgagt cgt                                                23
```